US008858925B2

(12) United States Patent
Seliktar et al.

(10) Patent No.: US 8,858,925 B2
(45) Date of Patent: *Oct. 14, 2014

(54) PEGYLATED FIBRINOGEN PRECURSOR MOLECULE

(75) Inventors: Dror Seliktar, Haifa (IL); Liora Almany, Atlit (IL)

(73) Assignee: Regentis Biomaterials Ltd., Or-Akiva (IL)

( * ) Notice: Subject to any disclaimer, the term of this patent is extended or adjusted under 35 U.S.C. 154(b) by 195 days.

This patent is subject to a terminal disclaimer.

(21) Appl. No.: 13/181,562

(22) Filed: Jul. 13, 2011

(65) Prior Publication Data

US 2012/0020911 A1    Jan. 26, 2012

Related U.S. Application Data

(63) Continuation of application No. 11/472,437, filed on Jun. 22, 2006, now Pat. No. 8,007,774, which is a continuation-in-part of application No. PCT/IL2004/001136, filed on Dec. 15, 2004.

(60) Provisional application No. 60/530,917, filed on Dec. 22, 2003.

(51) Int. Cl.
| | | |
|---|---|---|
| *A61F 13/00* | (2006.01) | |
| *A61L 27/24* | (2006.01) | |
| *A61K 47/48* | (2006.01) | |
| *A61K 38/36* | (2006.01) | |
| *A61L 27/18* | (2006.01) | |
| *A61L 27/22* | (2006.01) | |
| *A61L 27/38* | (2006.01) | |
| *A61L 27/52* | (2006.01) | |
| *C12N 5/00* | (2006.01) | |

(52) U.S. Cl.
CPC ............ *A61L 27/227* (2013.01); *A61L 27/24* (2013.01); *A61K 47/48784* (2013.01); *A61K 38/363* (2013.01); *C12N 2533/54* (2013.01); *A61K 47/48215* (2013.01); *A61L 27/18* (2013.01); *A61L 27/38* (2013.01); *C12N 2533/30* (2013.01); *A61K 47/48292* (2013.01); *A61L 27/52* (2013.01); *C12N 2533/50* (2013.01); *C12N 2533/40* (2013.01); *C12N 2533/52* (2013.01); *C12N 5/0068* (2013.01)
USPC .............................. 424/78.2; 424/78; 530/350

(58) Field of Classification Search
None
See application file for complete search history.

(56) References Cited

U.S. PATENT DOCUMENTS

| | | | |
|---|---|---|---|
| 4,069,216 A * | 1/1978 | Shanbrom | 530/383 |
| 4,188,318 A * | 2/1980 | Shanbrom | 530/383 |
| 4,925,924 A | 5/1990 | Silver et al. | |
| 4,970,298 A | 11/1990 | Silver et al. | |
| 5,410,016 A | 4/1995 | Hubbell et al. | |
| 5,529,914 A | 6/1996 | Hubbell et al. | |
| 5,567,435 A | 10/1996 | Hubbell et al. | |
| 5,573,934 A | 11/1996 | Hubbell et al. | |
| 5,614,587 A | 3/1997 | Rhee et al. | |
| 5,626,863 A | 5/1997 | Hubbell et al. | |
| 5,733,563 A | 3/1998 | Fortier | |
| 5,834,274 A | 11/1998 | Hubbell et al. | |
| 5,843,743 A | 12/1998 | Hubbell et al. | |
| 5,858,746 A | 1/1999 | Hubbell et al. | |
| 5,863,984 A | 1/1999 | Doillon et al. | |
| 5,902,599 A | 5/1999 | Anseth et al. | |
| 5,986,043 A | 11/1999 | Hubbell et al. | |
| 6,060,582 A | 5/2000 | Hubbell et al. | |
| 6,129,761 A | 10/2000 | Hubbell | |
| 6,153,211 A | 11/2000 | Hubbell et al. | |
| 6,224,893 B1 | 5/2001 | Langer et al. | |
| 6,306,922 B1 | 10/2001 | Hubbell et al. | |
| 6,403,672 B1 | 6/2002 | Randolph et al. | |
| 6,565,842 B1 | 5/2003 | Sojomihardjo et al. | |
| 6,703,037 B1 | 3/2004 | Hubbell et al. | |
| 6,858,229 B1 | 2/2005 | Hubbell et al. | |
| 6,864,301 B2 | 3/2005 | Randolph et al. | |
| 6,911,227 B2 | 6/2005 | Hubbell et al. | |
| 7,842,667 B2 | 11/2010 | Seliktar et al. | |
| 2004/0082511 A1 | 4/2004 | Watzek et al. | |
| 2006/0233854 A1 | 10/2006 | Seliktar et al. | |
| 2006/0233855 A1 | 10/2006 | Seliktar et al. | |

FOREIGN PATENT DOCUMENTS

| | | |
|---|---|---|
| EP | 0605797 | 7/1994 |
| EP | 0680990 | 11/1995 |
| EP | 0976759 | 2/2000 |
| WO | WO 98/32466 | 7/1998 |
| WO | WO 99/34833 | 7/1999 |
| WO | WO 01/53324 | 7/2001 |
| WO | WO 02/18441 | 3/2002 |
| WO | WO 2004/041298 | 5/2004 |
| WO | WO 2005/061018 | 7/2005 |

OTHER PUBLICATIONS

Almany et al. (Biomaterials, vol. 26, pp. 2467-2477, 2005).*
Communication Under Rule 71(3) EPC Dated Nov. 2, 2011 From the European Patent Office Re.: Application No. 04806668.2.
International Preliminary Report on Patentability Dated Jul. 6, 2006 From the International Bureau of WIPO Re.: Application No. PCT/IL2004/001136.
International Search Report Dated Aug. 2, 2005 From the International Searching Authority Re.: Application No. PCT/IL2004/001136.
Official Action Dated Oct. 4, 2007 From the US Patent and Trademark Office Re.: U.S. Appl. No. 11/472,520.

(Continued)

*Primary Examiner* — Hope Robinson

(57) ABSTRACT

The present invention relates to biodegradable scaffolds composed of a naturally-occurring protein backbone cross-linked by a synthetic polymer. Specifically, the present invention provides PEGylated-fibrinogen scaffold and methods of generating and using same for treating disorders requiring tissue regeneration.

9 Claims, 30 Drawing Sheets
(21 of 30 Drawing Sheet(s) Filed in Color)

(56) References Cited

OTHER PUBLICATIONS

Official Action Dated Jan. 8, 2009 From the US Patent and Trademark Office Re.: U.S. Appl. No. 11/472,437.
Official Action Dated Apr. 28, 2008 From the US Patent and Trademark Office Re.: U.S. Appl. No. 11/472,520.
Communication Pursuant to Article 94(3) EPC Dated Dec. 2, 2010 From the European Patent Office Re. Application No. 04806668.2.
Communication Pursuant to Article 94(3) EPC Dated Jan. 5, 2009 From the European Patent Office Re.: Application No. 04806668.2.
Communication Pursuant to Article 94(3) EPC Dated Jul. 6, 2009 From the European Patent Office Re.: Application No. 04806668.2.
Communication Pursuant to Article 94(3) EPC Dated Jul. 25, 2008 From the European Patent Office Re.: Application No. 07110777.5.
Communication Pursuant to Article 96(2) EPC Dated Dec. 11, 2006 From the European Patent Office Re.: Application No. 04806668.2.
Communication Pursuant to Rules 70(2) and 70a(2) EPC and Reference to Rule 39(1) EPC Dated Jun. 28, 2011 From the European Patent Office Re. Application No. 10012382.7.
European Search Report and the European Search Opinion Dated May 20, 2011 From the European Patent Office Re. Application No. 10012382.7.
European Search Report Dated Oct. 22, 2007 From the European Patent Office Re.: Application No. 07110777.5.
International Search Report Dated Jun. 1, 2005 From the International Searching Authority Re.: Application No. PCT/IL2004/001136.
Interview Summary Dated Oct. 18, 2010 From the US Patent and Trademark Office Re.: U.S. Appl. No. 11/472,437.
Invitation Pursuant to Article 94(3) and Rule 71(1) EPC Dated Jun. 10, 2010 From the European Patent Office Re. Application No. 04806668.2.
Notice of Allowance Dated Apr. 11, 2011 From the US Patent and Trademark Office Re.: U.S. Appl. No. 11/472,437.
Notice of Allowance Dated Jul. 26, 2010 From the US Patent and Trademark Office Re.: U.S. Appl. No. 11/472,520.
Official Action Dated Jan. 3, 2011 From the US Patent and Trademark Office Re.: U.S. Appl. No. 11/472,437.
Official Action Dated Feb. 4, 2010 From the US Patent and Trademark Office Re.: U.S. Appl. No. 11/472,520.
Official Action Dated Aug. 7, 2008 From the US Patent and Trademark Office Re.: U.S. Appl. No. 11/472,437.
Official Action Dated Nov. 12, 2008 From the US Patent and Trademark Office Re.: U.S. Appl. No. 11/472,520.
Official Action Dated Jun. 15, 2007 From the US Patent and Trademark Office Re.: U.S. Appl. No. 11/472,520.
Official Action Dated Sep. 17, 2009 From the US Patent and Trademark Office Re.: U.S. Appl. No. 11/472,437.
Official Action Dated Jan. 21, 2010 From the US Patent and Trademark Office Re.: U.S. Appl. No. 11/472,437.
Official Action Dated Jul. 22, 2009 From the US Patent and Trademark Office Re.: U.S. Appl. No. 11/472,520.
Official Action Dated Jun. 29, 2010 From the US Patent and Trademark Office Re.: U.S. Appl. No. 11/472,437.
Response Dated May 3, 2010 to Official Action of Feb. 4, 2010 From the US Patent and Trademark Office Re.: U.S. Appl. No. 11/472,520.
Response Dated Apr. 4, 2011 to Official Action of Jan. 3, 2011 From the US Patent and Trademark Office Re.: U.S. Appl. No. 11/472,437.
Response Dated Mar. 4, 2011 to Communication Pursuant to Article 94(3) EPC of Dec. 2, 2010 From the European Patent Office Re. Application No. 04806668.2.
Response Dated Dec. 16, 2009 to Official Action of Sep. 17, 2009 From the US Patent and Trademark Office Re.: U.S. Appl. No. 11/472,437.
Response Dated Oct. 18, 2010 to Invitation Pursuant to Article 94(3) and Rule 71(1) EPC of Jun. 10, 2010 From the European Patent Office Re. Application No. 04806668.2.
Response Dated Oct. 19, 2009 to Official Action of Jul. 22, 2009 From the US Patent and Trademark Office Re.: U.S. Appl. No. 11/472,520.
Response Dated Apr. 21, 2010 to Official Action of Jan. 21, 2010 From the US Patent and Trademark Office Re.: U.S. Appl. No. 11/472,437.
Response Dated Jan. 28, 2010 to Communication Pursuant to Article 94(3) EPC of Jul. 6, 2009 From the European Patent Office Re.: Application No. 04806668.2.
Response Dated Oct. 28, 2010 to Official Action of Jun. 29, 2010 From the US Patent and Trademark Office Re.: U.S. Appl. No. 11/472,437.
Written Opinion Dated Jun. 1, 2005 From the International Searching Authority Re.: Application No. PCT/IL2004/001136.
Almany et al. "Biosynthetic Hydrogel Scaffolds Made From Fibrinogen and Polyethylene Glycol for 3D Cell Cultures", Biomaterials, XP004673411, 26(15): 2467-2477, May 15, 2005. § [03.5], [0004], p. 2471, Table 1.
Deible et al. "Molecular Barriers to Biomaterial Thrombosis by Modification of Surface Proteins With Polyethylene Glycol", Biomaterials, 19: 1885-1893, 1998.
Dikovsky et al. "The Effect of Structural Alterations of PEG-Fibrinogen Hydrogel Scaffolds on 3-D Cellular Morphology and Cellular Migration", Biomaterials, XP005193217, 27(8): 1496-1506, Oct. 21, 2005. Abstract, p. 1497, § 2.1, 2.2.
D'Urso et al. "Poly(Ethylene Glycol)-Serum Albumin Hydrogel as Matrix for Enzyme Immobilization: Biomedical Applications", Art. Cells, Blood Subs., and Biotech., 23(5): 587-595, 1995.
Gayet et al. "Drug Release From New Bioartificial Hydrogel", Art. Cells, Blood Subs., and Immob. Biotech., 23(5): 605-611, 1995.
Halstenberg et al. "Biologically Engineered Protein-Graft-Poly(Ethylene Glycol) Hydrogels: A Cell Adhesive and Plasmin-Degradable Biosynthetic Material for Tissue Repair", Biomacromolecules, XP002454079, 3(4): 710-723, Jul. 2002. Abstract, p. 713, col. 2, § 3-p. 714, col. 1, § 2.
Hooftman et al. "Review: Poly(Ethylene Glycol)s With Reactive Endgroups. II. Practical Consideratiion for the Preparation of Protein-PEG Conjugates", Journal of Bioactive and Compatible Polymers, 11: 135-159, 1996.
Li et al. "Synthesis of Polyethylene Glycol (PEG) Derivatives and PEGylated-Peptide Biopolymer Conjugates", Biomacromolecules, 4: 1055-1067, 2003.
Meyers et al. "A Fibrin Adhesive Seal for the Repair of Osteochondral Fracture Fragments", Clinical Orthopaedics and Related Research, 182: 258-263, Jan.-Feb. 1984.
Pfl?ger et al. "Untersuchungen ?ber das Einwachsen von Knochengewebe in por?se Metallimplantate", Wiener Klinische Wochenschrift, 91(14): 482-487, Jul. 13, 1979. & Translation Into English.
Seliktar et al. "MMP-2 Sensitive, VEGF-Bearing Bioactive Hydrogels for Promotion of Vascular Healing", Journal of Biomedical Materials Research, Part. A, 68(4): 704-716, 2004.
Veronese "Peptide and Protein PEGylation: A Review of Problems and Solutions", Biomaterials, 22: 405-417, 2001.
Wells "Additivity of Mutational Effects in Proteins", Perspectives in Biochemistry, Biochemistry, 29(37): 8509-8517, Sep. 18, 1990.
Zalipsky "Chemistry of Polyethylene Glycol Conjugates With Biologically Active Molecules", Advanced Drug Delivery Reviews, 16: 157-182, 1995.
Communication Pursuant to Article 94(3) EPC Dated Apr. 2, 2012 From the European Patent Office Re. Application No. 10012382.7.
Summons to Attend Oral Proceedings Pursuant to Rule 115(1) EPC Dated Jan. 28, 2013 From the European Patent Office Re. Application No. 07110777.5.
Invitation Pursuant to Article 94(3) and Rule 71(1) EPC Dated May 19, 2011 From the European Patent Office Re. Application No. 04806668.2.
Response Dated Jul. 29, 2011 to Invitation Pursuant to Article 94(3) and Rule 71(1) EPC of May 19, 2011 From the European Patent Office Re. Application No. 04806668.2.
Restriction Official Action Dated Apr. 30, 2014 From the US Patent and Trademark Office Re. U.S. Appl. No. 12/912,809.

\* cited by examiner

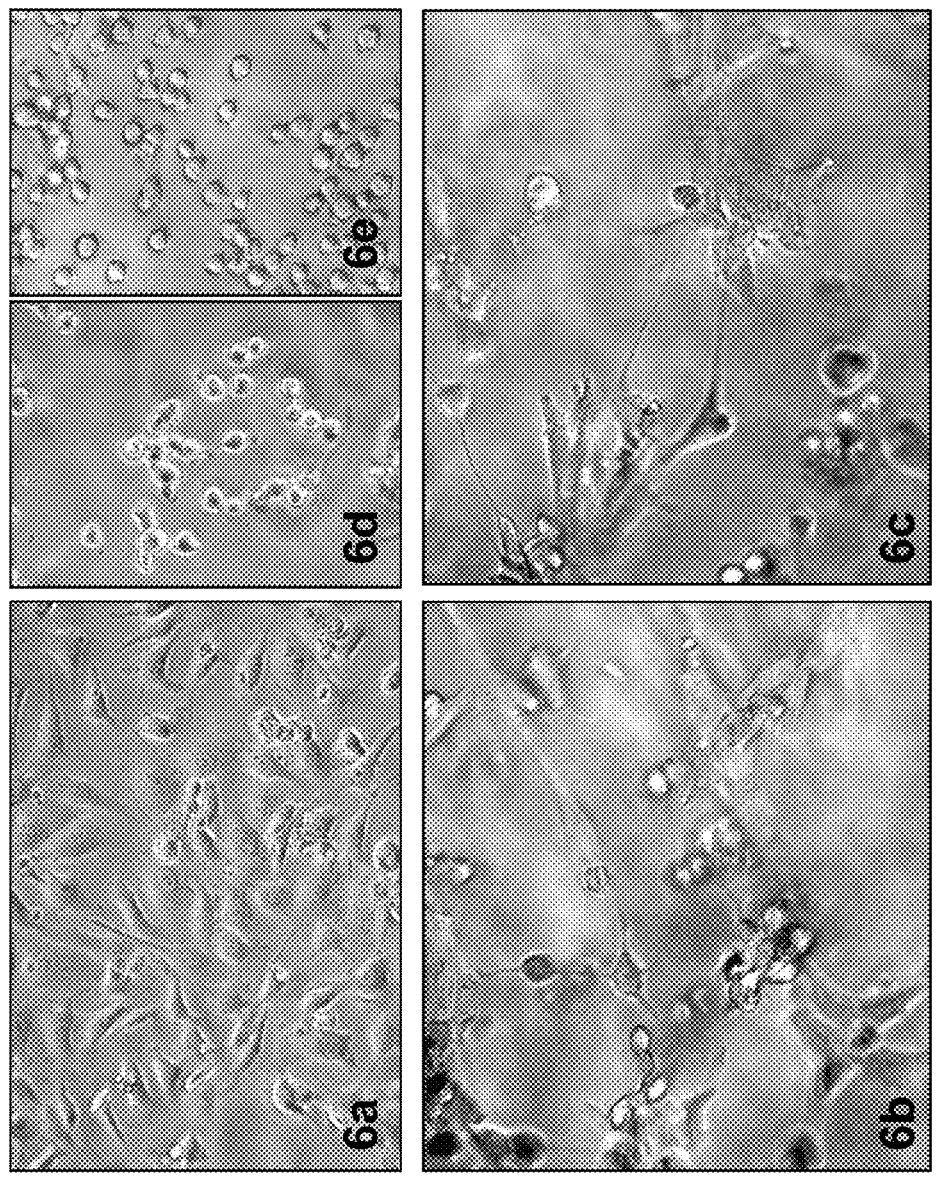
Figures 6a-e

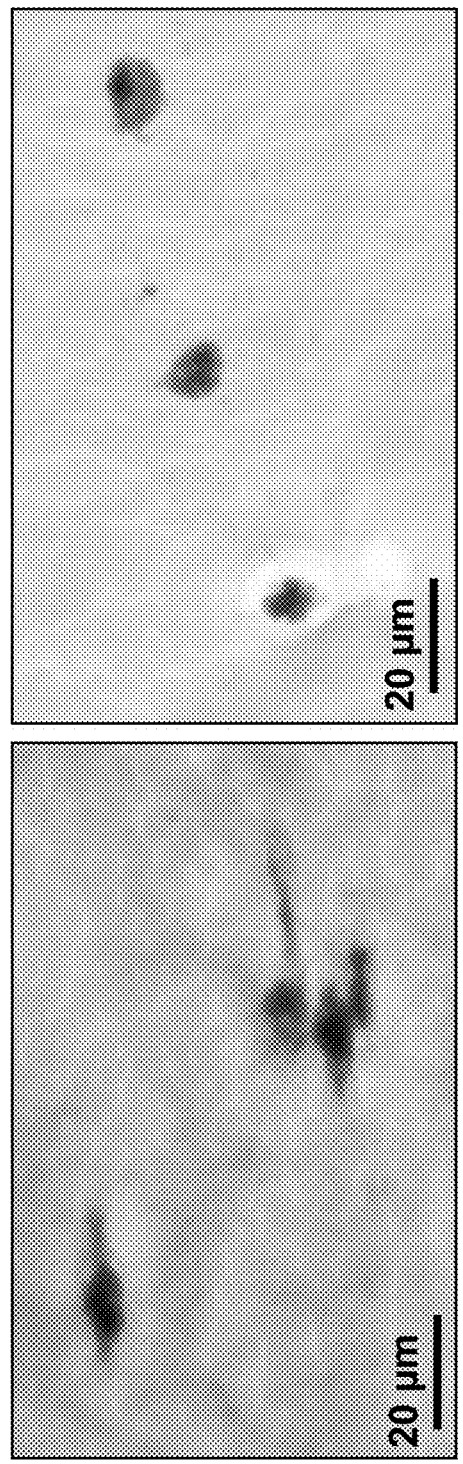

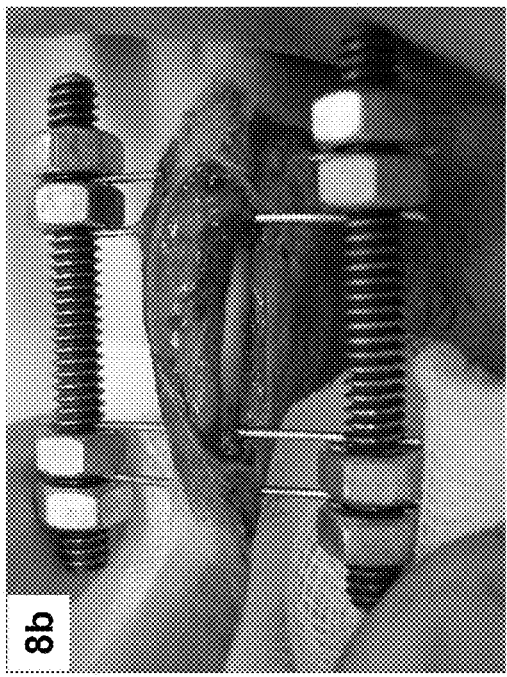
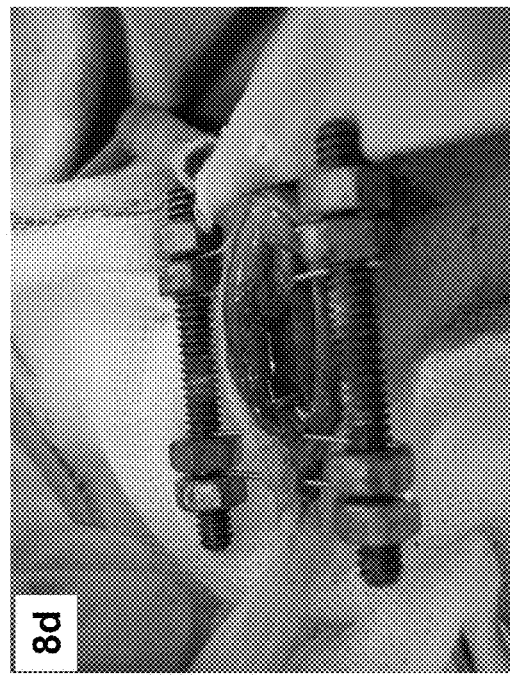
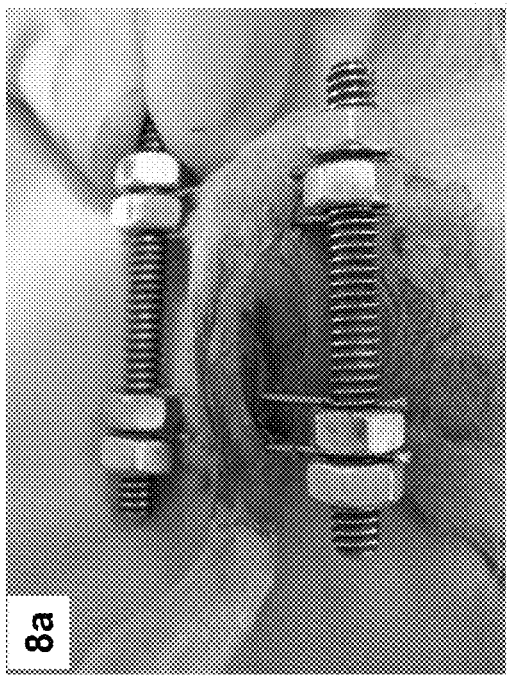
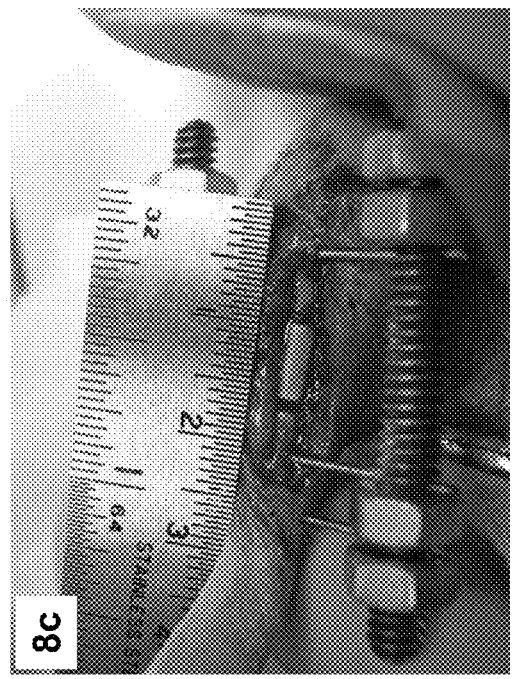
Figures 8a-d

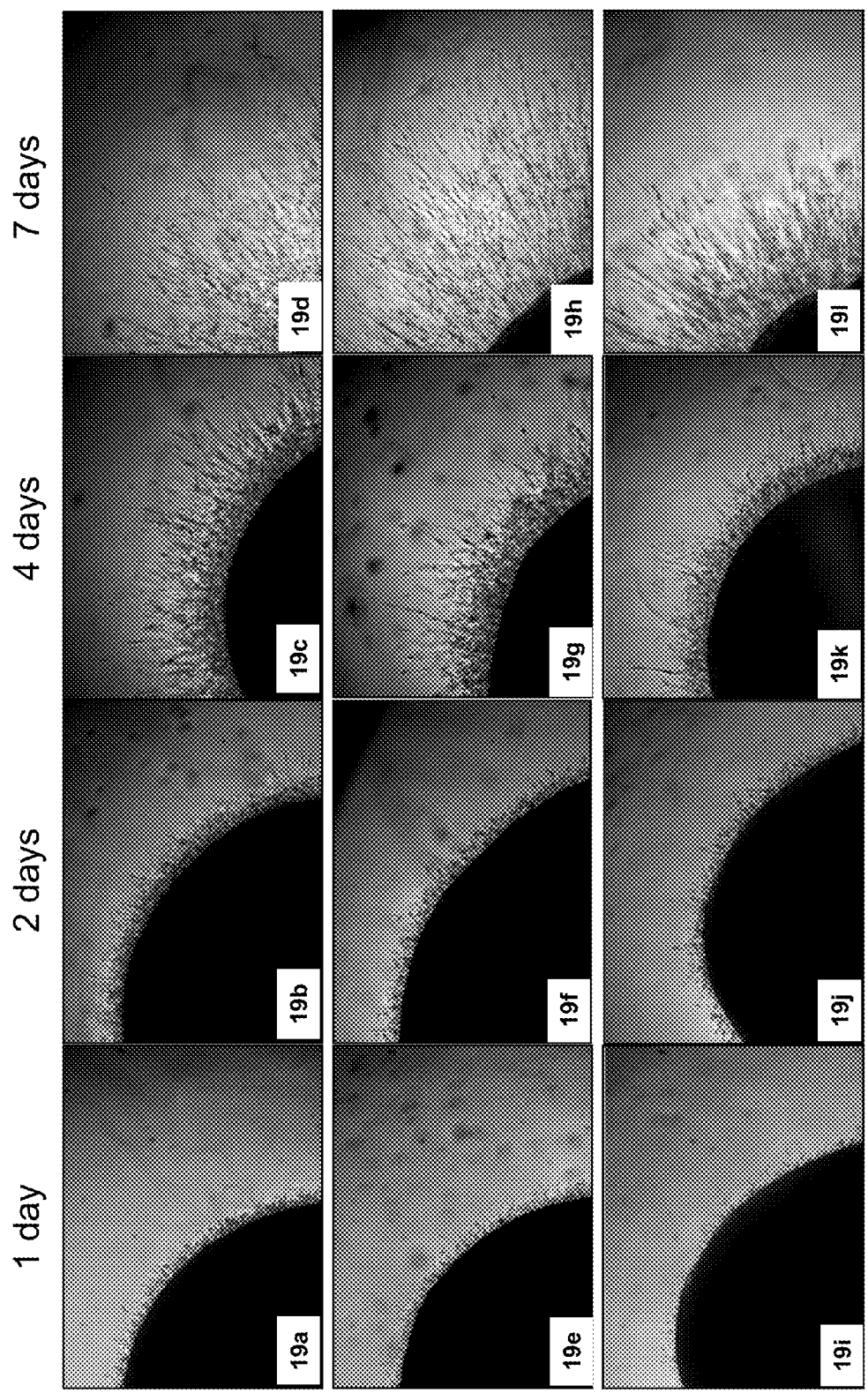
Figures 19a-l

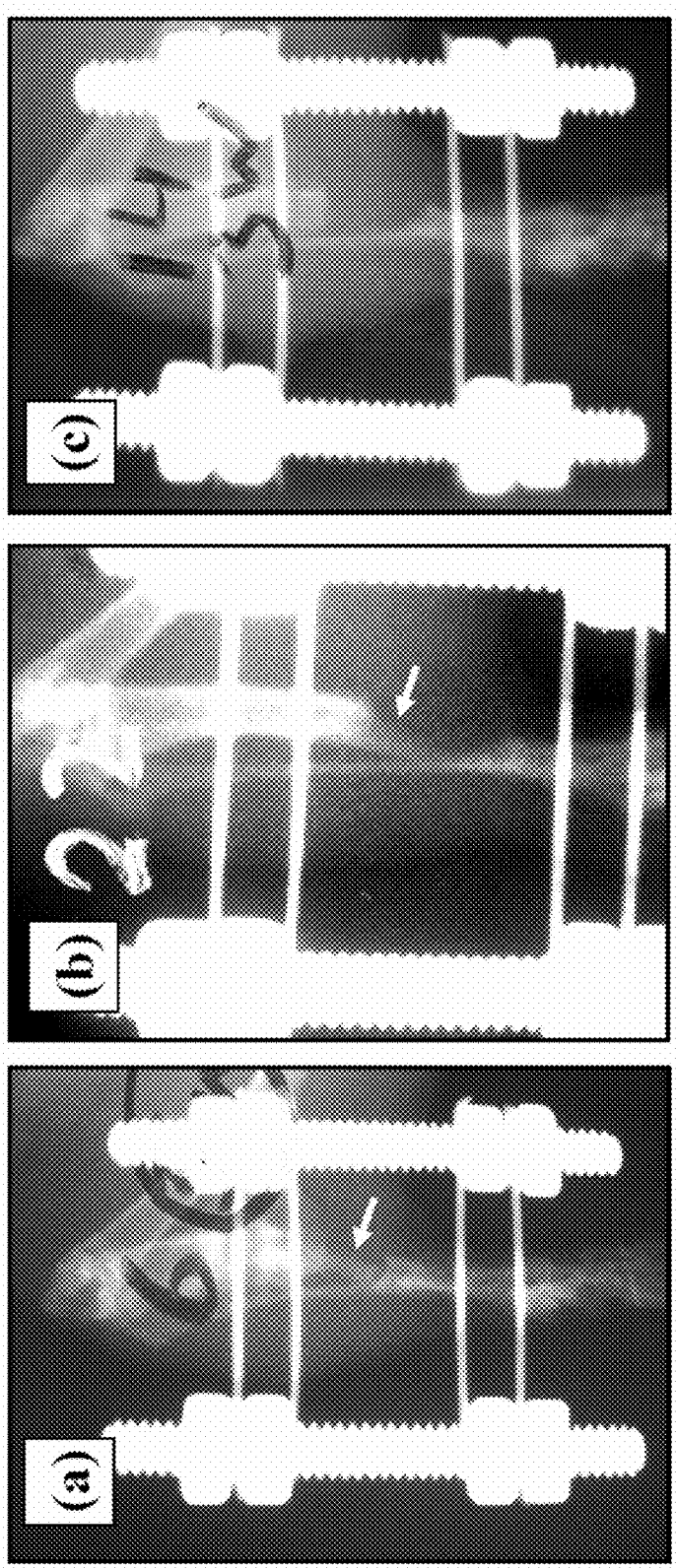
FIGs. 20a-c

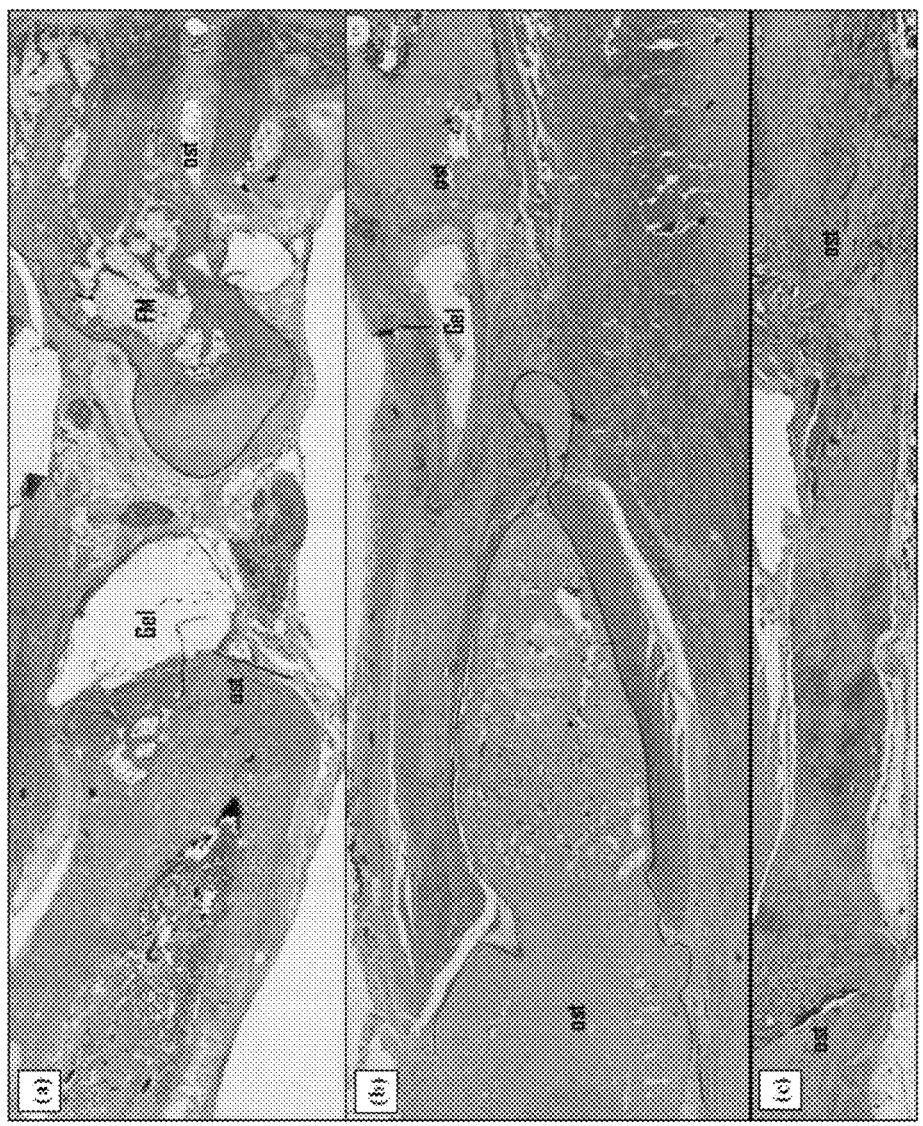
FIGs. 21a-c

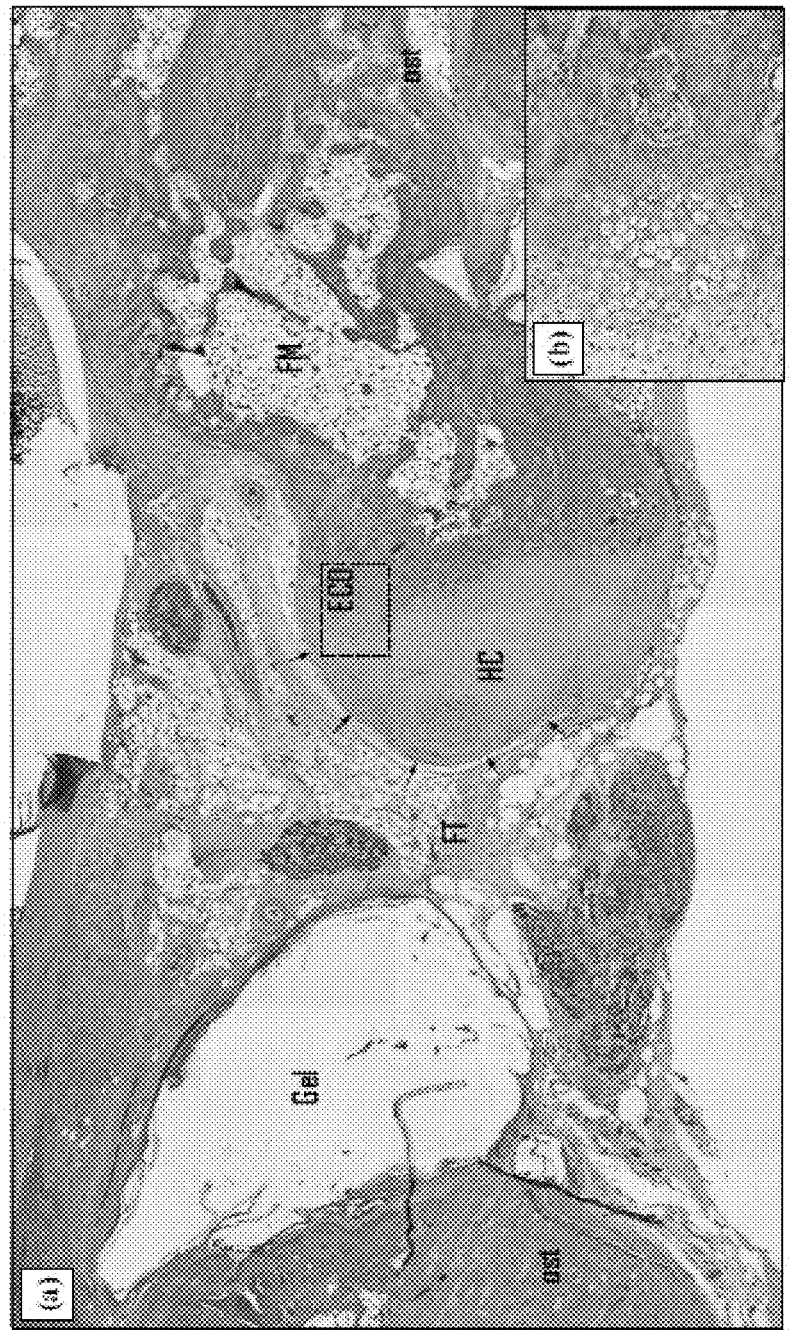
FIGs. 22a-b

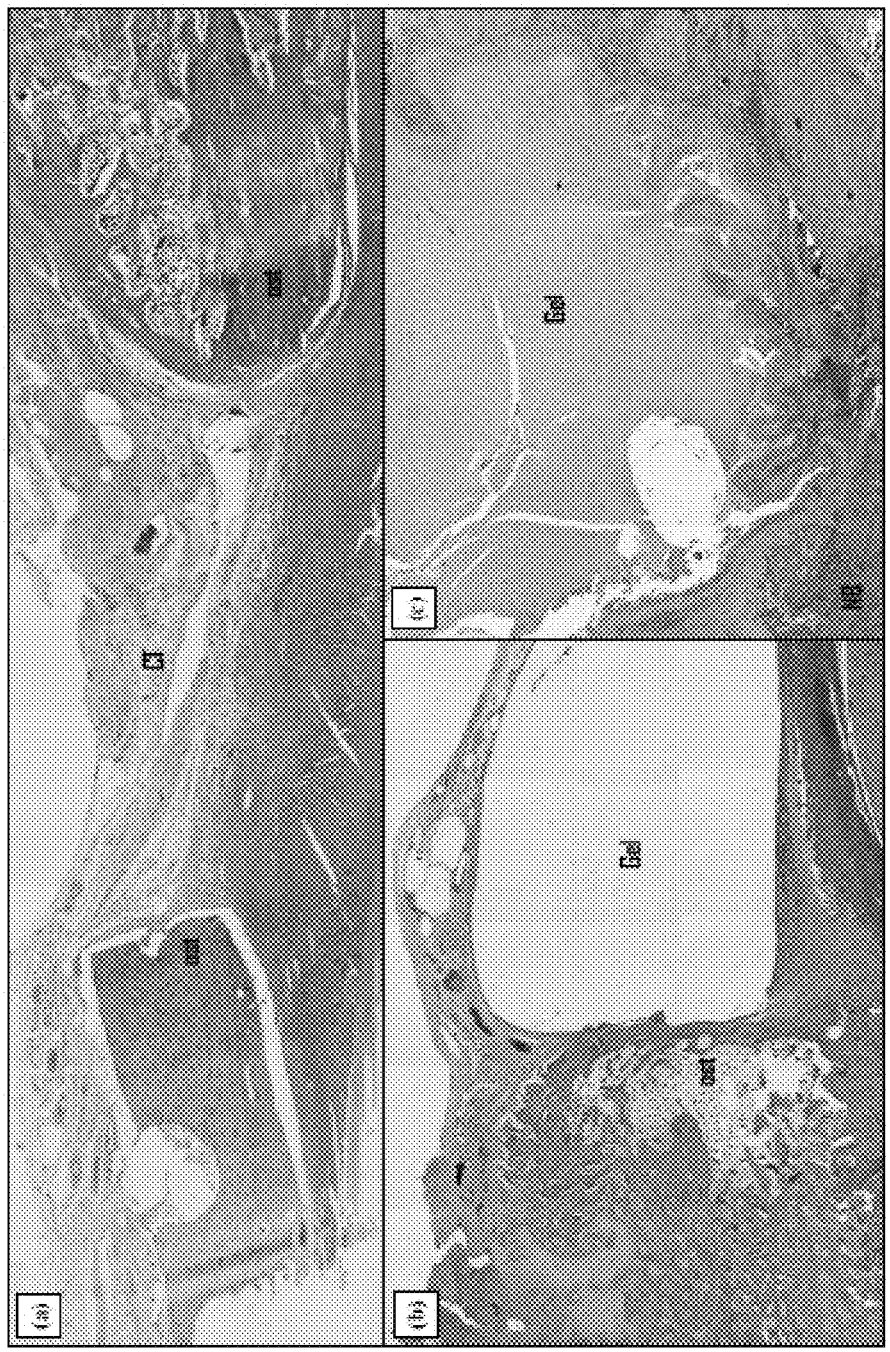
FIGs. 23a-c

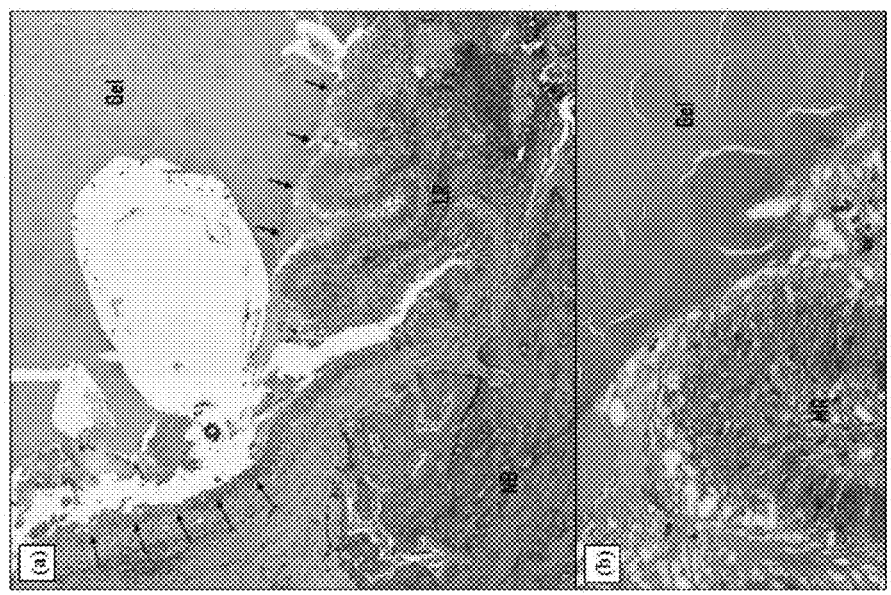
FIGs. 24a-b

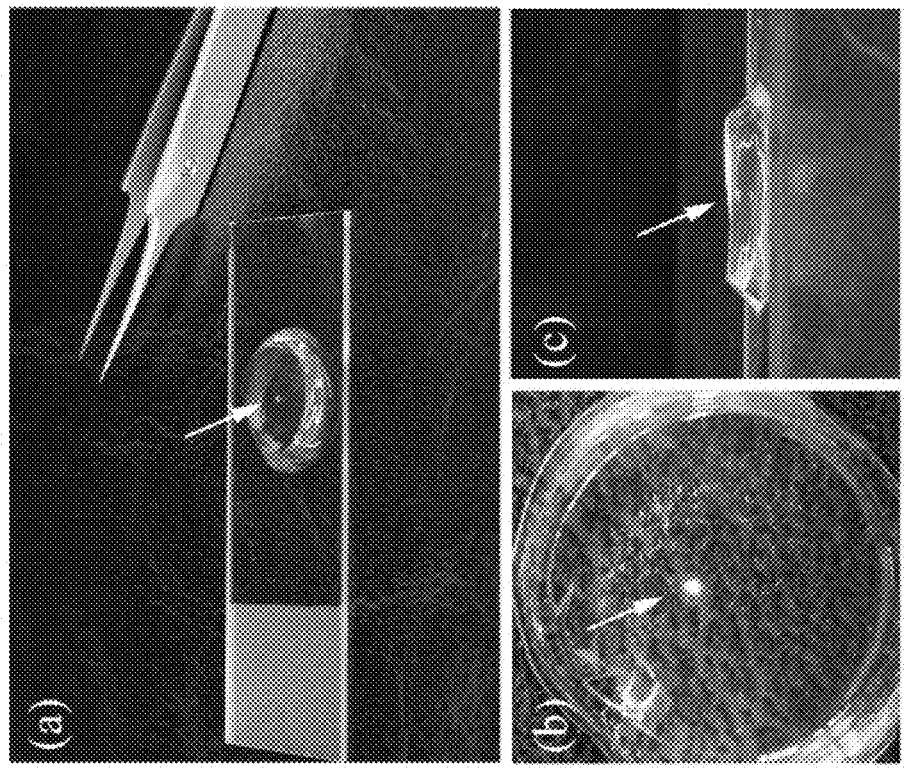
FIGs. 25a-c

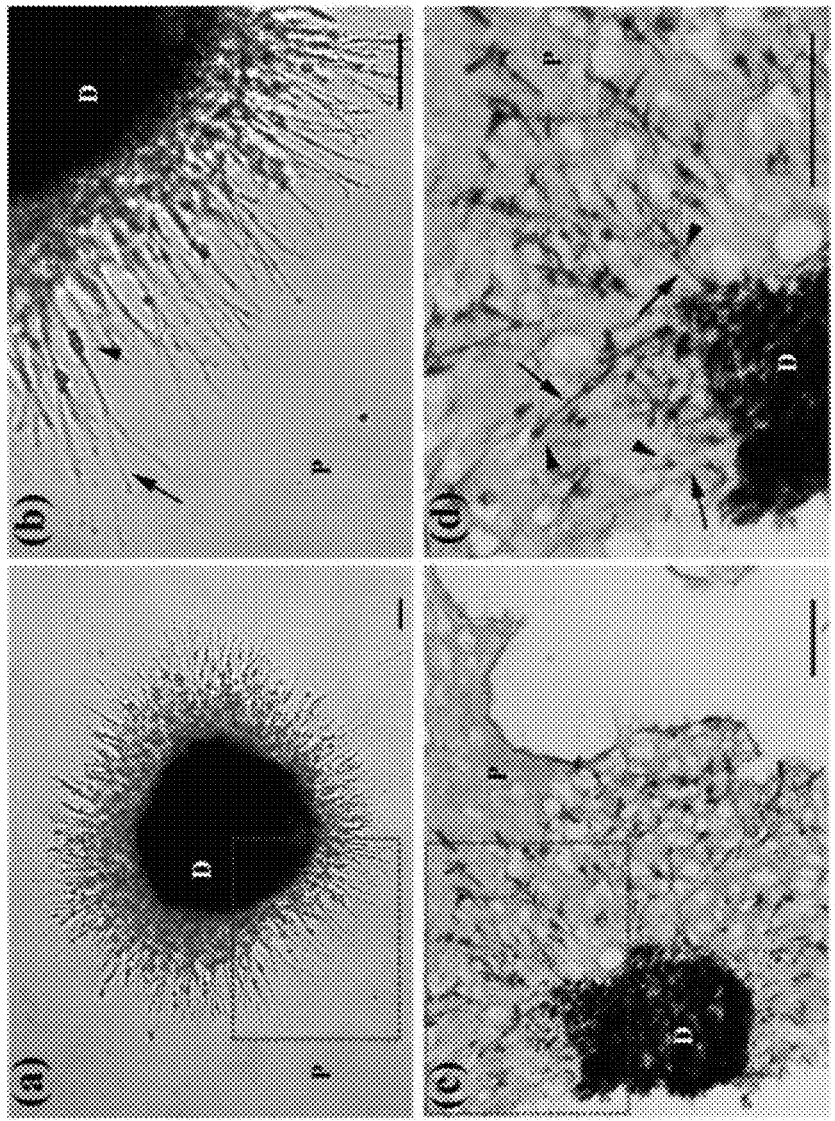
FIGs. 26a-d

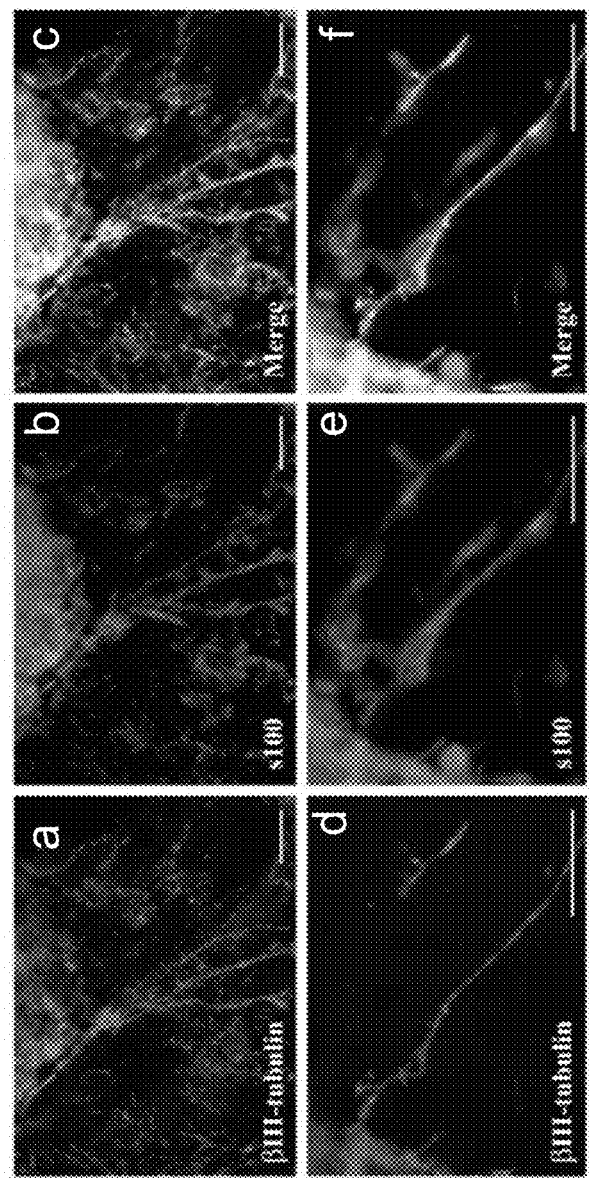
FIGs. 27a-f

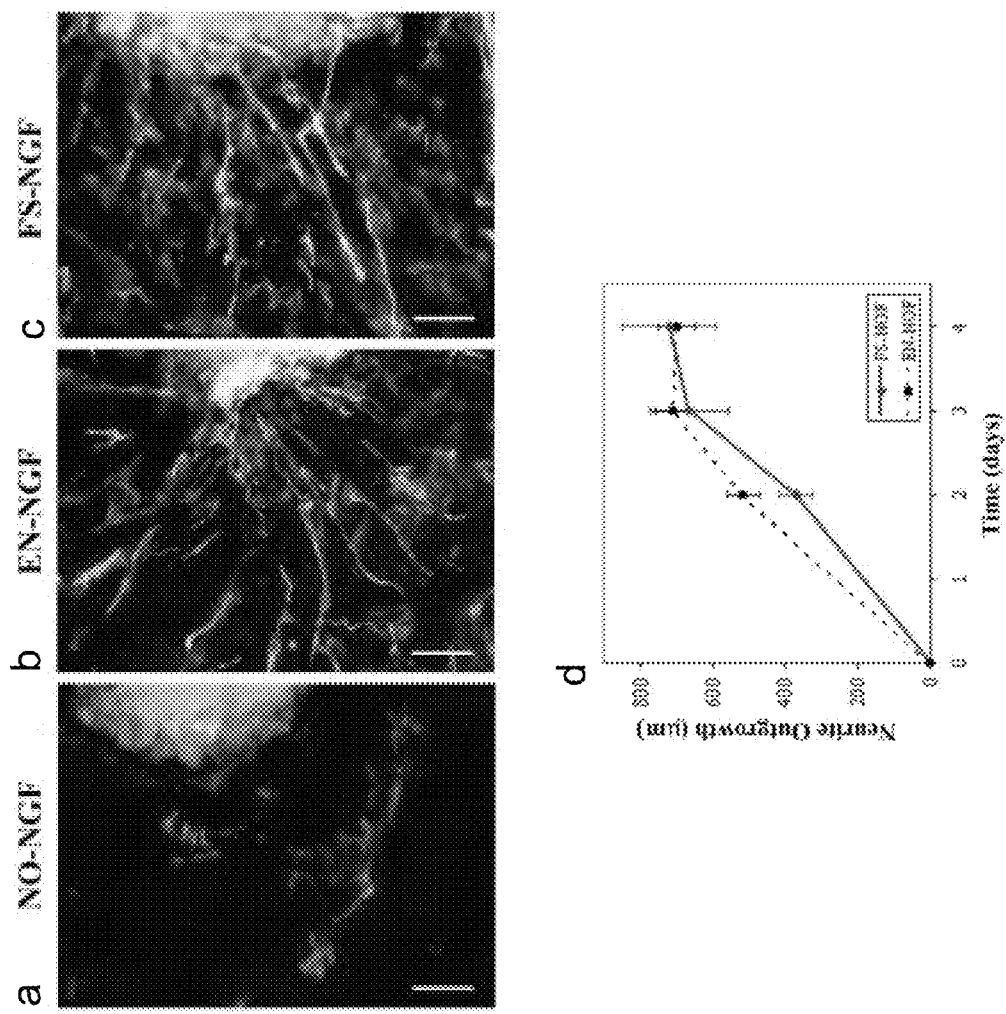
FIGs. 28a-d

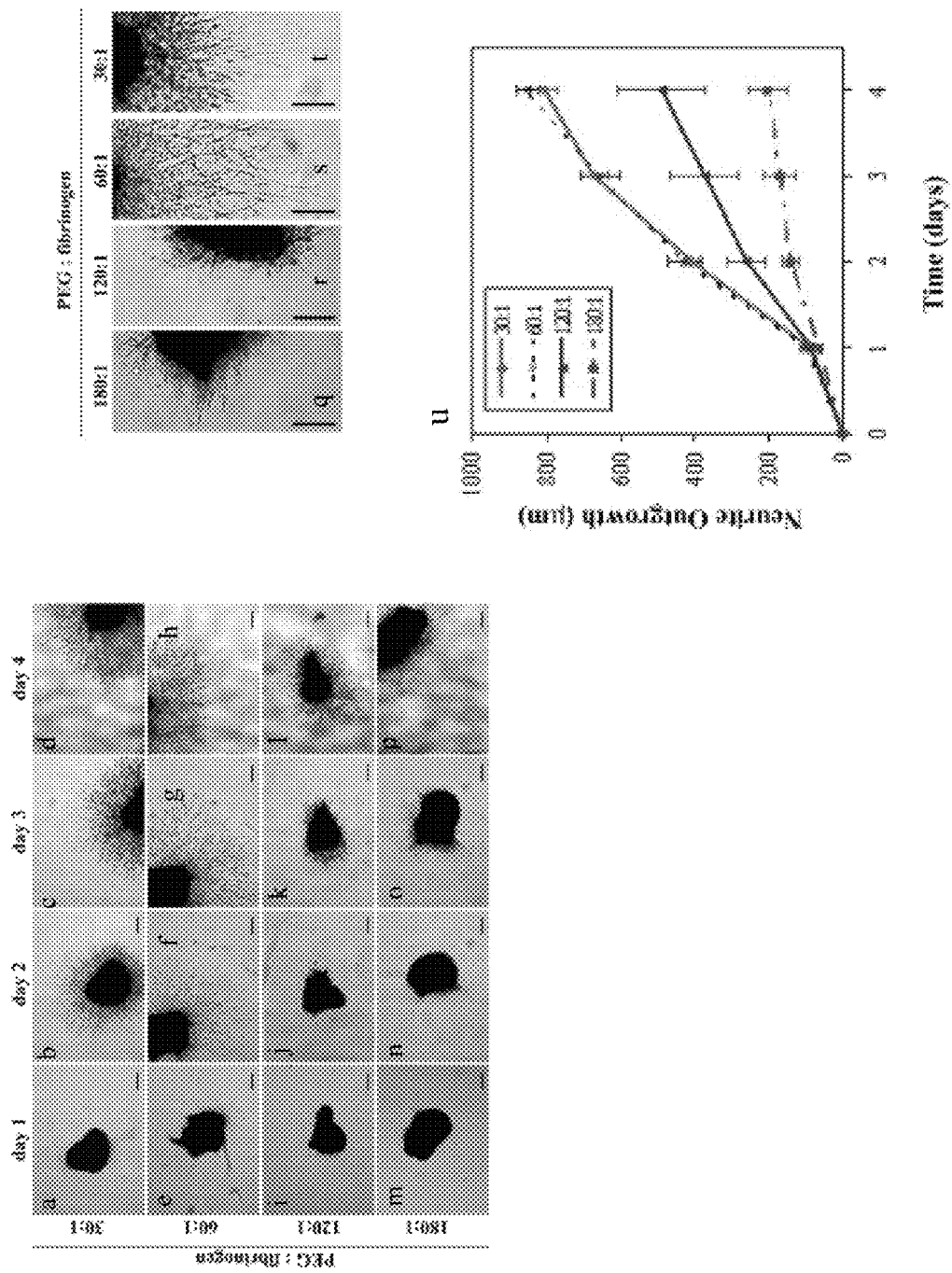
FIGs. 29a-u

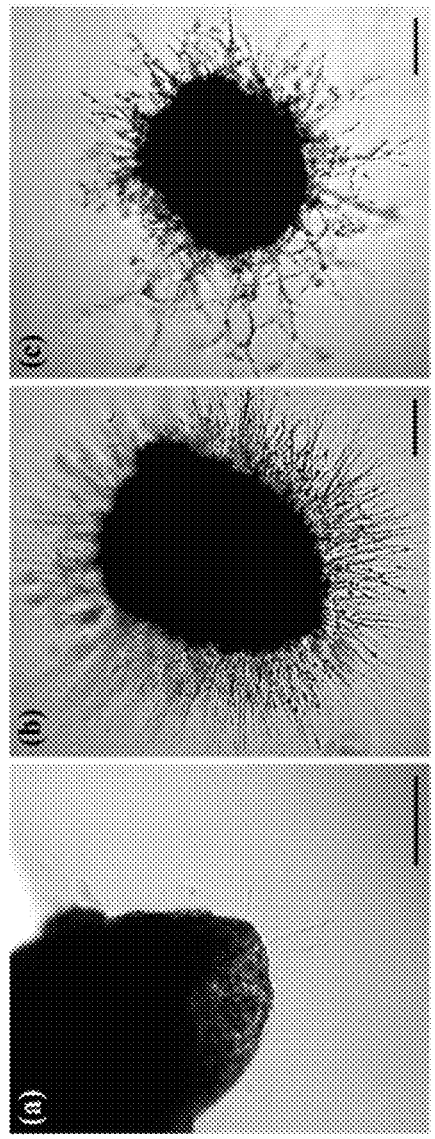
FIGs. 30a-c

PEGYLATED FIBRINOGEN PRECURSOR MOLECULE

RELATED APPLICATIONS

This application is a continuation of U.S. patent application Ser. No. 11/472,437 filed on Jun. 22, 2006, now U.S. Pat. No. 8,007,774, which is a continuation-in-part of PCT Patent Application No. PCT/IL2004/001136 having International filing date of Dec. 15, 2004, which claims the benefit of priority of U.S. Provisional Patent Application No. 60/530,917 filed on Dec. 22, 2003. The contents of the above applications are all incorporated herein by reference.

FIELD AND BACKGROUND OF THE INVENTION

The present invention relates to a matrix composed of a naturally-occurring protein backbone cross-linked by polyethylene glycol (PEG) and, more particularly, to methods of generating and using same in tissue regeneration.

Tissue engineering, i.e., the generation of new living tissues in vitro, is widely used to replace diseased, traumatized or other unhealthy tissues. The classic tissue engineering approach utilizes living cells and a basic scaffold for cell culture (Langer and Vacanti, 1993; Nerem and Seliktar, 2001). Thus, the scaffold structure attempts to mimic the natural structure of the tissue it is replacing and to provide a temporary functional support for the cells (Griffith L G, 2002).

Tissue engineering scaffolds are fabricated from either biological materials or synthetic polymers. Synthetic polymers such as polyethylene glycol (PEG), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE) provide precise control over the mechanical properties of the material (Drury and Mooney, 2003).

Common scaffold fabrication methods are based on foams of synthetic polymers. However, cell migration into the depth of synthetic scaffolds is limited by the lack of oxygen and nutrient supply. To overcome such limitations, new approaches utilizing solid freeform fabrications and internal vascular architecture have been developed (Reviewed in Sachlos E and Czernuszka J T, 2003; Eur. Cell Mater. 5: 29-39). Likewise, freeze-drying methods are also employed to create unique three-dimensional architectures with distinct porosity and permeability. However, creating pores into these materials is an aggressive procedure involving the use of toxic reagents which eliminate the possibility of pre-casting tissue constructs with living cells. Therefore, many of the prefabricated materials are subject to uneven cell seeding and non-homogeneous populations of cells within the constructs. Furthermore, the materials are generally degraded unevenly during the tissue cultivation process, creating a highly anisotropic tissue with altered growth kinetics.

Scaffolds made of PEG are highly biocompatible (Merrill and Salzman, 1983) and exhibit versatile physical characteristics based on their weight percent, molecular chain length, and cross-linking density (Temenoff J S et al., 2002). In addition, PEG hydrogels are capable of a controlled liquid-to-solid transition (gelation) in the presence of cell suspension (Elbert and Hubbell, 2001). Moreover, the PEG gelation (i.e., PEGylation) reaction can be carried out under non-toxic conditions in the presence of a photoinitiator (Elisseeff J et al., 2000; Nguyen and West, 2002) or by mixing a two-part reactive solution of functionalized PEG and cross-linking constituents (Lutolf and Hubbell, 2003).

However, while the abovementioned synthetic polymers enable precise control over the scaffold material, they often provide inadequate biological information for cell culture. As a result, these materials are unsuitable for long-term tissue culture or in vivo tissue regeneration.

On the other hand, naturally occurring scaffolds such as collagen, fibrin, alginate, hyaluronic acid, gelatin, and bacterial cellulose (BC) provide bio-functional signals and exhibit various cellular interactions. For example, fibrin, a natural substrate of tissue remodeling (Herrick S., et al., 1999), contains several cell-signaling domains such as a protease degradation substrate (Werb Z, 1999) and cell-adhesion domains (Herrick S., 1999). However, because such biological materials exhibit multiple inherent signals (e.g., regulation of cell adhesion, proliferation, cellular phenotype, matrix production and enzyme activity), their use as scaffolds in tissue regeneration often results in abnormal regulation of cellular events (Hubbell, 2003). Furthermore, the natural scaffolds are often much weaker after reconstitution as compared to the strength of the original biological material, and little control can be exercised to improve their physical properties.

Therefore, the ideal scaffold for tissue engineering should exhibit the structural characteristics of synthetic materials with the biofunctionality of natural materials (Leach J B, et al., 2004; Leach and Schmidt, 2005). To this end, several methods of preparing scaffold with natural biofunctionality and physical properties of synthetic polymers have been proposed. Most of these "hybrid" approaches, however, fall short of producing a biomaterial with broad inherent biofunctionality and a wide range of physical properties; mainly because they employ only a single biofunctional element into the material design. For example, prior studies describe the preparation of scaffolds consisting of biodegradable elements grafted into the backbone of a synthetic hydrogel network. Hydrogels were prepared from synthetic PEG which was cross-linked with short oligopeptides containing enzymatic substrates capable of being proteolytically degraded by cell-secreted enzymes [Lutolf et al (2003); Gobin and West (2002)]. Furthermore, to increase the biofunctionality of such hydrogels, synthetic adhesion motifs such as the RGD sequences [Lutolf et al (2003)] or VEGF (Seliktar et al; 2004, Zisch A H, et al, 2003; FASEB J. 17: 2260-2. Epub 2003 Oct. 16) were grafted into the PEG backbone. However, the use of such scaffolds (in which PEG is the major component) was limited by the insufficient bio-feedback and/or long-term cellular responses which are essential for phenotypic stability.

Further attempts to increase the biofunctionality of the scaffolds included the manufacture of genetically-engineered protein-like precursors of 100 amino acids, which contain, among other things, several protease substrates and adhesion sites (Halstenberg et al. 2002; Biomacromolecules, 3: 710-23). However, the increased protein precursors size and the presence of thiol groups required for the PEGylation reaction complicated the purification and solubilization of the precursors during the scaffold manufacturing process. In addition, similar to the PEG-based biosynthetic materials, the genetically-engineered protein precursor scaffolds failed to provide sufficient biofunctionality to enable long-term stability.

There is thus a wide recognized need for and it would be highly advantageous to have biodegradable scaffolds for pomoting tissue regeneration, which are devoid of the above-limitations.

SUMMARY OF THE INVENTION

According to one aspect of the present invention there is provided a composition-of-matter comprising a naturally occurring protein or a bioactive fragment of the protein and at least two synthetic polymers covalently connected thereto, each of the at least two synthetic polymers having a functional group being capable of covalently attaching to a synthetic polymer of the at least two synthetic polymers so as to form a scaffold.

According to another aspect of the present invention there is provided a scaffold formed by cross-linking the composition-of-matter.

According to yet another aspect of the present invention there is provided a scaffold comprising a plurality of protein molecules covalently attached therebetween so as to form the scaffold via a synthetic polymer having a first part and a second part covalently attached therebetween via a chemical moiety being chemically distinct from a repeating unit of the polymer.

According to further features in preferred embodiments of the invention described below, the scaffold is biodegradable.

According to still further features in the described preferred embodiments the synthetic polymer is selected from the group consisting of polyethylene glycol (PEG), Hydroxyapatite/polycaprolactone (HA/PLC), polyglycolic acid (PGA), Poly-L-lactic acid (PLLA), Polymethyl methacrylate (PMMA), polyhydroxyalkanoate (PHA), poly-4-hydroxybutyrate (P4HB), polypropylene fumarate (PPF), polyethylene glycol-dimethacrylate (PEG-DMA), beta-tricalcium phosphate (beta-TCP) and nonbiodegradable polytetrafluoroethylene (PTFE).

According to still further features in the described preferred embodiments the naturally occurring protein is selected from the group consisting of a cell signaling protein, an extracellular matrix protein, a cell adhesion protein, a growth factor and a protease.

According to still further features in the described preferred embodiments the cell signaling protein is selected from the group consisting of p38 mitogen-activated protein kinase, nuclear factor kappaB, Raf kinase inhibitor protein (RKIP), Raf-1, MEK, Protein kinase C(PKC), phosphoinositide-3-kinase gamma, receptor tyrosine kinases (e.g., insulin receptor), heterotrimeric G-proteins [e.g., Galpha(i), Galpha(s) and Galpha(q)], Caveolin-3, and 14-3-3 proteins.

According to still further features in the described preferred embodiments the extracellular matrix protein is selected from the group consisting of fibrinogen, Collagen, fibronectin, vimentin, microtubule-associated protein 1D, Neurite outgrowth factor (NOF), bacterial cellulose (BC), laminin and gelatin.

According to still further features in the described preferred embodiments the cell adhesion protein is selected from the group consisting of integrin, intercellular adhesion molecule (ICAM) 1, N-CAM, cadherin, tenascin, gicerin, and nerve injury induced protein 2 (ninjurin2).

According to still further features in the described preferred embodiments the growth factor is selected from the group consisting of epidermal growth factor, transforming growth factor-α, fibroblast growth factor-acidic, fibroblast growth factor-basic, erythropoietin, thrombopoietin, hepatocyte growth factor, insulin-like growth factor-I, insulin-like growth factor-II, Interferon-β, and platelet-derived growth factor.

According to still further features in the described preferred embodiments the protease protein is selected from the group consisting of pepsin, low specificity chymotrypsin, high specificity chymotrypsin, trypsin, carboxypeptidases, aminopeptidases, proline-endopeptidase, *Staphylococcus aureus* V8 protease, Proteinase K (PK), aspartic protease, serine proteases, metalloproteases, ADAMTS17, tryptase-gamma, and matriptase-4.1.

According to still further features in the described preferred embodiments the PEG is selected from the group consisting of PEG-acrylate (PEG-Ac) and PEG-vinylsulfone (PEG-VS).

According to still further features in the described preferred embodiments the PEG-Ac is selected from the group consisting of PEG-DA, 4-arm star PEG multi-Acrylate and 8-arm star PEG multi-Acrylate.

According to still further features in the described preferred embodiments the PEG-DA is a 4-kDa PEG-DA, 6-kDa PEG-DA, 10-kDa PEG-DA and/or 20-kDa PEG-DA.

According to still further features in the described preferred embodiments the synthetic polymer is PEG and whereas the naturally occurring protein is fibrinogen.

31 According to still further features in the described preferred embodiments the PEG is selected from the group consisting of PEG-DA, 4-arm star PEG multi-Acrylate and 8-arm star PEG multi-Acrylate.

According to still further features in the described preferred embodiments the PEG-DA is a 4-kDa PEG-DA, 6-kDa PEG-DA, 10-kDa PEG-DA and/or 20-kDa PEG-DA.

According to still further features in the described preferred embodiments the fibrinogen is denatured.

According to still further features in the described preferred embodiments a molar ratio between the PEG-DA to the fibrinogen in the units is 2-400 to 1, respectively.

According to still further features in the described preferred embodiments a concentration of PEG-DA is 3% w/v.

According to still further features in the described preferred embodiments the scaffold further comprising a growth factor.

According to still further features in the described preferred embodiments the growth factor is NGF.

According to still further features in the described preferred embodiments the fibrinogen is whole fibrinogen or fragmented fibrinogen.

According to still further features in the described preferred embodiments the scaffold does not comprise more than 10% unconjugated form of the syntheric polymer.

According to still further features in the described preferred embodiments the chemical moiety is selected from the group consisting of aldehydes, acetale, tosyl, tresyl, dichlorotriazine, epoxide, carboxylic, succinimidyle succinate, succinimidyl ester, p-nitrophenyl carbonate, benzotriazolyl carbonate, 2,3,5-trichlorophenyl carbonate, succinimidyle carbonate, pyridildisulphide, maleimide, vinylsulfone, and iodo acetamide.

According to still another aspect of the present invention there is provided a hydrogel formed from the scaffold.

According to still further features in the described preferred embodiments the naturally occurring protein is whole fibrinogen and whereas a concentration of the units in the hydrogel is selected from a range of 0.5-35%.

According to still further features in the described preferred embodiments the fibrinogen is fragmented fibrinogen and whereas a concentration of the units in the hydrogel is selected from a range of 0.5-35%.

According to still further features in the described preferred embodiments modulus of elasticity of the hydrogel is in a range of 0.02-0.11 kPa for 10-20% polymer.

According to still further features in the described preferred embodiments modulus of elasticity of the hydrogel is in a range of 0.01-0.07 kPa for 10-20% polymer.

According to an additional aspect of the present invention there is provided a method of generating a scaffold comprising:

(a) covalently attaching a naturally occurring protein or a bioactive fragment of the protein to at least two synthetic polymer through a first functional group, each of the at least two synthetic polymers having a second functional group to thereby obtain a polymer-protein precursor molecule; and subsequently (b) cross-linking a plurality of the precursor molecules to thereby generate the scaffold.

According to still further features in the described preferred embodiments the first and second functional groups are identical.

According to still further features in the described preferred embodiments the method further comprising removing unconjugated form of the synheric polymer prior to step b.

According to yet an additional aspect of the present invention there is provided a method of inducing in vivo formation of a tissue, the method comprising implanting the scaffold in a subject to thereby induce the formation of the tissue.

According to still an additional aspect of the present invention there is provided a method of inducing ex-vivo formation of a tissue, the method comprising:

(a) providing the scaffold; and (b) seeding the scaffold with cells to thereby induce tissue formation.

According to a further aspect of the present invention there is provided a method of inducing in vivo formation of a tissue, the method comprising administering to a subject in need thereof the composition-of-matter, the composition being capable of forming the scaffold within the subject, thereby inducing the formation of the tissue in vivo.

According to a further aspect of the present invention there is provided a method of treating a subject having a disorder characterized by tissue damage or loss, the method comprising:

(a) providing the scaffold; and (b) implanting the scaffold in the subject to thereby induce formation of the tissue and treat the disorder characterized by tissue damage or loss.

According to yet a further aspect of the present invention there is provided a method of treating a subject having a disorder characterized by tissue damage or loss, the method comprising:

(a) providing the scaffold; and (b) seeding the scaffold with cells, and;

(c) implanting the scaffold in the subject to thereby induce formation of the tissue and treat the disorder characterized by tissue damage or loss.

According to still a further aspect of the present invention there is provided a method of treating a subject having a disorder characterized by tissue damage or loss, the method comprising administering to the subject the composition of-matter, the composition being capable of forming a scaffold within the subject, thereby inducing a formation of a tissue and treating the disorder characterized by tissue damage or loss.

According to still a further aspect of the present invention there is provided a composition-of-matter comprising a functional polyethylene glycol (PEG) attached to denatured fibrinogen or a bioactive fragment of the protein.

According to still a further aspect of the present invention there is provided a kit for inducing tissue regeneration, the kit comprising a packaging material which comprises the composition-of-matter.

According to still a further aspect of the present invention there is provided a kit for inducing tissue regeneration, the kit comprising a packaging material which comprises the scaffold.

The present invention successfully addresses the shortcomings of the presently known configurations by providing biodegradable scaffold suitable for tissue regeneration applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 1A, 1B:
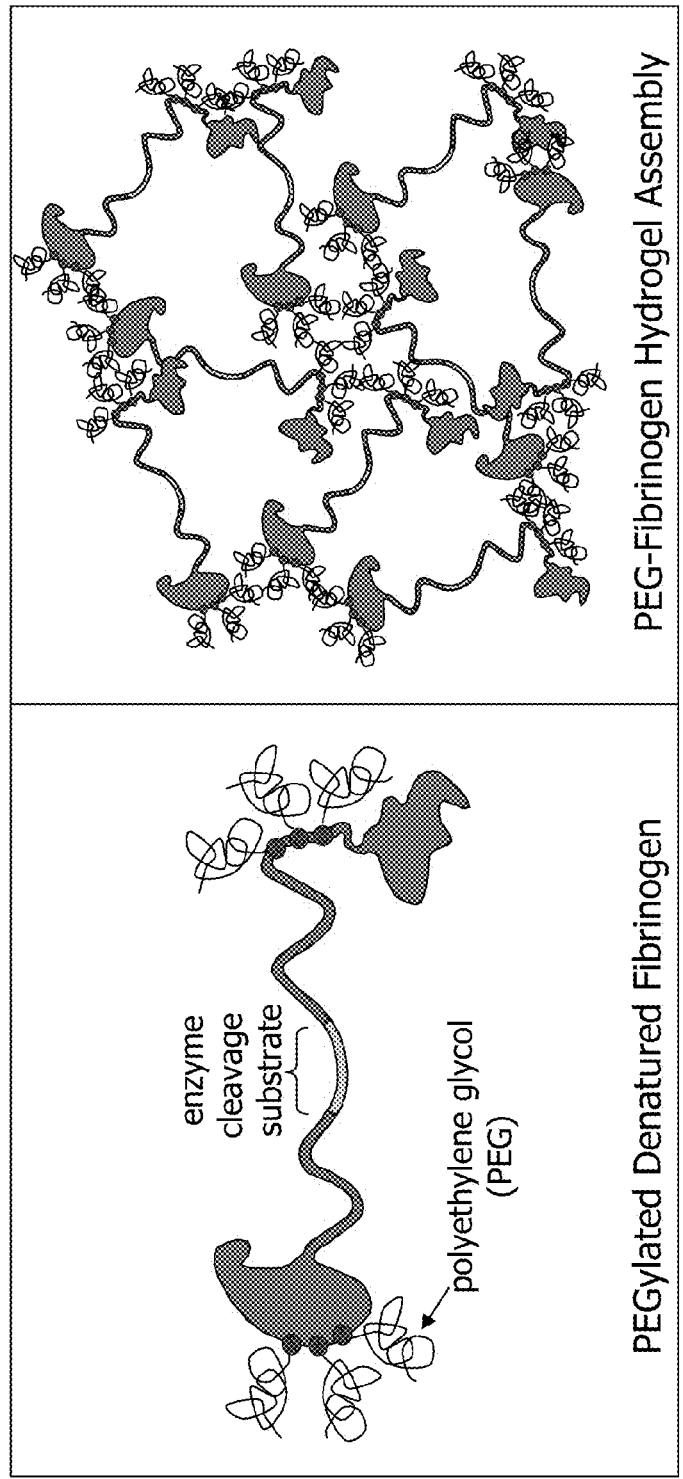

FIGS. 1a-b are schematic illustrations of the PEG-fibrinogen hydrogel assembly. FIG. 1a—PEGylated fibrinogen fragments contain a natural protease cleavage site (yellow) and multiple unpaired thiol groups (red) for covalent conjugation of functionalized PEG by Michael-type addition reaction. FIG. 1b—PEG-fibrinogen hydrogel assembly is accomplished by covalent cross-linking of unreacted PEG-acrylates to one another, resulting in a hydrogel network of PEGylated fibrinogen. The cross-linking reaction can be accomplished by free-radical polymerization in the presence of very small quantities of photoinitiator and low-power light.

Figure 2B:
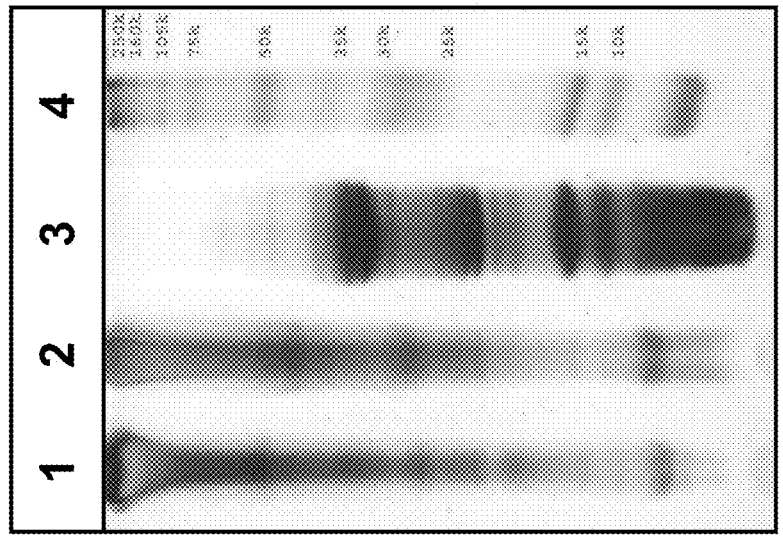
Figure 2A:
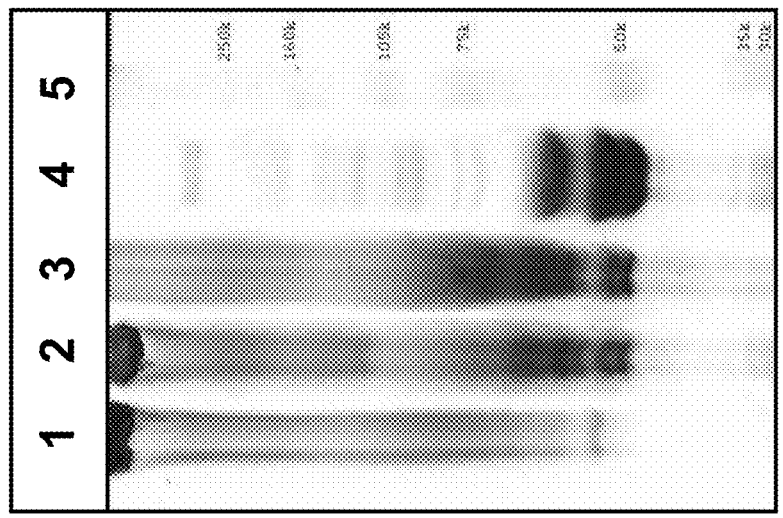

FIGS. 2a-b are Coomassie®-blue staining of SDS-PAGE gels illustrating PEGylated and un-PEGylated Fibrinogen Fragments before and after PEGylation with functionalized PEG. FIG. 2a—Electrophoresis of PEGylated whole fibrinogen in 10% SDS-PAGE. Fibrinogen was incubated with either 4-kDa linear fractionalized PEG di-acrylate (PEG-DA; lanes 1-3) or with PEG-OH (4 kDa, lane 4). Note the presence of the α-chains (63.5-kDa), β-chains (56-kDa), and γ-chains (47-kDa) of fibrinogen in the presence of PEG-OH following 12 hours of incubation (lane 4) and the progressive retardation of the protein fragment in the acrylamide gel following the incubation with 4-kDa linear functionalized PEG for 1 hour (lane 3), 2 hours (lane 2) or overnight (lane 1). Lane 5—molecular weight marker (BIO-RAD SDS-PAGE molecular weight standards, Broad range: 200,000-6,000 Da); FIG. 2b—Electrophoresis of PEGylated cyanogen bromide (CNBr)—cleaved fibrinogen fragments in 20% SDS-PAGE. Fibrinogen was treated with CNBr for 12 hours as described under Materials and Experimental Methods of Example 1 of the Examples section which follows and the cleaved fibrinogen fragments were incubated for 1 hour in the presence (lanes 1 and 2) or absence (lane 3) of linear fractionalized PEG-DA. Note the highly PEGylated fibrinogen species (i.e., the high molecular weight fragments) present following 1 hour incubation with linear PEG-DA 6-kDa (lane 1) and 4-kDa (lane 2). Lane 4—molecular weight marker.

Figures 3A, 3B:
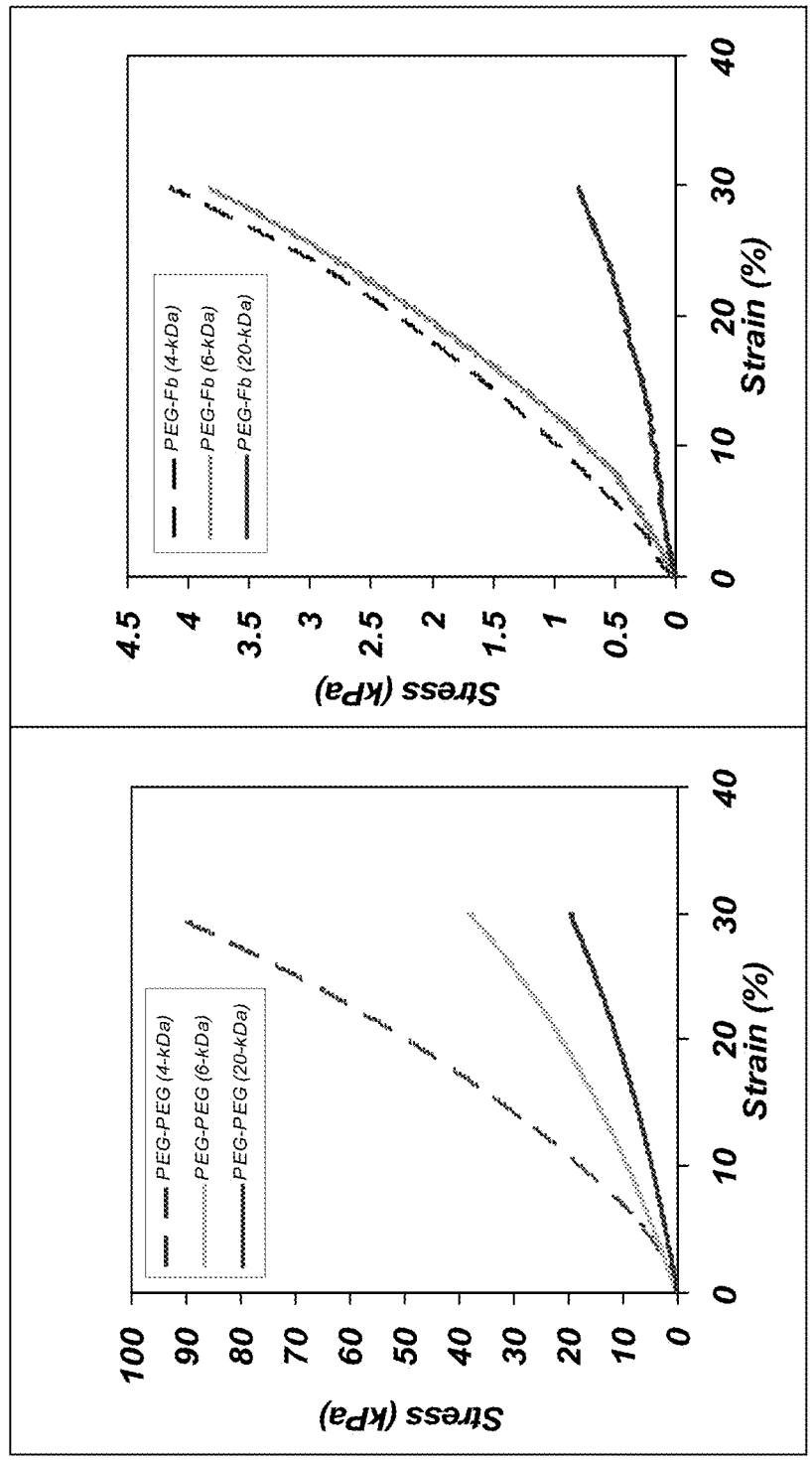

FIGS. 3a-b are graphs illustrating stress-strain characteristics of PEG-based hydrogels. The slope of the stress-strain curve represents the modulus of the material. The dependency of the modulus [expressed in units of kilo Pascal (kPa)] on the length of PEG used was measured using an Instron™ 5544 single column material testing system with the Merlin software (www.instron.com). FIG. 3a-behavior of 20% polymer (w/v) PEG-PEG hydrogels; FIG. 3b—behavior of PEG-fibrinogen hydrogels. Note that material properties (modulus) are dependent on the molecular weight of the PEG (FIG. 3a). Also note that while in the PEG-PEG hydrogels the modulus of the hydrogel is directly proportional to molecular weight of the PEG (FIG. 3a), in the PEG-fibrinogen hydrogels similar modulus values were observed using the 4-kDa and the 6-kDa PEG. Aside from this exception, the stress-strain behavior of the PEG-fibrinogen hydrogels was identical to that of PEG-only controls.

Figure 4A:
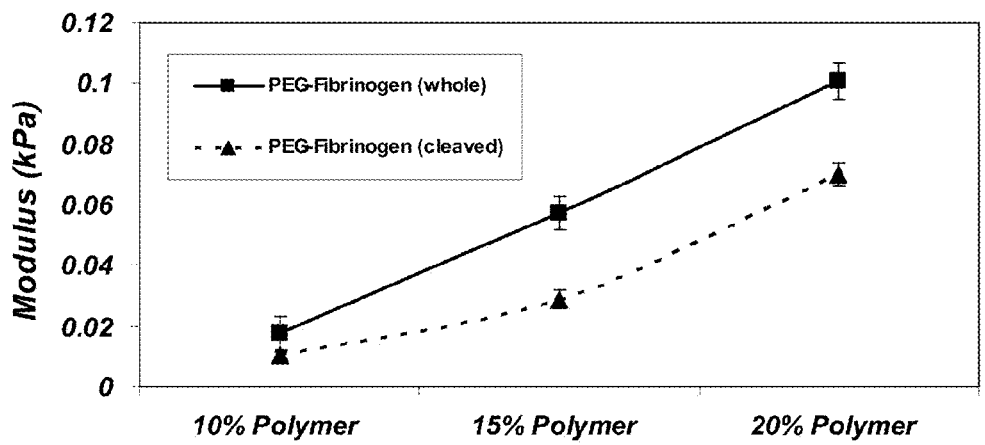
Figure 4B:
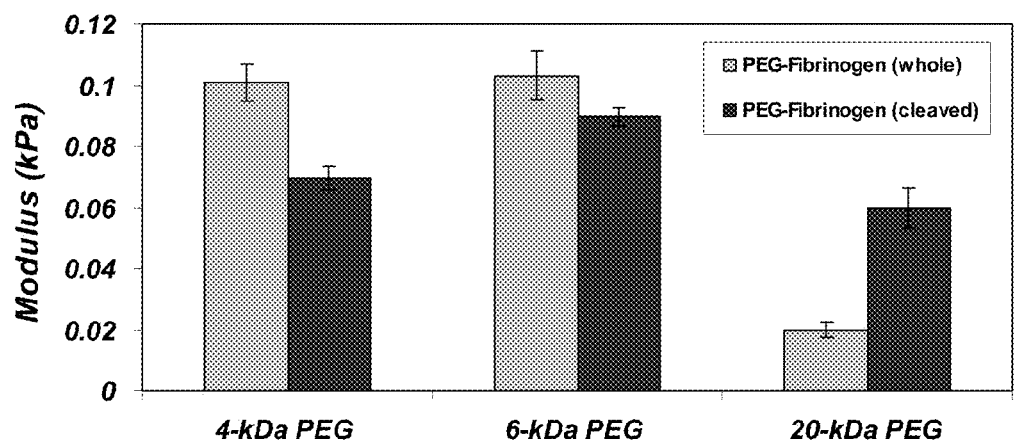
Figure 4C:
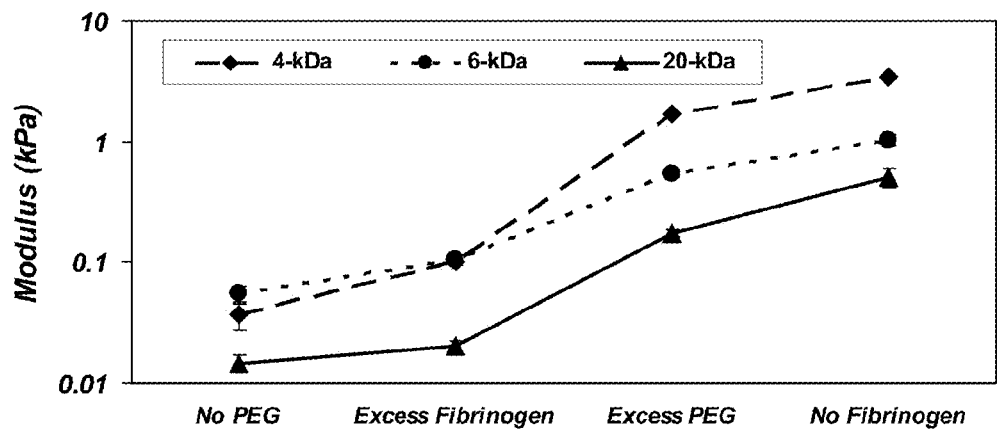

FIGS. 4a-c are graphs illustrating the ability to manipulate the mechanical properties of the PEG-fibrinogen hydrogels by altering the percent of polymer used (FIG. 4a), the PEG molecular weight used (FIG. 4b) and the polymer/protein composition (FIG. 4c). Introduction of variations in these parameters enables the generation of hydrogels with a broad range of properties, including differing elastic moduli (measured in kPa). FIG. 4a shows the effect of increasing the percent polymeric composition of 4-kDa PEGylated fibrinogen on the hydrogel elastic modulus; note that the elastic modulus of PEG-fibrinogen hydrogels (cleaved and whole protein) proportionally increases with increasing percent polymeric composition (also true for 6-kDa and 20-kDa PEGylated fibrinogen hydrogels). FIG. 4b demonstrates the effect of increasing the PEG molecular weight (using 20% polymer) on the hydrogel elastic modulus; note that the molecular weight of the PEG constituent has a direct proportional effect on the elastic modulus of the hydrogels (also true for 10% and 15% PEG-fibrinogen hydrogels). FIG. 4c shows the effect of increasing the ratio of PEGylated fibrinogen to additional PEG-DA in the composition of the hydrogels (using 15% polymer and whole PEGylated fibrinogen). Note that the relative amount of PEGylated fibrinogen and free, unbound PEG-DA in the precursor solution directly impacts the stiffness of the hydrogel after the free-radical polymerization; the graph shows the increase in stiffness of the PEG-fibrinogen hydrogel as a function of the addition of free PEG-DA. Note that hydrogels made only with PEG-DA (no fibrinogen) are always stiffer in comparison to PEGylated fibrinogen hydrogels. All error bars show standard deviations from the mean.

Figure 5A:
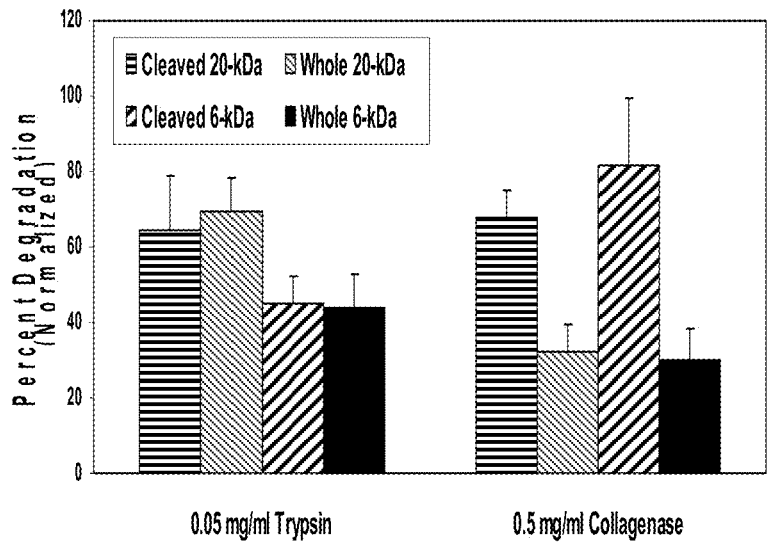
Figure 5B:
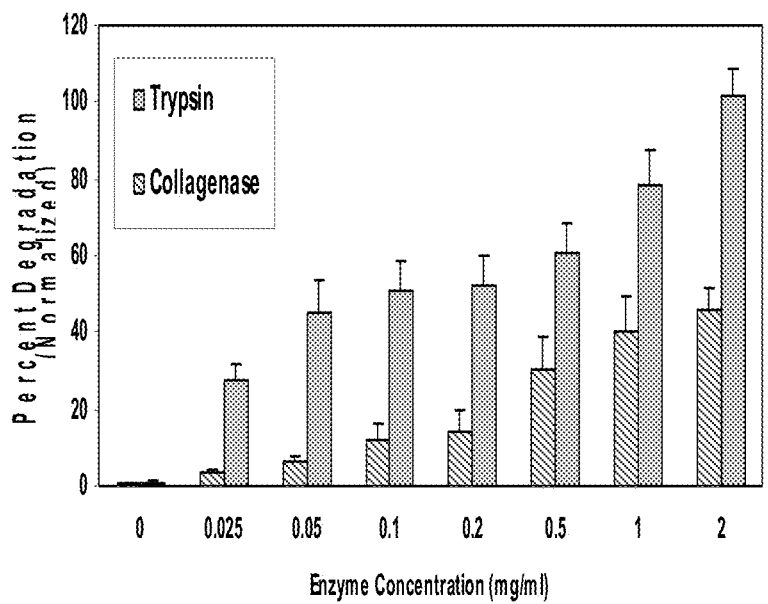

FIGS. 5a-b are graphs illustrating protease-mediated degradation of PEG-fibrinogen hydrogels. The release of colorimetric fibrinogen fragments from the hydrogels was used to assess protease-mediated degradation following 30 minutes incubation with the protease collagenase or trypsin. FIG. 5a—illustrates protease-mediated degradation in the presence of 0.5 mg/ml Collagenase or 0.05 mg/ml trypsin solution after 30 minutes incubation at 37° C. and mild agitation. Note that the amount of degradation taking place by trypsin-mediated proteolysis is significantly affected by the molecular weight of the grafted PEG constituent [i.e., more degradation in the case of the high molecular weight (20 kDa) PEG], whereas the amount of degradation taking place by Collagenase-mediated proteolysis is significantly affected by the fibrinogen constituent (i.e., more degradation in the case of cleaved fibrinogen). FIG. 5b—illustrates protease-mediated degradation as a function of the protease concentration. PEG-fibrinogen hydrogels consisting of 15% PEG (6 kDa molecular weight) and whole fibrinogen were subjected to Trypsin and Collagenase degradation as described hereinabove. Note the dose-dependent response of degradation products as a function of protease concentration. All degradation data is normalized with the colorimetric values of the fully degraded hydrogels in its respective protease solution.

FIGS. 6a-e are phase-contrast microscopic images of vascular cell cultures in PEG-based Hydrogels. FIG. 6a—A monolayer of bovine aortic endothelial cells after growing for 24 hours on a PEG-fibrinogen hydrogel surface (4-kDa PEG, 10% polymer); FIGS. 6b-c—Bovine aortic smooth muscle cells after growing three-dimensionally for 24 hours inside a PEG-fibrinogen hydrogel (4-kDa PEG, 10% polymer). Note the three-dimensional attachment and spreading of the cells in the two separate z-slices of the gel (FIGS. 6 b and c); FIG. 6d—The monolayer of bovine aortic endothelial cells as in FIG. 6a after growing for 24 hours on a PEG-PEG control hydrogel (4-kDa PEG, 10% polymer); FIG. 6e—The aortic smooth muscle cells as in FIGS. 6b-c after growing inside a PEG-PEG hydrogel (4 kDa PEG, 10%). Note the adhesion and spreading of the endothelial cells (FIG. 6a), as well as the smooth muscle cells (FIGS. 6b-c) when grown on the PEG-fibrinogen hydrogels but not in PEG-PEG control hydrogels (FIGS. 6d-e). In the absence of a proteolytic substrate in the PEG-PEG control hydrogels, note that the encapsulated smooth muscle cells are devoid of cell extensions (FIG. 6e). All images were digitally acquired at 200× magnification using a phase-contrast microscope.

FIGS. 7a-b are histological cross-sections of similar cell-seeded PEG-based hydrogels imaged in FIG. 6. Bovine aortic smooth muscle cells were cultured for 48 hours in a PEG-fibrinogen hydrogel (4 kDa PEG, 10% polymer, FIG. 7a) or a PEG-PEG control hydrogel (4 kDa, 10%); the hydrogel specimens were cut into 7-μm thick sections and stained with hematoxylin-eosin (H&E) which depicts the cell nucleus in dark purple staining. Note the spreading of cells within the gel network in the PEG-fibrinogen hydrogel (FIG. 7a) as opposed to the encapsulated cells shown within the PEG-PEG control hydrogel, which are proteolytically non-degradable.

FIGS. 8a-d are photographs illustrating the formation of critical size rat tibia defect model. FIG. 8a—illustrates the insertion of external fixation into the rat tibia; FIG. 8b—illustrates the exposure of the tibia; FIG. 8c—illustrates the excision of a 7-mm wide section of the tibia; FIG. 8d—illustrates the insertion of a 3-mm diameter precast solid Gelrin™ cylinder (which is made of the PEG-fibrinogen hydrogel of the present invention) into the defect site.

Figure 9B:
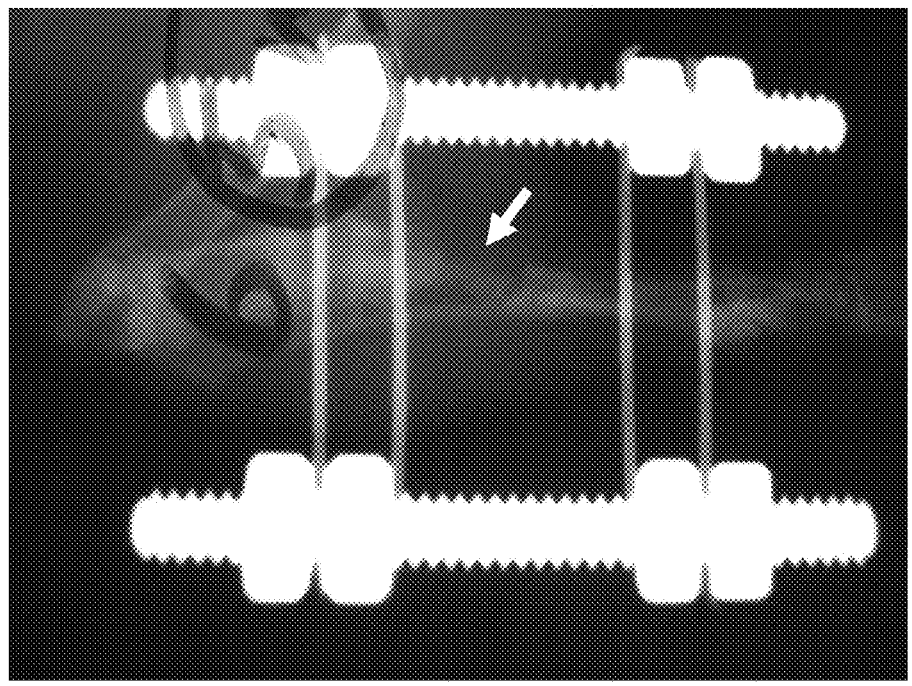
Figure 9A:
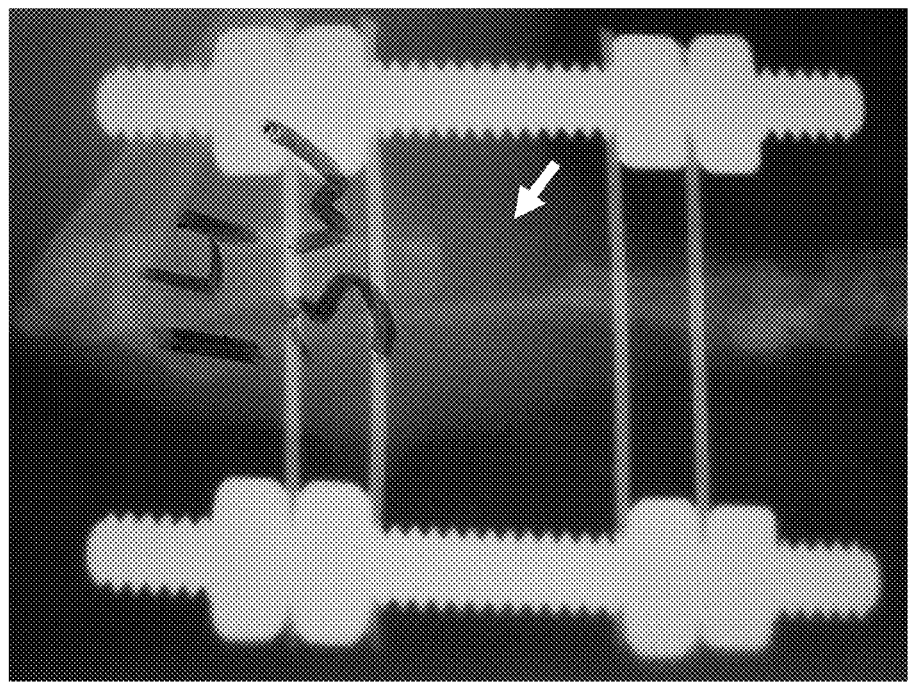

FIGS. 9a-b are x-ray images depicting the formation of new bone tissue inside the critical size rat tibia defect at 5-weeks post-operation and Gelrin™ implantation. The formation of a periosteal callus is clearly seen in the Gelrin™-treated animal (FIG. 9b, arrow) as compared with the control, untreated animal (FIG. 9a, arrow points to missing bone). Although the X-ray image of the control animal shown was taken 3-weeks post-operatively, similar results were obtained at 5 weeks post-operation (data not shown).

Figure 10:
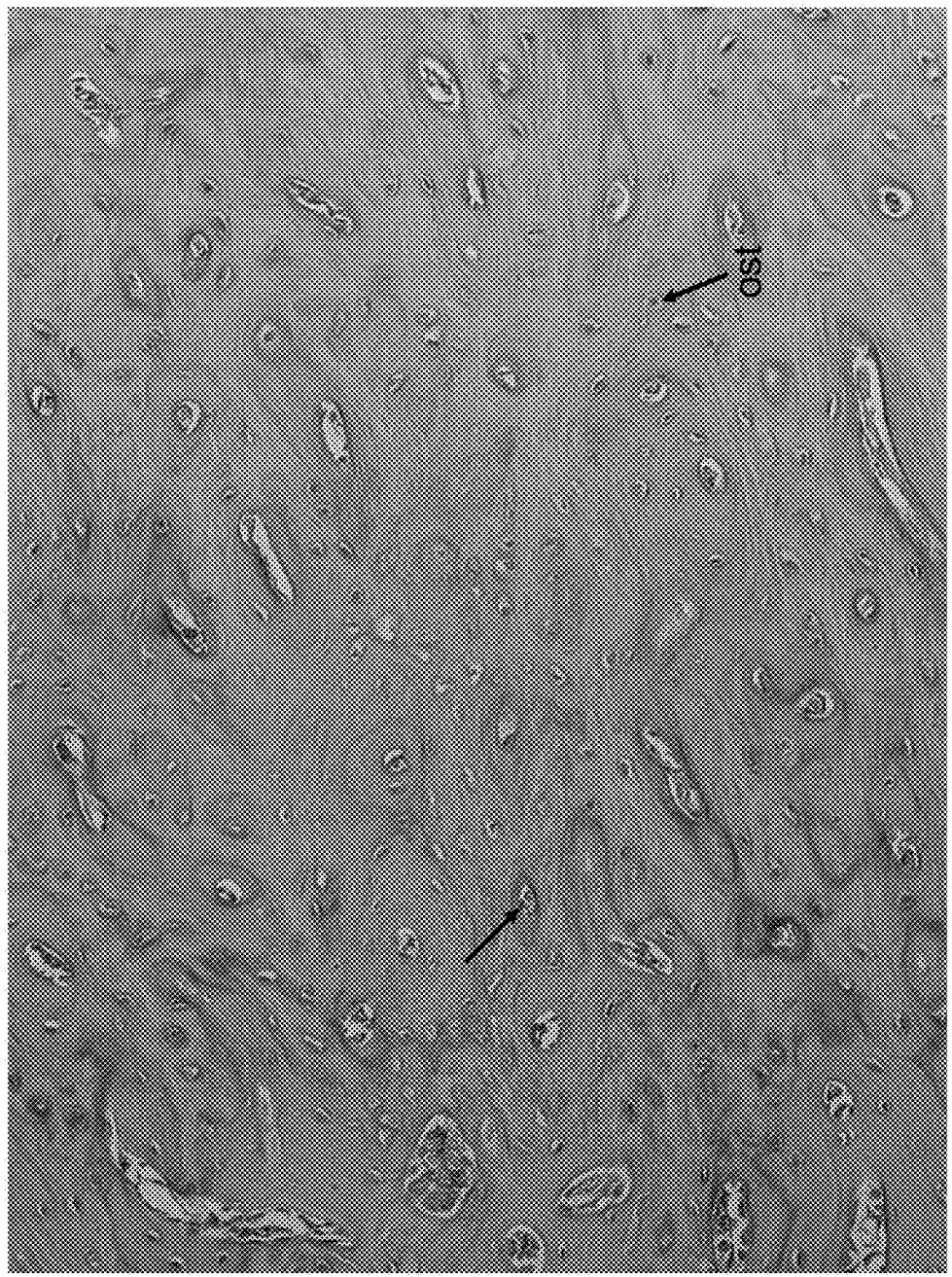

FIG. 10 is a photomicrograph of a rat tibia histological section stained with hematoxylin-eosin (H&E) showing new bone formation in the gap region of Gelrin™-implanted rat tibia at 5-weeks following the induction of a critical size defect. Note the apparently almost-normal compacta-type bone, compatible with the usual cortex of the rat bone, the Haversian systems with a small central canal containing blood vessels (small arrow), and the concentrically organized lamellae. Also note the normal osteocytes (OST), one cell to a lacunae, such that there is no indication of a recent remodeling event. Even though a polarized photomicrograph is not available, the bone appears to be everywhere lamellar-patterned.

Figure 11:
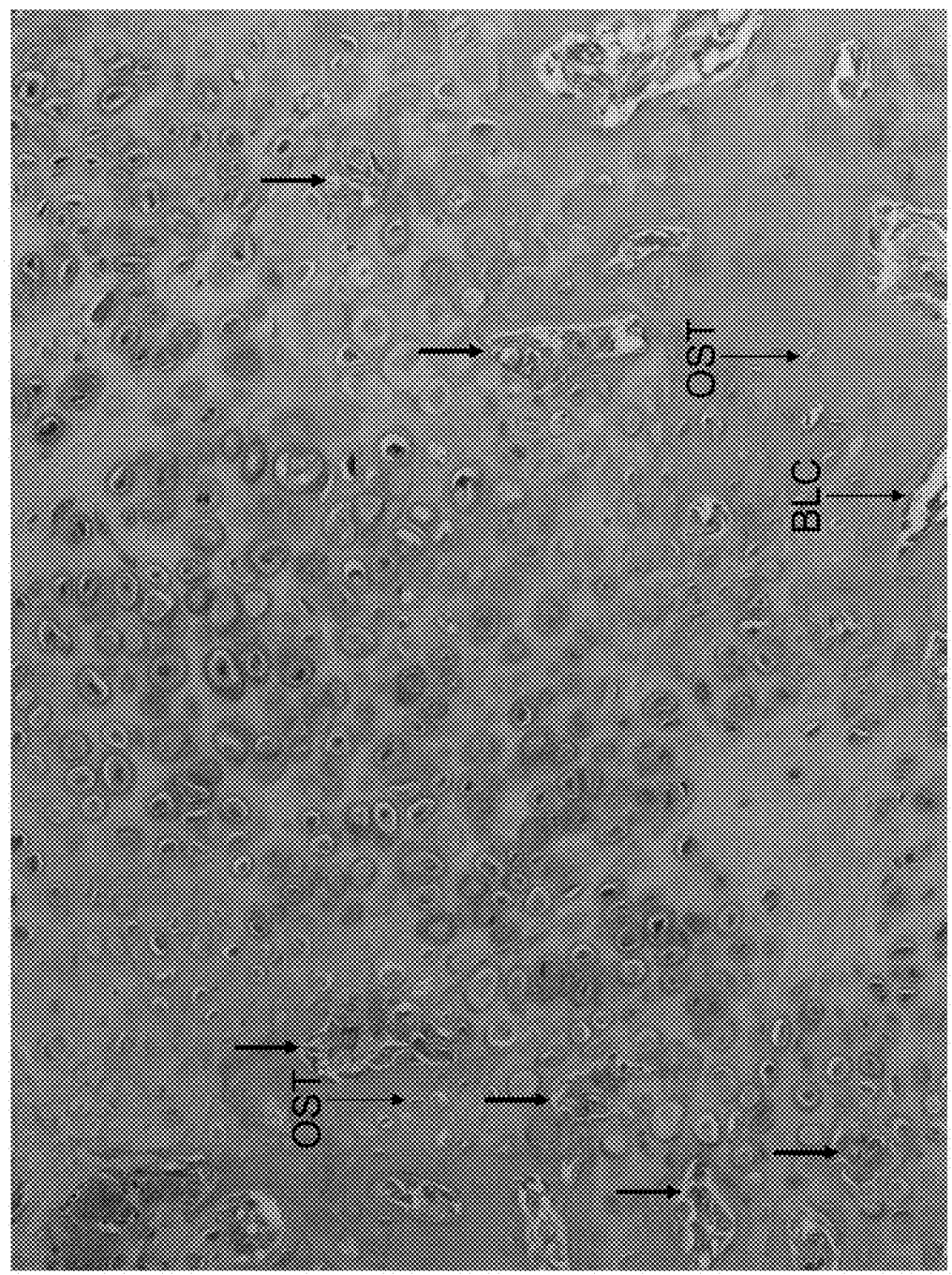

FIG. 11 is a photomicrograph of a rat tibia histological section stained with hematoxylin-eosin (H&E) showing osteonal healing with a cartilaginous island in the gap region of Gelrin™-implanted rat tibia at 5-weeks following the induction of a critical size defect. Note that while the cartilage itself is avascular, a vascular invasion is seen in the upper and lower borders of the cartilage (short arrows), indicative of endochondral ossification. Furthermore, at the upper border, the fibro-vascular tissue invading the cartilage is accompanied by cuboidal osteoblasts (OST), which indicates that the deposition of primary bone is taking place. Also note the osteoblastic rimming of the bone (evidence of ongoing osteogenesis) which is seen at the lower part, partly by cuboidal osteoblasts (OST) and partly by bone lining cells (BLC). The features in this image are characteristic of normal bone repair; the like of which one encounters in the gap of a fractured bone which has been fixated without close contact.

Figure 12:
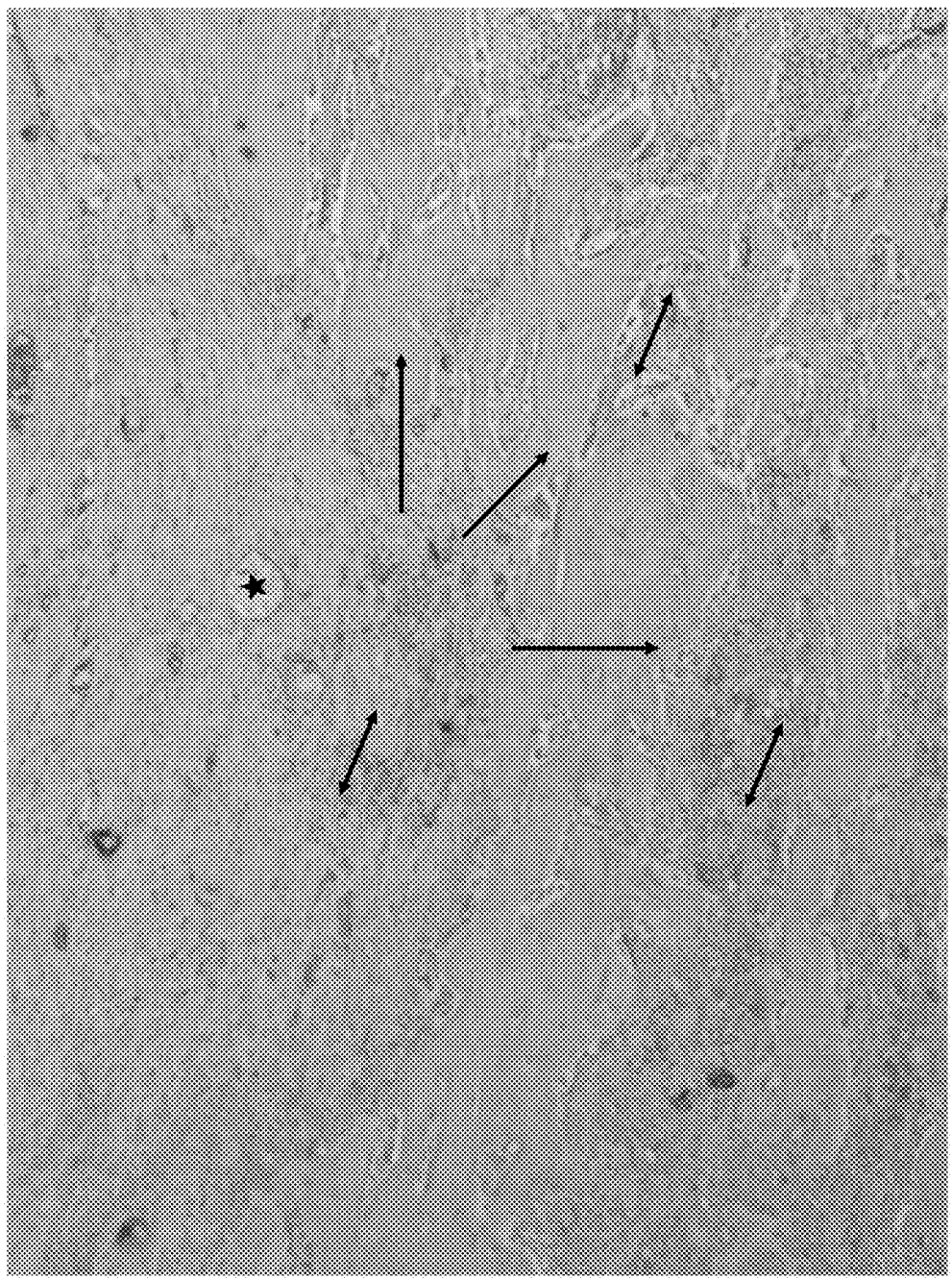

FIG. 12 is a photomicrograph of a rat tibia histological section stained with hematoxylin-eosin (H&E) showing a remnant of Gelrin™ in the gap region of Gelrin™-implanted rat tibia at 5-weeks following the induction of a critical size defect. The image shows the degraded Gelrin™ (star) fibrotically encapsulated, and regions of basic multicellular units (BMU) surrounding. Note the numerous newly formed osseous trabeculae (long arrows) and osseous trabeculae separated by wide tracks of cellular fibrous tissue (double pointed arrows). It is noteworthy to mention that similar features are encountered during gap healing of a bone fracture without contact of the bone edges.

Figure 13:
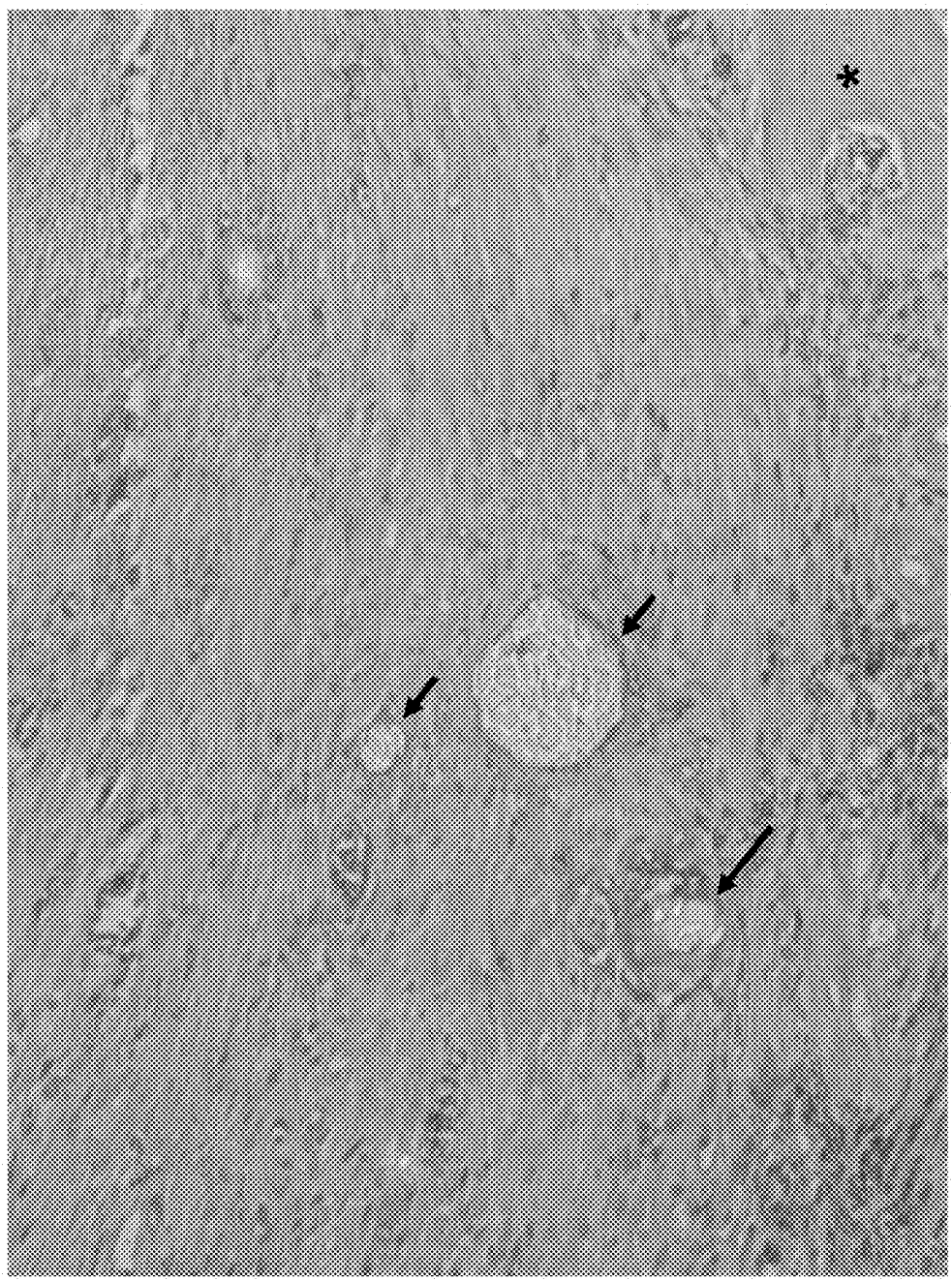

FIG. 13 is a high magnification photomicrograph of a rat tibia histological section stained with hematoxylin-eosin (H&E) showing a remnant of Gelrin™ in the gap region of Gelrin™-implanted rat tibia at 5-weeks following the induction of a critical size defect. This image shows in greater detail the dense connective matrix and formation of new bone near the residual Gelrin™ of a rat tibia 5-weeks following implantation. Short arrows indicate the regions of residual Gelrin™ surrounded by dense connective matrix and formation of new bone [asterisk (*)]. The cut edge of the bone with BMU (on the right lower corner) indicates the remodeling activity of mature bone in which the BMU prepares the way for new bone formation. The appearance of several small areas of residual Gelrin™ suggests that this tissue section represents the center of the gap. Note the presence of fibrous tissue without an inflammatory response around the two round collections of broken-up Gelrin™ (short arrows), demonstrating the biocompatible characteristics of the Gelrin™ hydrogel.

Figure 14:
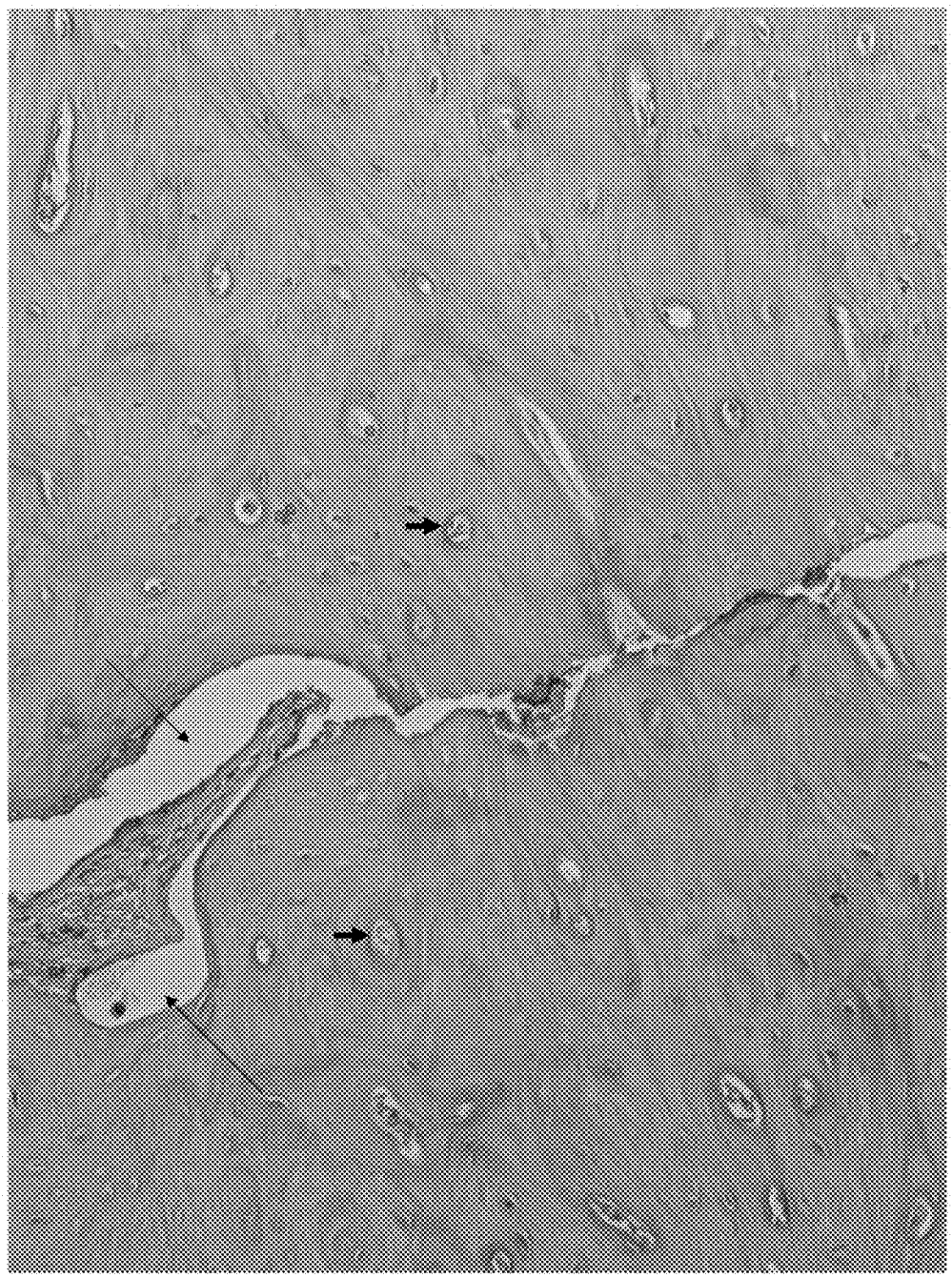

FIG. 14 is a photomicrograph depicting new bone formation in the gap region of a Gelrin™-treated animal. Shown is a histological section of a rat tibia 5 weeks following the creation of the critical size tibia defect and subsequent Gelrin™ implantation. The observed crack with the empty spaces around the septum (long arrows) is partly a result of sectioning the paraffin block which contains two different tissues (i.e., bone and fibrous tissue) exhibiting different biomechamical properties (i.e., a sectioning artifact). Note the presence of a fibrous tissular septum inside the "crack". Also note the well-formed Haversian systems (short arrows) representing part of the preexisting cortex and a compacta bone.

Figure 15:
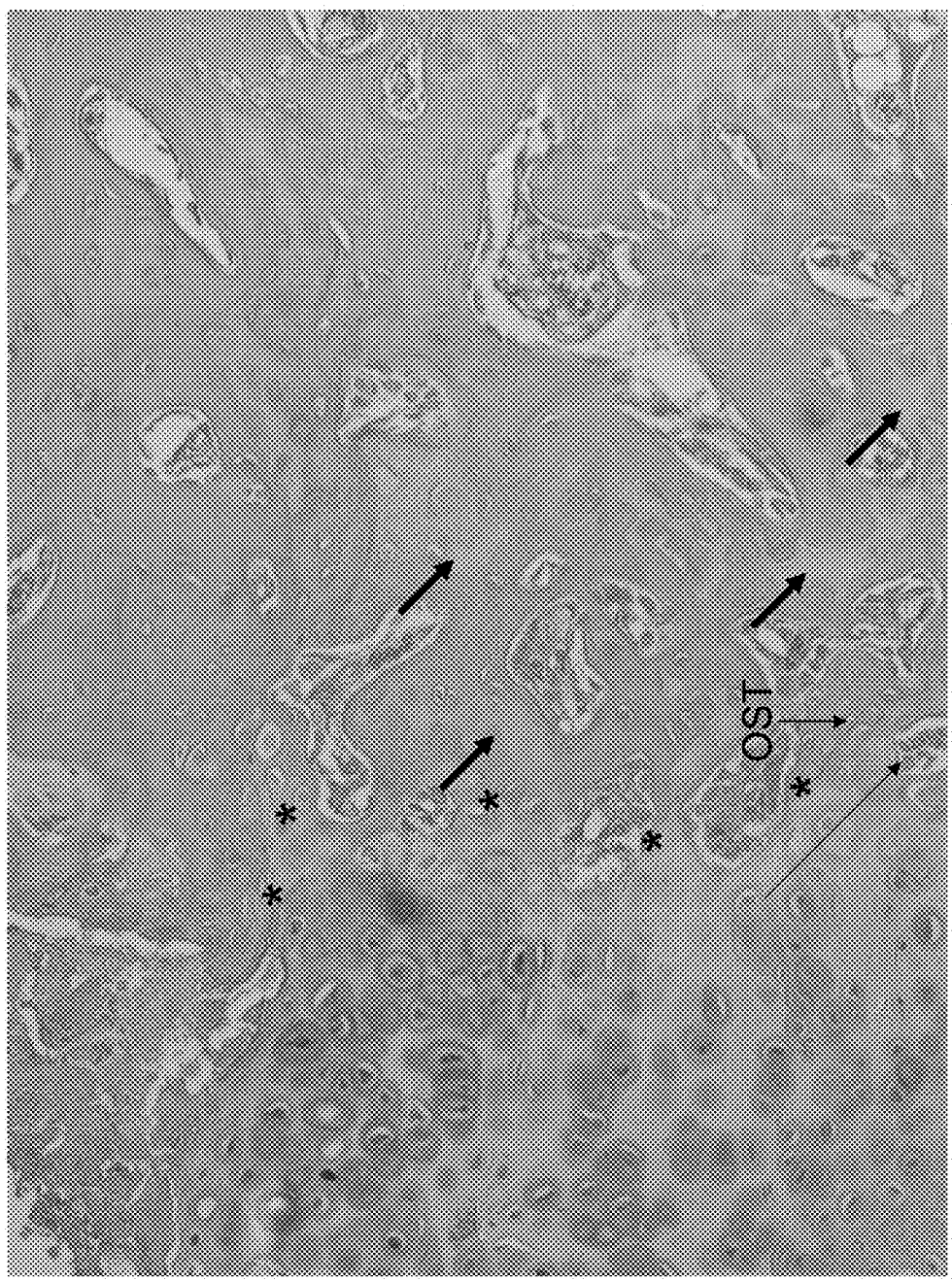

FIG. 15 is a photomicrograph of a histological section of rat tibia depicting a characteristic view of primary bone at 5 weeks following implantation of Gelrin™ in the defect site of a critical size defect in the rat tibia. Note the cartilage undergoing endochondral ossification (in the bottom, left-hand side of the image) as evidenced by the ingrowth of vascularized fibrous tissue into the chondroid matrix (denoted by asterisks). The striking feature is the presence of rows of cuboidal osteoblasts (OST) along the newly formed bone. There is even a cluster of osteoblasts within the cartilage itself (long arrow). The diagnosis of primary bone is based on the presence of chondroid (basophilic) rests within the bone (short arrows). The presence of enlarged Haversian-like canals with the rows of cuboidal osteoblasts abutting on the bone, indicates the presence of extensive appositional osteogenesis at this stage following treatment.

Figure 16:
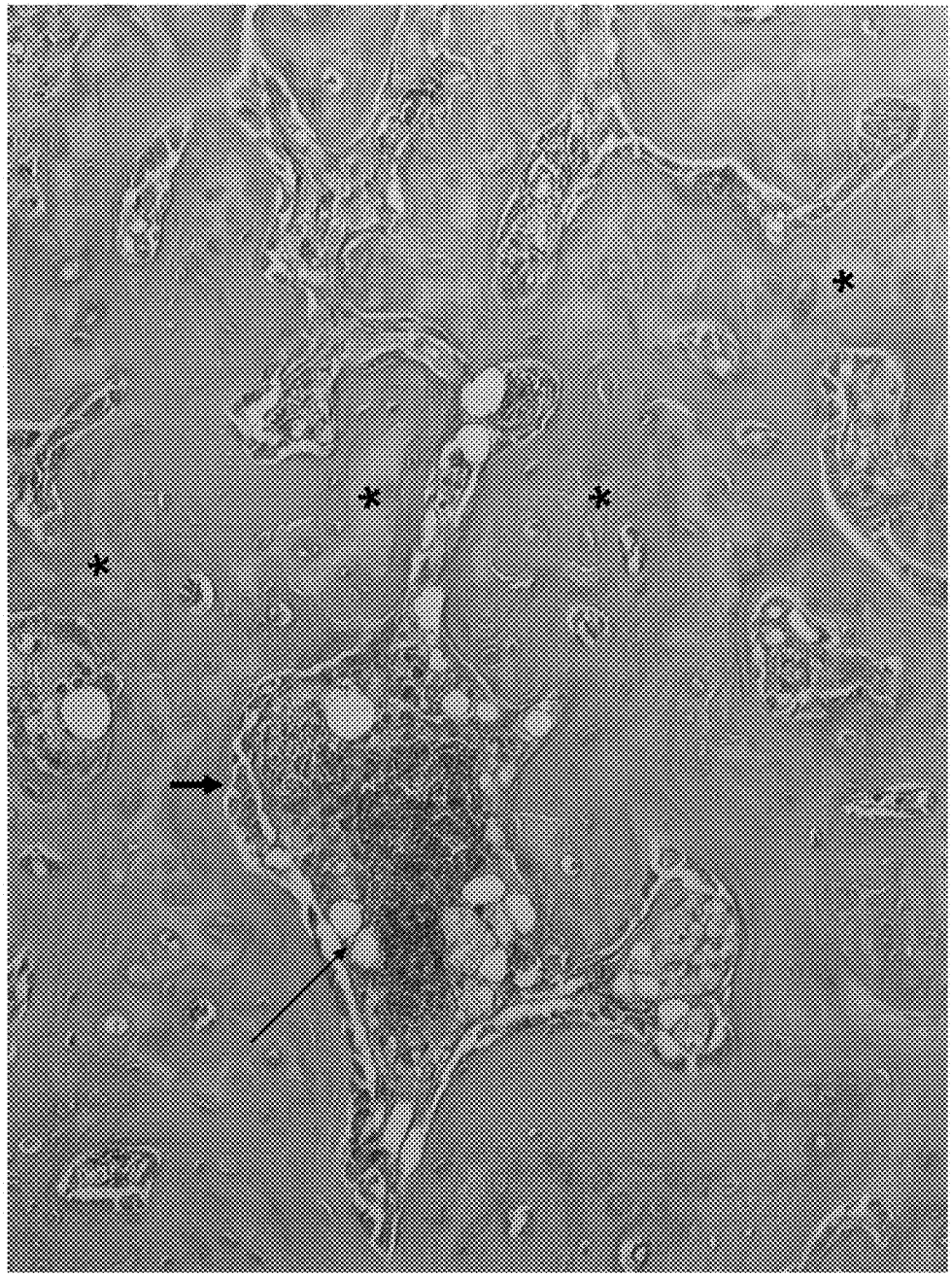

FIG. 16 is a photomicrograph of a histological section showing a primitive—primary bone in a Gelrin™-treated rat critical size tibial defect at 5 weeks following implantation. Note the abundance of residual beams of the initially present cartilage (asterisks), which at this stage has been replaced by osseous tissue. There is a complex network of channels. Note that the large Haversian-like canals in the center is at least partly hypervascularized, and contains a few lipocytes (long arrow). Most of the canal-bone interfaces are covered by cuboidal osteoblasts (small arrows), indicative of ongoing lively osteogenesis.

Figure 17:
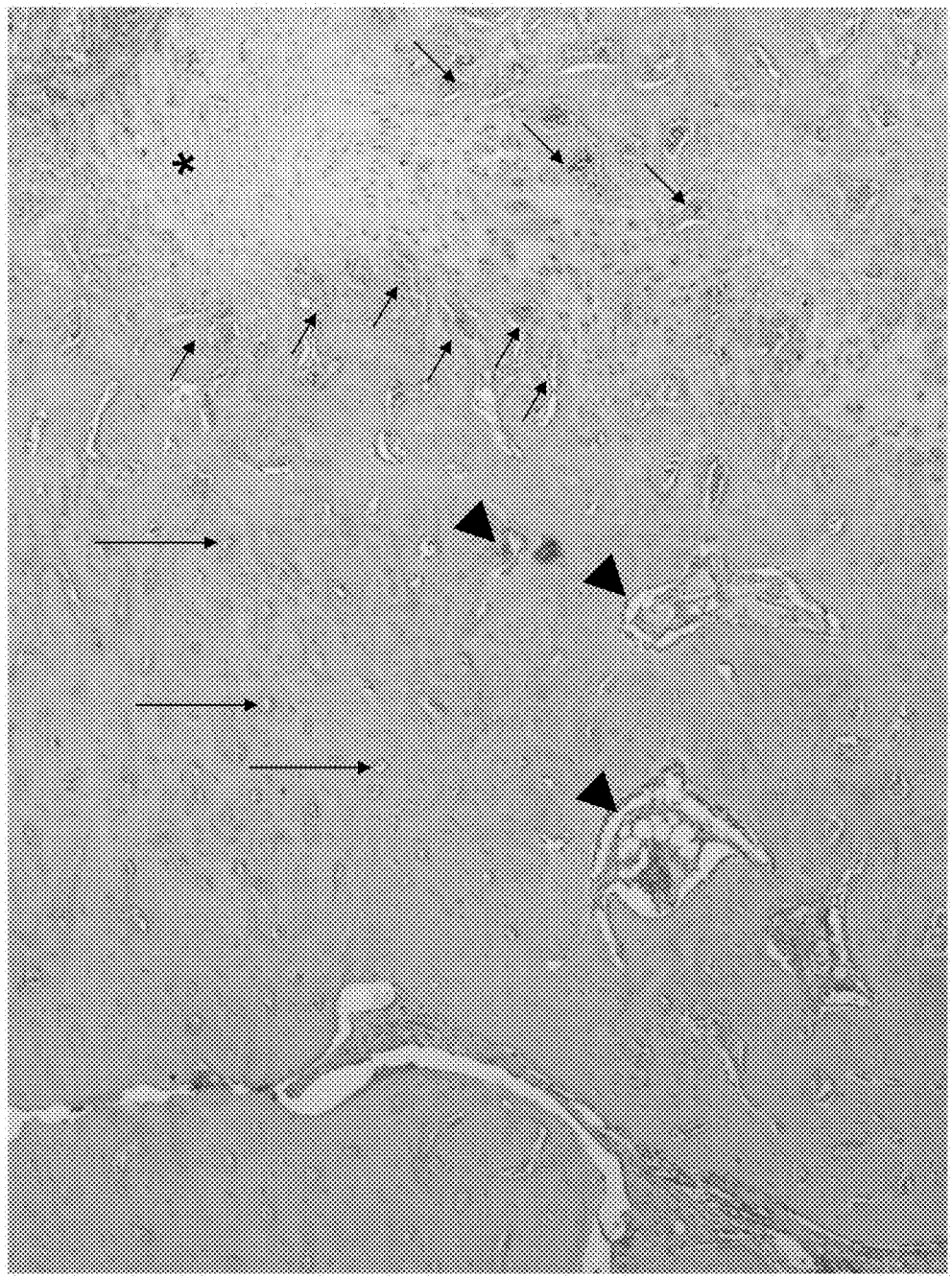

FIG. 17 is a low-power photomicrograph showing a band of transitioning chondroid tissue in the gap region of a Gelrin™-treated animal. Note the band of cartilage (upper end, indicated by asterisk) in which a transition from fibrous tissue into chondroid tissue is evident (transition occurs from top to bottom, respectively). On both sides of this band, many vascularized fibrous tissular projections (short arrows) are invading the cartilage, i.e., initiating endochondral ossification. Although the bone is of osteonal pattern with numerous normal Haversian canals (long arrows), it is abnormally structured in as much as there are several large fibro-fatty tissular tracks with rows of cuboidal osteoblasts abutting on the bone (indicated by arrow heads).

Figure 18A:
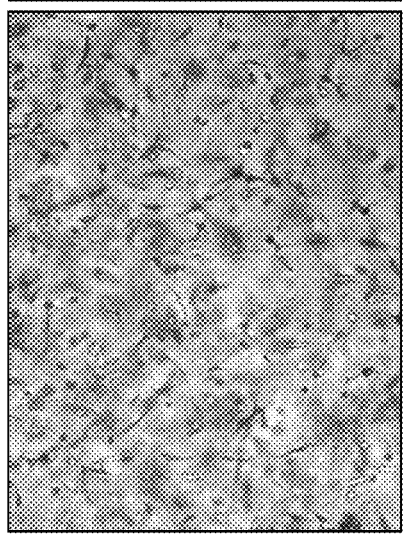
Figure 18B:
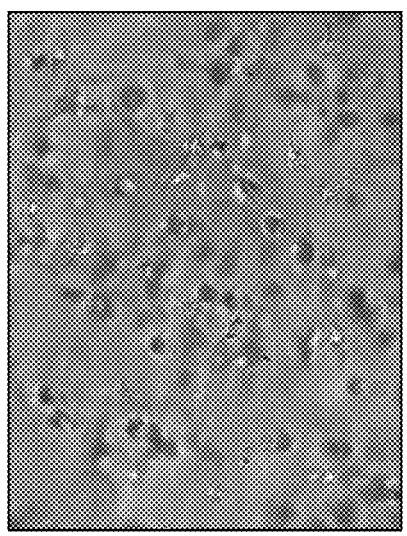
Figure 18C:
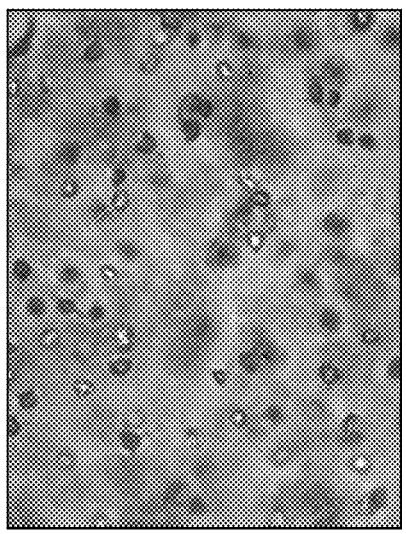
Figure 18D:
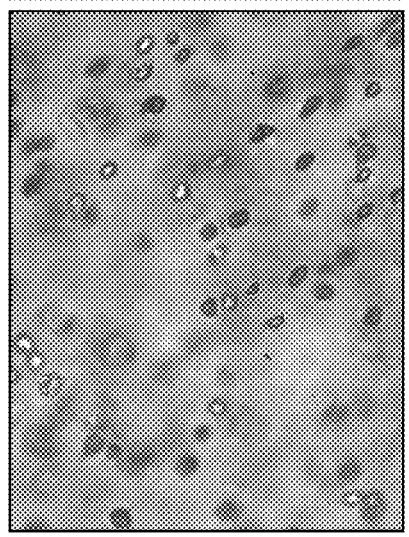
Figure 18E:
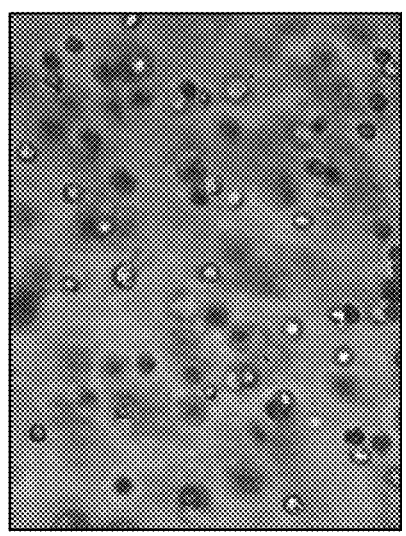

FIGS. 18a-e are phase-contrast microscopic images of vascular smooth muscle cell cultures inside Gelrin™ Hydrogels. Homogeneously distributed and dispersed smooth muscle cells were cultured for 48 hours inside Gelrin™ hydrogels (10-kDa PEG) and the ability of the cells to attach and spread inside the hydrogels was qualitatively assessed by phase contrast microscopy. FIG. 18a illustrates the three-dimensional attachment and spreading of smooth muscle cells inside the pure Gelrin™ hydrogels. The addition of varying amounts of free PEG-DA (FIG. 18b-e) to the Gelrin™ matrix reduced the proteolytic degradability of the hydrogels and makes it more difficult for individual cells to spread with in the matrix. FIG. 18a—pure Gelrin™ matrix; FIG. 18b—Gelrin™ matrix with 0.5% free PEG-DA; FIG. 18c—Gelrin™ matrix with 1% free PEG-DA; FIG. 18d—Gelrin™ matrix with 1.5% free PEG-DA; FIG. 18e—Gelrin™ matrix with 2% free PEG-DA. Note that the attachment and spreading of the cells inside the matrix is reduced in the presence of increasing concentrations of free PEG-DA (i.e., the cross-linking molecule) to the pure Gelrin™ matrix.

FIGS. 19a-l are photomicrographs of smooth muscle cell clusters embedded within a Gelrin™ substrate. The figure depicts the effect of the increasing concentrations of PEG-DA in the Gelrin™ hydrogels on migration of the cells into the Gelrin™. Gelrin™ hydrogels consisting of 6-kDa PEG were prepared using pure Gelrin™ hydrogels (1.75% PEG-fibrinogen; FIGS. 19a-d), Gelrin™ hydrogels cross-linked with 1% free PEG-DA (FIGS. 19e-h) or Gelrin™ hydrogels cross-linked with 2% free PEG-DA (FIGS. 19i-l) and the degree of cell migration from the cellularized tissue mass (dark) and into the Gelrin™ was detected using phase contrast microscopy following one (FIGS. 19a, e, and i), two (FIGS. 19b, f and j), four (FIGS. 19c, g, and k), or seven (FIGS. 19d, h and l) days in culture. Note the significant cell migration seen in pure Gelrin™ hydrogels and the relatively decreased cell extensions observed in Gelrin™ hydrogels which were cross-linked in the presence of 2% free PEG-DA.

FIGS. 20a-c are radiographic images showing new bone formation in treated rats at 5 weeks following the induction of a critical size defect. Intermediate degrading hydrogel-treated rats (treatment-2) exhibit extensive new bone formation in the site of the defect as indicated by the formation of a periosteal callus (arrows); the extent of osteoneogenesis ranges from a total bony bridge of the defect (FIG. 20a) to a partially regenerated bone in the gap (FIG. 20b). All other treatments are similar to non-treated (control) rats (FIG. 20c) which disclose no new bone formation by radiographic imaging.

FIGS. 21a-c are photomicrographs of longitudinal sections of intermediate-degrading hydrogel-treated tibial defects at 5 weeks following the induction of a critical size defect stained with hematoxylin-eosin (H&E). The extent of regenerated bone in the site-specific defect ranges from partial (FIG. 21a, FIG. 21b) to total bridging (FIG. 21c) of the defect osteotomies (ost), and highly depends on the erosion pattern of the hydrogel material (Gel). Remnants of the gel give way to regenerated bone (dashed line), having typical lamellar-fibred pattern of mature osseous trabeculae and fatty marrow (FM).

FIGS. 22a-b are photomicrographs of newly formed sub-periosteal and endosteoal bone shown with partially degraded hydrogel in a longitudinal section of an intermediate-degrading hydrogel-treated rat. FIG. 22a shows the osseous trabeculae, which conncet with one another and are rimmed by active cuboidal osteoblasts. The intertrabecular spaces are occupied by a fatty marrow (FM), which extends well into the site of the defect from the aspect of the medial osteotomy (ost). A cartilaginous cap (arrows) at the medial end of the front of the regenerated bone is seen with islets of hypertrophic chondrocytes. The cap is enclosed by a thin layer of perichondrium-like fibrous tissue. Fibro-fatty tissue (FT) is present in between the degraded hydrogel and the regenerated bone. FIG. 22b is a higher magnification of the same field as in FIG. 22a. This field displays endochondrol ossification (ECO) in the cartilaginous region. The sections are stained with hematoxylin and eosin (H&E).

FIGS. 23a-c are photomicrographs showing that the extent of hydrogel degradation affects bone healing response at 5 weeks following the induction of a critical size defect. FIG. 23a shows that the presence of the fast-degrading hydrogels (treatment-1) within the site of the implant results in non-union, the gap being occupied by fibrous connective tissue (CT) with a minor mononuclear celled inflammatory infiltrate. FIG. 23b shows the defect site of a rat with an implant of the slow degrading hydrogels (treatment-3) filled with the hydrogel, which is enclosed within a fibrous capsule and regenerated bone at the osteotomy (ost) locale. FIG. 23c shows the intermediate-degrading hydrogel being eroded by granulation tissue and subjacent newly formed bone (NB). The sections are stained with hematoxylin and eosin (H&E).

FIGS. 24a-b are photomicrographs showing the cellular response to the PEG-fibrinogen Hydrogel Implant. FIG. 24a illustrates the classical serpentine granulation tissue at the eroding front of the hydrogel (solid arrows) with adjacent nonspecific chronic inflammatory infiltrate, which is primarily composed of lymphocytes (LR) and is accompanied by newly formed bone (NB). In certain areas of the tissue-material interface the response is limited to only a minor chronic nonspecific inflammatory reaction (dashed arrow). The eosinophilic hydrogel is lightly stained and shows no cellular infiltration beyond the eroding borders of the dense matrix (gel). FIG. 24b is a high magnification micrograph showing the pallisading granulation tissue; of note is the minor macrophagic reaction (MR).

FIGS. 25a-c are photographs showing the encapsulation of a single dorsal root ganglion (DRG) into a PEGylated fibrinogen hydrogel. FIG. 25a illustrates that the DRG (arrow) is roughly 0.5 mm in diameter and is situated in the center of a 10 mm diameter PEGylated fibrinogen hydrogel. Radial outgrowth is measured from the outer boundary of the opaque DRG into the transparent hydrogel. The same constructs is shown from the top view (FIG. 25b) and the side view (FIG. 25c).

FIGS. 26a-d are photomicrographs showing outgrowth and cellular invasion characteristics of DRGs in PEGylated fibrinogen 3-D hydrogel constructs. Phase-contrast micrographs (FIGS. 26a and 26b) show the three-dimensional outgrowth of neurites (arrow) and glial cells (arrowhead) extending from the DRG (D) into the transparent PEGylated fibrinogen hydrogel construct (P) following two days in culture. Histological sections stained with H&E (FIGS. 26c and 26d) of the DRG (dark) in the PEGylated fibrinogen construct (light) show neurite (arrow) and non-neuronal cells (arrowhead) invading the hydrogels after four days in culture. Note: high magnification images (FIGS. 26b and 26d) are expanded regions from the lower magnification micrographs (FIGS. 26a and 26c); in all images the scale bar=100 μm.

FIGS. 27a-f are fluorescent microscope images of DRGs encapsulated in PEGylated fibrinogen constructs confirming the presence of both neurites and schwann cells. Cross sections of DRG constructs were cultured for four days and fluorescently triple-labeled with βIII-tubulin (neurite marker, FIGS. 27a and 27d), s100 (Schwann cell marker, FIGS. 27b and 27e), and DAPI counter-stain (nuclei, blue). The merged micrographs (FIGS. 27c and 27f) show the three-dimensional invasion of neurites from the DRG into the hydrogel construct, with Schwann cells associated very closely with the neurite extensions (scale bar=50 μm).

FIGS. 28a-d are fluorescent microscope images and graphs showing that both free soluble and enmeshed nerve growth factor (FS-NGF and EN-NGF) promote 3-D neurite outgrowth from encapsulated DRGs into the hydrogels. Sections of DRG constructs following four days were immunofluorescently labeled for βIII-tubulin (neurites, red), s100 (Schwann cells, green) and DAPI nuclear stain (blue) to characterize the invasion into the hydrogels containing FS-NGF (FIG. 28a), EN-NGF (FIG. 28b), or no NGF (NO-NGF; FIG. 28c). Absence of NGF (NO-NGF) did not encourage outgrowth of neurites but supported moderate outgrowth of Schwann cells. Treatments with free soluble or enmeshed NGF exhibited impressive outgrowth of both neurites and Schwann cells (scale bar=50 μm). FIG. 28d is a line graph illustrating that the average neurite extension length (±standard error) in free soluble NGF treatments (FS-NGF) and enmeshed NGF treatments (EN-NGF) is not significantly different between the two treatments (P>0.35, n=6).

FIGS. 29a-u are phase contrast micrographs and graphs showing that PEG-fibrinogen composition controls neurite invasion and outgrowth. The hydrogel composition is varied using different amounts of PEG and fibrinogen during assembly, including 30:1, 60:1, 120:1, and 180:1 (PEG:Fibrinogen). FIGS. 29a-p are phase contrast micrographs showing the profound impact of additional PEG on the 3-D outgrowth morphology from the DRG following four days (scale bar=200 µm). FIGS. 29q-t are high magnification images showing the relative outgrowth of neurites and glial cells into hydrogels having different compositions (scale bar=200 µm). FIG. 29u is a line graph showing that the average neurite extension length (±standard error) in each treatment, as measured directly from the images, shows no significant difference between the 30:1 and 60:1 treatments (P>0.50, n=9), and a significant impediment to outgrowth in the 120:1 and 180:1 treatments (p<0.01, n=9).

FIGS. 30a-c are phase contrast micrographs showing DRG outgrowth into hydrogels made from PEG-DA and PEG-fibrinogen. Constructs were prepared with 10% PEG-DA gels (w/v) without fibrinogen (FIG. 30a) and compared with PEG-fibrinogen constructs (FIG. 30b). Neurite extensions were barely visible following three days in PEG-DA construct compared to extensive invasion seen in PEGylated fibrinogen constructs after three days. Neuronal invasion into PEGylated fibrinogen hydrogels was eliminated in the absence of NGF (FIG. 30c), although other cells types were observed in the hydrogel following three days in culture. In all images the scale bar=200 µm.

DESCRIPTION OF THE PREFERRED EMBODIMENTS

The present invention is of a matrix composed of a naturally-occurring protein backbone cross-linked by polyethylene glycol (PEG) which can be used in tissue regeneration applications. Specifically, the present invention is of a PEGylated fibrinogen scaffold which can be used to treat disorders characterized by tissue damage or loss using biodegradable scaffolds.

The principles and operation of the method of generating a biodegradable scaffold according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Tissue engineering approaches utilize basic scaffolds which mimic the natural structure of the tissues they replace and provide temporary functional support for cells seeded thereon (Griffith L G, 2002). Scaffolds can be fabricated from either biological materials or synthetic polymers. While synthetic polymers [e.g., polyethylene glycol (PEG) and Polymethyl methacrylate (PMMA)], provide precise control over the scaffold material and its mechanical properties, such polymers are devoid of biofunctional properties which enable cell attachment and spreading (Drury and Mooney, 2003), and are therefore unsuitable for long-term tissue culture or in vivo tissue regeneration.

Naturally occurring scaffolds such as collagen and fibrin provide bio-functional signals and exhibit various cellular interactions. However, since such biological materials exhibit multiple inherent signals (e.g., regulation of cell adhesion, proliferation, cellular phenotype, matrix production and enzyme activity), their use as scaffolds for tissue regeneration often results in abnormal regulation of cellular events (Hubbell, 2003). In addition, following reconstitution, the strength of such scaffolds is lower than that characterizing the natural biological material (e.g., collagen).

To overcome such limitations "hybrid" scaffolds were constructed by grafting biodegradable elements into synthetic backbones. Thus, synthetic PEG backbone was cross-linked with short oligopeptides containing enzymatic substrates, RGD and/or VEGF sequences [Lutolf et al (2003); Gobin and West (2002); Seliktar et al; 2004, Zisch A H, et al, 2003; FASEB J. 17: 2260-2. Epub 2003 Oct. 16], or with genetically-engineered protein-like precursors of 100 amino acids (Halstenberg et al. 2002; Biomacromolecules, 3: 710-23). However, such scaffolds, in which PEG was the major component, failed to provide sufficient bio-feedback and/or long-term cellular responses which are essential for tissue regeneration and phenotypic stability. An improvement of such scaffold is characterized by the addition of other growth factors to the premade scaffold, however in this case the growth factor does not form the scaffold but rather is an auxiliary component thereof [Lutolf M P, Weber F E, Schmoekel H G, Schense J C, Kohler T, Muller R, Hubbell J A. Repair of bone defects using synthetic mimetics of collagenous extracellular matrices. Nat. Biotechnol. 2003 May; 21(5):513-8].

Other attempts made by Fortier and co-workers consisted of a single step scaffold generation process, which resulted in a scaffold formed from naturally occurring proteins which is capable of mediating biological cues. However, in the absence of further purification steps, such a scaffold included toxic unreacted amine-reactive di-functional PEG, which disqualified its use in the clinic [Jean-Francois J, D'Urso E M, Fortier G. Immobilization of L-asparaginase into a biocompatible poly(ethylene glycol)-albumin hydrogel: evaluation of performance in vivo. Biotechnol Appl Biochem. 1997 Dec. 26 (Pt 3):203-12; Jean-Francois J, Fortier G. Immobilization of L-asparaginase into a biocompatible poly(ethylene glycol)-albumin hydrogel: I: Preparation and in vitro characterization. Biotechnol Appl Biochem. 1996 Jun. 23 (Pt 3):221-6; Gayet J C, Fortier G. Drug release from new bioartificial hydrogel. Artif Cells Blood Substit Immobil Biotechnol. 1995; 23(5):605-11; D'Urso E M, Jean-Francois J, Doillon C J, Fortier G. Poly(ethylene glycol)-serum albumin hydrogel as matrix for enzyme immobilization: biomedical applications. Artif Cells Blood Substit Immobil Biotechnol. 1995; 23(5):587-95].

While reducing the present invention to practice, the present inventors have uncovered that biosynthetic hybrid scaffolds composed of a fibrinogen backbone with functional polyethylene glycol (PEG) side chains are excellent, biodegradable scaffolds and that such scaffolds can be used for tissue regeneration applications.

As is shown in the Examples section which follows, the present inventors generated PEG-fibrinogen precursor molecules which were further used to form hydrogel scaffolds. The PEG-fibrinogen scaffolds of the present invention exhibit material properties and biodegradability which are superior to any known prior art scaffolds; they also exhibit high flexibility and a controllable elastic modulus (FIGS. 3a-b), efficient biodegradability (FIGS. 5a-b), improved biofunctionality and support for cell spreading and extension (FIGS. 6a-e, 7a-b, 18a-e and Examples 2 and 4). As shown in FIGS.

9-17 and FIGS. 20a-c and FIGS. 23a-c in Examples 3 and 5 of the Examples section which follows, the PEG-fibrinogen scaffolds of the present invention were capable of in vivo bone regeneration in rats exposed to critical size tibia defect.

Moreover, as illustrated in FIGS. 26-30 in Example 6, the PEG-fibrinogen scaffolds of the present invention were also capable of ex vivo nerve regeneration.

In sharp contrast to the above-described scaffolds consisting of multi-functional PEG network cross-linked with reactive synthetic oligopeptide, the present invention employs a natural protein PEGylated with di-functional or multi-functional PEG to form the backbone precursor molecule. The naturally occurring PEGylated protein of the present invention is both the degradation substrate and the main constituent of the biological signaling of the matrix. The biodegradation is controlled by the composition of PEG and protein: the degree of PEGylation, the relative amount of PEG and protein, and the length of the PEG molecules. The protein backbone also serves as the main signaling constituent of the scaffold, compared to the synthetic system where factors (growth factors) and other biofunctional synthetic oligopeptides (RGD) can be tethered to the multi-functional PEG network through an additional reaction in order to create further biological signals required for tissue healing. Because the biological activity is inherent to the protein backbone of the present invention, the same fragments of the denatured PEGylated protein which may contain many inductive properties that are relevant for physiological injury response can contribute to the observed healing of the defect as the matrix is degraded.

Thus, according to one aspect of the present invention there is provided a composition-of-matter comprising a naturally occurring protein or a bioactive fragment thereof and at least two synthetic polymers covalently attached thereto, each of said at least two synthetic polymers having a functional group being capable of attaching to said naturally occurring protein or said bioactive fragment thereof so as to form a scaffold.

As used herein the phrase "scaffold" refers to a two-dimensional or a three-dimensional supporting framework. The scaffold of the present invention is composed of units (interchangeably referred to herein as "precursor molecules") which are directly or indirectly (e.g., via linker) attachable therebetween. Such precursor molecule can be for example, PEGylated fibrinogen (see Example 1 of the Examples section which follows), PEGylated collagen, PEGylated fibronectin and the like. By controlling cross-linking, the scaffold of the present invention can form two- or three-dimensional structure at any size, structure or porosity. The scaffold of the present invention can be embedded within, or formed around, another scaffold or gel or it can be linked to additional materials to form a hybrid or coated scaffold.

Preferably, the scaffold of the present invention can be used to support cell growth, attachment, spreading, and thus facilitate cell growth, tissue regeneration and/or tissue repair.

The term "polymer" refers to a plurality of repeating units which form a new molecular structure. The phrase "synthetic polymer" refers to any polymer which is made of a synthetic material, i.e., a non-natural, non-cellular material. Non-limiting examples for synthetic polymers which can be used along with the present invention include polyethylene glycol (PEG) (average Mw. 200; P3015, SIGMA), Hydroxyapatite/polycaprolactone (HA/PLC) [Choi, D., et al., 2004, Materials Research Bulletin, 39: 417-432; Azevedo M C, et al., 2003, J. Mater Sci. Mater. Med. 14(2): 103-7], polyglycolic acid (PGA) [Nakamura T, et al., 2004, Brain Res. 1027(1-2): 18-29], Poly-L-lactic acid (PLLA) [Ma Z, et al., 2005, Biomaterials. 26(11): 1253-9], Polymethyl methacrylate (PMMA) [average Mw 93,000, Aldrich Cat. #370037; Li C, et al., 2004, J. Mater. Sci. Mater. Med. 15(1): 85-9], polyhydroxyalkanoate (PHA) [Zinn M, et al., 2001, Adv. Drug Deliv. Rev. 53(1): 5-21; Sudesh K., 2004, Med. J. Malaysia. 59 Suppl B: 55-6], poly-4-hydroxybutyrate (P4HB) [Dvorin E L et al., 2003, Tissue Eng. 9(3): 487-93], polypropylene fumarate (PPF) [Dean D, et al., 2003, Tissue Eng. 9(3): 495-504; He S, et al., 2000, Biomaterials, 21(23): 2389-94], polyethylene glycol-dimethacrylate (PEG-DMA) [Oral E and Peppas N A J, 2004, Biomed. Mater. Res. 68A(3): 439-47], beta-tricalcium phosphate (beta-TCP) [Dong J, et al., 2002, Biomaterials, 23(23): 4493-502], and nonbiodegradable polytetrafluoroethylene (PTFE) [Jernigan T W, et al., 2004. Ann. Surg. 239(5): 733-8; discussion 738-40].

The synthetic polymers of this aspect of the present invention may be identical or different. As mentioned hereinabove, each of the synthetic polymers in the composition comprises a functional group which is capable of forming a direct or indirent bond with the naturally occurring protein such as to a side chain thereof or to an end group. Such a functional group may comprise an amine a thiol and the like.

According to presently preferred embodiments of the present invention the synthetic polymer used by the present invention is PEG. The PEG molecule used by the present invention can be linearized or branched (i.e., 2-arm, 4-arm, and 8-arm PEG) and can be of any molecular weight, e.g., 4 kDa, 6 kDa and 20 kDa for linearized or 2-arm PEG, 14 kDa and 20 kDa for 4-arm PEG, and 14 kDa and 20 kDa for 8-arm PEG and combination thereof.

As is shown in FIGS. 1a-b and Example 1 of the Examples section which follows the OH-termini of the PEG molecule can be reacted with a chemical group such as acrylate (Ac) or vinylsulfone (VS) which turn the PEG molecule into a functionalized PEG, i.e., PEG-Ac or PEG-VS. Preferably, the PEG molecule used by the present invention is PEG-Ac.

Methods of preparing functionalized PEG molecules are known in the arts. For example, PEG-VS can be prepared under argon by reacting a dichloromethane (DCM) solution of the PEG-OH with NaH and then with di-vinylsulfone (molar ratios: OH 1: NaH 5: divinyl sulfone 50, at 0.2 gram PEG/mL DCM). PEG-Ac is made under argon by reacting a DCM solution of the PEG-OH with acryloyl chloride and triethylamine (molar ratios: OH 1: acryloyl chloride 1.5: triethylamine 2, at 0.2 gram PEG/mL DCM), essentially as described in Example 1 of the Examples section which follows.

It will be appreciated that such chemical groups can be attached to linearized, 2-arm, 4-arm, or 8-arm PEG molecules.

Preferably, the PEG-Ac used by the present invention is PEG-DA, 4-arm star PEG multi-Acrylate and/or 8-arm star PEG multi-Acrylate.

As is shown in FIGS. 2a-b and Example 1 of the Examples section which follows the present inventors used 4-kDa, 6-kDa and 20-kDa isoforms of PEG-diacrylate (PEG-DA) to prepare functionalized PEG molecules.

According to a presently known preferred embodiment of the present invention, a 6-14 kDa PEG-diacrylate is used.

The phrase "naturally occurring protein or a portion thereof" as used herein refers to any peptide, polypeptide or protein which exists in nature, such as in eukaryotic and/or prokaryotic organisms, cells, cellular material, non-cellular material and the like. Such a protein or a portion thereof may have a known or unknown structure, function, or molecular properties. For example, the protein of the present invention can be a cell signaling protein, an extracellular matrix protein, a cell adhesion protein, a growth factor, a protease, and a protease substrate.

Examples for cell signaling proteins include, but are not limited to, p38 mitogen-activated protein kinase (GenBank Accession No. NP_002736), nuclear factor kappaB (GenBank Accession No. NP_003989), Raf kinase inhibitor protein (RKIP) (GenBank Accession No. XP_497846), Raf-1 (GenBank Accession No. NP_002871), MEK (GenBank Accession No. NP_002746), Protein kinase C (PKC) (GenBank Accession No. NP_002728), phosphoinositide-3-kinase gamma (GenBank Accession No. NP_002640), receptor tyrosine kinases [e.g., insulin receptor (GenBank Accession No. NP_000199)], heterotrimeric G-proteins [e.g., Galpha(i) (GenBank Accession No. NP_002060), Galpha(s) NP_000507 and Galpha(q) (GenBank Accession No. NP_002063)], Caveolin-3 (GenBank Accession No. NP_001225), 14-3-3 proteins (GenBank Accession No. NP_003397).

Examples for extracellular matrix proteins include, but are not limited to, fibrinogen [β-chain—GenBank Accession No. NP_068657 (SEQ ID NO:4); β-chain—GenBank Accession No. P02675 (SEQ ID NO:5); γ-chain—GenBank Accession No. P02679 (SEQ ID NO:6)], Collagen (GenBank Accession No. NP_000079), fibronectin (GenBank Accession No. NP_002017), vimentin (GenBank Accession No. NP_003371), microtubule-associated protein 1b (GenBank Accession No. NP_005900) (Theodosis D T. 2002; Front Neuroendocrinol. 23: 101-35), Neurite outgrowth factor (NOF) (GenBank Accession No. P21741) (Tsukamoto Y, et al., 2001; Histol. Histopathol. 16: 563-71), bacterial cellulose (BC) (GenBank Accession No. NP_625477), laminin (GenBank Accession No. NP_000218) and gelatin [Zhang Y., et al., 2004; J Biomed Mater Res. 2004 Sep. 22; Epub ahead of print].

Examples for cell adhesion proteins include, but are not limited to, integrin (GenBank Accession No. NP_002202) (Stefanidakis M, et al., 2003; J Biol. Chem. 278: 34674-84), intercellular adhesion molecule (ICAM) 1 (GenBank Accession No. NP_000192) (van de Stolpe A and van der Saag P T. 1996; J. Mol. Med. 74: 13-33), N-CAM GenBank Accession No. NP_000606), cadherin (GenBank Accession No. NP_004351), tenascin (GenBank Accession No. NP_061978) (Joshi P, et al., 1993; J. Cell Sci. 106: 389-400), gicerin (GenBank Accession No. NP_006491), and nerve injury induced protein 2 (ninjurin2) (GenBank Accession No. NP_067606) (Araki T and Milbrandt J. 2000; J. Neurosci. 20: 187-95).

Examples of growth factors include, but are not limited to, Epidermal Growth Factor (GenBank Accession No. NP_001954), transforming growth factor-beta (GenBank Accession No. NP_000651), fibroblast growth factor-acidic (GenBank Accession No. NP_000791), fibroblast growth factor-basic (GenBank Accession No. NP_001997), erythropoietin (GenBank Accession No. NP_000790), thrombopoietin (GenBank Accession No. NP_000451), hepatocyte growth factor (GenBank Accession No. NP_000592), insulin-like growth factor-I (GenBank Accession No. NP_000609), insulin-like growth factor-II (GenBank Accession No. NP_000603), Interferon-gamma (GenBank Accession No. NP_000610), and platelet-derived growth factor (GenBank Accession No. NP_079484).

Examples for protease proteins include, but are not limited to, pepsin (GenBank Accession No. NP_055039), low specificity chymotrypsin, high specificity chymotrypsin, trypsin (GenBank Accession No. NP_002760), carboxypeptidases (GenBank Accession No. NP_001859), aminopeptidases (GenBank Accession No. NP_001141), proline-endopeptidase (GenBank Accession No. NP_002717), *Staphylococcus aureus* V8 protease (GenBank Accession No. NP_374168), Proteinase K (PK) (GenBank Accession No. P06873), aspartic protease (GenBank Accession No. NP_004842), serine proteases (GenBank Accession No. NP_624302), metalloproteases (GenBank Accession No. NP_787047), ADAMTS17 (GenBank Accession No. NP_620688), tryptase-gamma (GenBank Accession No. NP_036599), matriptase-2 (GenBank Accession No. NP_694564).

Protease substrate proteins include the peptide or peptide sequences being the target of the protease protein. For example, Lysine and Arginine are the target for trypsin; Tyrosine, Phenylalanine and Tryptophan are the target for chymotrypsin.

Such naturally occurring proteins can be obtained from any known supplier of molecular biology reagents such as Sigma-Aldrich Corp., St Louis, Mo., USA and Invitrogen Carlsbad Calif.

As is mentioned hereinabove, portions (fragments e.g., bioactive fragments capable of mediating biological funciton) of such proteins can be also used to generate the composition of the present invention. Such a portion usually includes sufficient biodegradability potential, i.e., protease substrates and/or protease targets, as well as sufficient cell signaling and/or cell adhesion motives. For example, the human fibrinogen protein contains two RGD adhesion sites at amino acids 114-116 and 591-593 of the α-chain as set forth in SEQ ID NO:4 (GenBank Accession No. NP_068657), as well as a protease cleavage site at amino acids 44-45 of the β-chain as set forth in SEQ ID NO:5 (GenBank Accession No. P02675).

The above described composition of matter may be cross-linked to form a scaffold.

Thus, according to another aspect of the present invention there is provided a scaffold comprising a plurality of protein molecules covalently attached therebetween so as to form the scaffold via a synthetic polymer (such as described hereinabove) having a first part and a second part covalently connected therebetween via a chemical moiety being chemically distinct from a repeating unit of said polymer.

Examples of such chemical moieties include, but are not limited to, aldehyes, acetale, tosyl, tresyl, dichlorotriazine, epoxide, carboxylic, succinimidyle succinate, succinimidyl ester, p-nitrophenyl carbonate, benzotriazolyl carbonate, 2,3,5-trichlorophenyl carbonate, succinimidyle carbonate, pyridildisulphide, maleimide, vinylsulfone, and iodo acetamide Since the scaffold of the present invention is formed from precursor molecules (i.e., the above-described composition of matter) it is devoid of uncojugated forms of the synthetic polymer (such as below 20%, preferably below 15%, preferably below 10% and preferably below 5%), rendering it biologically safe, and particularly useful for clinical applications.

Since the scaffold of the present invention is composed of a naturally occurring protein such a scaffold can be configured susceptible to degradation by biological material such as enzymes, i.e., biodegradable.

As used herein, the phrase "biodegradable" refers to capable of being degraded (i.e., broken down) by biological proteases or biomolecules. Biodegradability depends on the availability of degradation substrates (i.e., biological materials or portion thereof), the presence of biodegrading materials (e.g., microorganisms, enzymes, proteins) and the availability of oxygen (for aerobic organisms, microorganisms or portions thereof), carbon dioxide (for anaerobic organisms, microorganisms or portions thereof) and/or other nutrients. In addition, biodegradability of a material, such as the scaffold of the present invention, also depends on the material structure and/or mechanical properties, i.e., the porosity, flexibility, viscosity, cross-link density, hydrophobicity/hydrophilicity, and elasticity which may affect passage and availability of gasses and nutrients, as well as cell attachment and spreading. Examples of biodegradable materials include, but are not limited to, reconstituted collagen gels, fibrin glues, and hyaluronic acid scaffolds.

Thus, the scaffold of the present invention is fabricated by cross linking multiple copies of a precursor molecule (interchangeable described as the composition-of-matter of the present invention) which is composed of a synthetic polymer attached to a naturally occurring protein or a portion thereof.

For example, as is shown in FIGS. 1a-b, 2a-b and Example 1 of the Examples section which follows, the present inventors fabricated a PEGylated fibrinogen precursor molecule by denaturing fibrinogen molecules and reacting them with functionalized PEG-diacrylates.

Thus, according to preferred embodiments of the present invention, the polymer-protein precursor molecule is made of PEG and fibrinogen.

The molar ratio between the synthetic polymer (e.g., PEG) and the naturally occurring protein (e.g., fibrinogen) of the present invention may affect the pore size, strength, flexibility and elasticity of the scaffold of the present invention. Thus, excess of the synthetic polymer would lead to binding of the polymer functional groups (e.g., PEG-DA) to all potential binding sites on the naturally occurring protein and would result in smaller pore size, more cross-linking sites, higher strength, less flexibility and increased rigidity. On the other hand, binding of only two molecules of the synthetic polymer to each molecule of the protein (i.e., a 2:1 molar ratio) would result in large pore size, fewer cross-linking sites, lower strength, higher flexibility and increased elasticity. It will be appreciated that the molar ratio between the synthetic polymer and the protein can also affect the biodegradability of the scaffold. Thus, a higher molar ratio (i.e., excess of polymer) is expected to result in less biodegradability due to potential masking of protein degradation sites. Those of skills in the art are capable of adjusting the molar ratio between the synthetic polymer and the protein to obtain the desired scaffold with the optimal physical and biological characteristics.

For example, since each fibrinogen molecule includes 29-31 potential sites which can bind to PEG, the PEG-fibrinogen precursor molecule can be prepared using a wide range of molar ratios. Preferably, the molar ratio used by the present invention is 2-400 (PEG) to 1 (fibrinogen), more preferably, the molar ratio is 30-300 (PEG) to 1 (fibrinogen), more preferably, the molar ratio is 100-200 (PEG) to 1 (fibrinogen), most preferably, the molar ratio is 130-160 (PEG) to 1 (fibrinogen). As is shown in Example 1 of the Examples section which follows, one preferable molar ratio between PEG-DA and fibrinogen is 145 (PEG) to 1 (fibrinogen). In the case where the molar ratio is greater than 29-31 (PEG) to 1 (fibrinogen), some of the PEG can be indirectly bound to the fibrinogen through fibrinogen-bound PEG molecules.

The fibrinogen used by the present invention can be whole denatured fibrinogen (i.e., un-cleaved) or fragmented fibrinogen, which can be obtained using, for example, CNBr cleavage (see Example 1 of the Examples section which follows).

Fibrinogen can be readily purified from human blood plasma using standard protein purification techniques. Purified components may be subject to anti-viral treatments. Heat-treatment and solvent/detergent treatments are both commonly used in the production of fibrinogen. Fibrinogen used in accordance with the present invention is preferably pure though other components may be present. Thus products may also contain tranexamic acid, aprotinin or factor XIII. Fibrinogen is commercially available from Baxter and Omrix.

As is mentioned before, the scaffold of the present invention is formed by cross-linking the polymer-protein precursor molecules of the present invention. Such cross-linking can be performed in vitro, ex vivo and/or in vivo.

Cross-linking according to this aspect of the present invention is performed by subjecting the precursor molecules to a free-radical polymerization reaction (i.e., a cross-linking reaction). Methods of cross-linking polymers are known in the art, and include for example, cross-linking via photoinitiation (in the presence of an appropriate light, e.g., 365 nm), chemical cross-linking [in the presence of a free-radical donor] and/or heating [at the appropriate temperatures. Preferably, cross-linking according to the present invention is effected by photoinitiation.

Photoinitiation can take place using a photoinitiation agent (i.e., photoinitiator) such as bis(2,4,6-trimethylbenzoyl) phenylphosphine oxide (BAPO) (Fisher J P et al., 2001; J. Biomater. Sci. Polym. Ed. 12: 673-87), 2,2-dimethoxy-2-phenylacetophenone (DMPA) (Witte R P et al., 2004; J. Biomed. Mater. Res. 71A(3): 508-18), camphorquinone (CQ), 1-phenyl-1,2-propanedione (PPD) (Park Y J et al., 1999, Dent. Mater. 15(2): 120-7; Gamez E, et al., 2003, Cell Transplant. 12(5): 481-90), the organometallic complex Cp'Pt(CH(3))(3) (Cp'=eta(5)-C(5)H(4)CH(3)) (Jakubek V, and Lees A J, 2004; Inorg. Chem. 43(22): 6869-71), 2-hydroxy-1,4-(hydroxyethoxy)phenyl]-2-methyl-1-propanone (Irgacure 2959) (Williams C G, et al., 2005; Biomaterials. 26(11): 1211-8), dimethylaminoethyl methacrylate (DMAEMA) (Priyawan R, et al., 1997; J. Mater. Sci. Mater. Med. 8(7): 461-4), 2,2-dimethoxy-2-phenylacetophenone (Lee Y M et al., 1997; J. Mater. Sci. Mater. Med. 8(9): 537-41), benzophenone (BP) (Wang Y and Yang W. 2004; Langmuir. 20(15): 6225-31), flavin (Sun G, and Anderson V E. 2004; Electrophoresis, 25(7-8): 959-65).

The photoinitiation reaction can be performed using a variety of wave-lengths including UV (190-365 nm) wavelengths, and visible light (400-1100 nm) and at various light intensities. It will be appreciated that for ex vivo or in vivo applications, the photoinitiator and wavelengths used are preferably non-toxic and/or non-hazardous.

For example, as is shown in Example 1 of the Examples section which follows, the PEG-fibrinogen precursor molecule was cross-linked by photoinitiation in the presence of Igracure™2959 and a non-toxic UV light illumination (e.g., 5 minutes at 365 nm wavelength, 4-5 mWatts/cm$^2$ intensity).

It will be appreciated that although the polymer-protein precursor molecules of the present invention (e.g., PEGylated fibrinogen) are capable of being cross-linked without the addition of a cross-linking molecule, cross-linking according to the present invention can also utilize a molecule capable of cross-linking the polymer-protein precursors. Such cross-linking molecules can be for examples, PEG, PEG-DA, PEG multi-Acrylate, and/or PEG-VS.

For example, as is shown in Example 1 of the Examples section which follows, a functionalized PEG molecule (e.g., PEG-DA) was used to enhance the cross-linking reaction.

The concentration of cross-linking molecules (e.g., PEG-DA) can affect the scaffold strength, flexibility, elasticity and biodegradability and determination of such a concentration depends on the scaffold application and is within the capabilities of those skilled in the arts. For example, excess of a cross-linking molecule is expected to result in smaller pores, more cross-linking sites, and higher scaffold strength and less flexibility. On the other hand, as is shown in FIGS. 18a-e, 19a-1 and Example 4 of the Examples section which follows, excess of PEG-DA (i.e., the cross-linking molecule of the present invention) resulted in reduced scaffold biodegradability as indicated by the reduced cell attachment and/or spreading. It will be appreciated that reduced biodegradability is probably a result of masking or modifying the protein binding sites or signals which are necessary for protein degradation.

According to a preferred embodiment of this aspect of the present invention, an excess of 3% PEG-DA is added in order to promote bone formation. The present inventors have shown that this concentration of excess PEG-DA provides the optimal biodegradability characteristics for the hydrogel regarding bone formation (FIGS. 20a-c and FIGS. 23a-c). Without being bound to theory, it is believed that a sustained release of fragments of PEGylated fibrinogen from the hydrogel synchronized with degradability is necessary to fully capitalize on the osteoinductive properties of the hydrogel of the present invention.

According to preferred embodiments of the present invention, cross-linking is effected such that the polymer-protein precursors of the present invention are solubilized in a water-based solution and such solutions are further subjected to cross-linking (e.g., using photoinitiation) to form a hydrogel scaffold.

As is shown in Example 1 of the Examples section which follows, a PEG-fibrinogen hydrogel was formed by mixing the PEGylated fibrinogen precursor molecules with the photoinitiation agent (Igracure™2959) in the presence or absence of PEG-DA and exposing such a mixture to UV light. Briefly, the PEGylated fibrinogen precursors were solubilized in 1-ml of 50 mM PBS, pH 7.4 and 25° C. to achieve a final concentration of 10, 15, or 20% polymer-protein (w/v). The precursor solution also contained a PEG-DA cross-linking constituent at a molar ratio of 1:2 PEG-DA to functional groups on the PEGylated fibrinogen. The precursor solution was mixed with 10 µl of Igracure™2959 photoinitiator solution (Ciba Specialty Chemicals, Tarrytown, N.Y.) in 70% ethanol (100 mg/ml) and centrifuged for 5 min at 14,000 RPM. The solution was then placed into Teflon tubes (5-mm diameter and 20-mm long) and polymerized under UV light (365 nm, 4-5 mW/cm$^2$) for 15 minutes according to published protocols (Lum L Y et al., 2003).

According to preferred embodiments of the present invention the hydrogel can be generated from PEGylated whole fibrinogen or PEGylated fragmented fibrinogen. Generally, the molecular weight and length of the grafted PEG affects the degree of solubility of the PEGylated protein, i.e., higher length and/or molecular weight of PEG results in increased solubility of PEGylated protein. It will be appreciated that solubility of the PEGylated protein is also affected by the presence of whole or cleaved fibrinogen. Preferably, the concentration of the precursor molecules in the hydrogel is between 0.5 to 35%, more preferably, when PEGylated whole fibrinogen is used, the concentration of the precursor molecules in the hydrogel is between 0.5 to 5% (depending on the MW and length of the grafted PEG used to PEGylate the protein) and when PEGylated fragmented fibrinogen is used, the concentration of the precursor molecules in the hydrogel is between 5-35% (depending on the MW and length of PEG used to PEGylate the protein).

The PEG-fibrinogen hydrogels of the present invention exhibited a superior flexibility over the prior art PEG-PEG hydrogels. For example, while in the PEG-PEG hydrogel (using 4 kDa PEG) a strain of 30% was achieved by employing a stress of 90 kPa, in the PEG-fibrinogen hydrogel (using 4 kDa PEG) a similar strain was achieved by employing only 4 kPa (FIGS. 3a-b and FIGS. 4a-c).

Preferably, the modulus of elasticity of the hydrogels made from PEGylated whole fibrinogen is in a range of 0.02-0.11 kPa for 10-20% polymer, and the modulus of elasticity of the hydrogels made from PEGylated fragmented fibrinogen is in a range of 0.01-0.07 kPa for 10-20% polymer.

In addition, the hydrogel scaffolds of the present invention exhibit high biodegradability as compared with prior art hydrogel scaffolds [e.g., hydrogels made with an oligopeptide cross-linker containing a protease substrate (Seliktar et al 2004)]. For example, as is shown in FIGS. 5a-b and Example 1 of the Examples section which follows, a significant degradation of 45-70% or 35-85% of the PEG-fibrinogen hydrogels was observed following 30 minutes incubation in the presence of 0.05 mg/ml trypsin or 0.5 mg/ml collagenase, respectively. Moreover, as is further shown in FIG. 5b, higher concentrations of trypsin (i.e., 1-2 mg/ml) resulted in a complete hydrogel degradation following 30 minutes of incubation.

Thus, the biodegradability of the hydrogel scaffold of the present invention can be determined by subjecting such hydrogels to enzymatic degradation using proteases such as plasmin, trypsin, collagenase, chemotrypsin and the like.

It will be appreciated that the biodegradability and biofunctionality of the scaffold hydrogel of the present invention can be further increased by loading with a pharmaceutical agent of interest.

Thus, for example, compositions of the present invention may enclose components which are nonreactive to the hydrogel. Examples of such nonreactive components may include drugs such as disinfectants, chemotherapeutics, antimicrobial agents, antiviral agents, hemostatics, antiphlogistics, anesthetics, analgesics, or nutritional supplements; biopolymers such as peptides, plasma derivative proteins, enzymes or mixtures thereof. In other words, components nonreactive to the hydrogel may be combined with the composition for hydrogel to provide stabilization or protection of these components. Such combined composition may be prepared, for example, by dissolving or suspending the nonreactive components in the aqueous medium to be used for gelation before effecting the gelation. Methods of loading hydrogels with pharmaceuticals are well known in the art [see for example, drug inclusion in bovine serum albumin hydrogels desrcribed in Gayet and Fortier (1995) Art. Cells. Blood Subs. And Immob. Biotech. 23(5), 605-611].

Alternatively or additionally, the biodegradability and biofunctionality of the scaffold hydrogel of the present invention can be further increased by attaching or impregnating a protein such as a cell signaling protein, or a growth factor (e.g. a nerve growth factor as described in Example 6 hereinbelow) to the hydrogel of the present invention. Attaching such proteins to the hydrogel scaffold of the present invention is preferably employed by covalent immobilization of a PEGylated protein to the PEG hydrogel network during cross-linking (Seliktar et al 2004, JBMR). The immobilization of such factor is accomplished by directly reacting functionalized PEG to an unreacted thiol present on a cysteine residue of the protein sequence. Impregnation of the hydrogel with growth factors can be performed by dehydrating the scaffold and then immersing the hydrogels in a solution containing the growth factors and gently shaking such hydrogels for a few hours until the growth factors penetrate the scaffold during the hydration process. Likewise, the hydrogel can be impregnated with growth factor by incubation in factor-containing solution overnight until the growth factor diffuses into the polymeric network of the scaffold by slow, passive diffusion.

The latter is influenced by the degree of cross-linking, the porosity of the scaffold, and the structural properties described hereinabove.

Apart from being inexpensive to produce, the scaffold of the present invention is highly reproducible, flexible (can be stressed or stretched easily), exhibit a controllable structural properties, and amenable to controllable biodegradation; characteristics which make it highly suitable for in vivo or ex vivo regeneration of tissues such as bone, nerve, cartilage, heart muscle, skin tissue, blood vessels, and other tissues (soft and hard) in the body. For example, such a scaffold hydrogel can be easily placed into gaps within a tissue or an organ, following which it can fill the void and initiate the process of regeneration as the scaffold degrades away.

Indeed, as is shown in FIGS. 8-17, FIGS. 20a-c and FIGS. 23a-c in Examples 3 and 5 of the Examples section which follows, implantation of the scaffold of the present invention in a critical size rat tibia defect resulted in new bone formation.

Thus, according to another aspect of the present invention there is provided a method of inducing in vivo formation of a tissue.

The phrase "in vivo" refers to within a living organism such as a plant or an animal, preferably in mammals, preferably, in human subjects.

The method is effected by implanting the scaffold of the present invention in a subject to thereby induce the formation of the tissue.

As used herein, the term "subject" refers to a vertebrate, preferably a mammal, more preferably a human being (male or female) at any age.

The scaffold of the present invention can be implanted in the subject using a surgical tool such as a scalpel, spoon, spatula, or other surgical device.

It will be appreciated that in vivo formation of a tissue can be also achieved by administering the scaffold precursor molecules to the subject and further cross-linking the precursor molecules in vivo.

Thus, according to another aspect of the present invention there is provided a method of inducing in vivo formation of a tissue. The method is effected by administering to a subject in need thereof a composition composed of a synthetic polymer attached to a naturally occurring protein or a portion thereof, the composition capable of forming a scaffold within the subject and thereby inducing the formation of the tissue in vivo.

As used herein "a composition composed of a synthetic polymer attached to a naturally occurring protein or a portion thereof" refers to the polymer-protein precursor molecule of the present invention which is described hereinabove.

According to preferred embodiments of the present invention, the method according to this aspect further comprises a step of cross-linking following administering the composition. Cross-linking can be performed as described hereinabove using non-toxic, non-hazardous agents and/or conditions.

According to preferred embodiments of this aspect of the present invention, the method further comprises administering to the subject a molecule capable of cross-linking the composition.

The phrase "molecule capable of cross-linking the composition" refers to the cross-linking agent described hereinabove (e.g., PEG-DA).

It will be appreciated that the scaffold of the present invention can be also used for ex vivo formation of a tissue. For example, the PEG-fibrinogen scaffolds of the present invention were shown to be capable of ex vivo nerve regeneration as illustrated in FIGS. 26-30 in Example 6.

Thus according to another aspect of the present invention there is provided a method of inducing ex-vivo formation of a tissue.

The phrase "tissue" refers to part of an organism consisting of an aggregate of cells having a similar structure and function. Examples include, but are not limited to, brain tissue, retina, skin tissue, hepatic tissue, pancreatic tissue, bone, nerve, cartilage, connective tissue, blood tissue, muscle tissue, cardiac tissue brain tissue, vascular tissue, renal tissue, pulmunary tissue, gonadal tissue, hematopoietic tissue and fat tissue. Preferably, the phrase "tissue" as used herein also encompasses the phrase "organ" which refers to a fully differentiated structural and functional unit in an animal that is specialized for some particular function. Non-limiting examples of organs include head, brain, eye, leg, hand, heart, liver kidney, lung, pancreas, ovary, testis, and stomach.

As used herein, the phrase "ex vivo" refers to living cells which are derived from an organism and are growing (or cultured) outside of the living organism, preferably, outside the body of a vertebrate, a mammal, or human being. For example, cells which are derived from a human being such as human muscle cells or human aortic endothelial cells and are cultured outside of the body are referred to as cells which are cultured ex vivo.

The method is effected by seeding the scaffold of the present invention with cells to thereby induce tissue formation.

The cells used by the present invention are capable of forming a tissue. Such cells can be for example, stem cells such as embryonic stem cells, bone marrow stem cells, cord blood cells, mesenchymal stem cells, adult tissue stem cells, or differentiated cells such as neural cells, retina cells, epidermal cells, hepatocytes, pancreatic cells, osseous cells, cartilaginous cells, elastic cells, fibrous cells, myocytes, myocardial cells, endothelial cells, smooth muscle cells, and hematopoietic cells.

The term "seeding" refers to encapsulating, entrapping, plating, placing and/or dropping cells into the scaffold of the present invention. It will be appreciated that the concentration of cells which are seeded on or within the scaffold of the present invention depends on the type of cells used and the composition of scaffold used (i.e., molar ratio between the synthetic polymer and protein within the precursor molecules and the percent of cross-linking molecule used).

It will be appreciated that seeding of the cells can be performed following the formation of the hydrogel scaffold of the present invention (i.e., on the casted hydrogel scaffold) or on pre-casted hydrogels, i.e., by mixing the cells with the scaffold precursor molecules prior to cross-linking the scaffold. The concentration of cells to be seeded on the hydrogels depends on the cell type and the scaffold properties and those of skills in the art are capable of determining the concentration of cells used in each case.

It will be appreciated that following seeding the cells on the scaffold, the cells are preferably cultured in the presence of tissue culture medium and growth factors.

For example, to induce the formation of a cartilage tissue, chondrocytes are seeded in the hydrogel scaffolds of the present invention (prior to cross-linking) at a concentration of approximately $15 \times 10^6$ cell/ml, following which the seeded scaffold is placed in a casting frame at room temperature and is further subjected to photoinitiation as described above. Following hydrogel casting, the seeded scaffold is transferred to a Petri dish containing tissue culture medium supplemented with serum (e.g., 10% FBS) and/or 1% ITS (insulin, transferrin, and selenium, Sigma), and is incubated at 37° C. for a few weeks, during which the culture medium is replaced every other day.

Following seeding the cells in the scaffold of the present invention the scaffolds are routinely examined using an inverted microscope for evaluation of cell growth, spreading and tissue formation (see for example FIGS. 18a-e and 19a-1).

Thus, the scaffold of the present invention which is formed in vitro, ex vivo or in vivo can be used to induce tissue formation and/or regeneration and thus treat individuals suffering from tissue damage or loss.

Thus, according to another aspect of the present invention there is provided a method of treating a subject having a disorder characterized by tissue damage or loss.

As used herein the phrase "disorder characterized by tissue damage or loss" refers to any disorder, disease or condition exhibiting a tissue damage (i.e., non-functioning tissue, cancerous or pre-cancerous tissue, broken tissue, fractured tissue, fibrotic tissue, or ischemic tissue) or a tissue loss (e.g., following a trauma, an infectious disease, a genetic disease, and the like) which require tissue regeneration. Examples for disorders or conditions requiring tissue regeneration include, but are not limited to, liver cirrhosis such as in hepatitis C patients (liver), Type-1 diabetes (pancreas), cystic fibrosis (lung, liver, pancreas), bone cancer (bone), burn and wound repair (skin), age related macular degeneration (retina), myocardial infarction, myocardial repair, CNS lesions (myelin), articular cartilage defects (chondrocytes), bladder degeneration, intestinal degeneration, and the like.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

The method is effected by implanting the scaffold of the present invention alone or following seeding such a scaffold with cells, or by administering the scaffold units (i.e., the polymer-protein precursor molecules of the present invention) into the subject to thereby induce formation of the tissue and treat the disorder characterized by tissue damage or loss.

It will be appreciated that the cells seeded on the scaffold for ex vivo formation of a tissue can be derived from the treated individual (autologous source) or from allogeneic sources such as embryonic stem cells which are not expected to induce an immunogenic reaction.

Following ex vivo tissue formation the seeded scaffold is implanted in the subject. Those of skills in the art are capable of determining when and how to implant the scaffold to thereby induce tissue regeneration and treat the disease. For example, if the disease to be treated is articular cartilage the scaffold is seeded with chondrocytes and following 14-21 days in culture the scaffold is preferably implanted in the articular surface of the joint thereafter. Alternatively, the scaffold can be injected as a precursor solution, with or without cells, and polymerized directly in the site of the cartilage damage. The polymerized hydrogel fills the gap of the defect and initiates the regeneration of new cartilage tissue.

Compositions of the present invention may, if desired, be presented in a pack or dispenser device, such as an FDA-approved kit, which may contain one or more unit dosage forms (e.g., 100 mg) such as for personalized use containing the active ingredient (e.g., precursor molecules which are not yet cross-linked such as PEGylated denatured fibrinogen) and optionally sterile disposable means for delivery (e.g., syringe) and for illumination (e.g., illuminator covers). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

It is expected that during the life of this patent many relevant polymer-protein scaffolds will be developed and the scope of the term scaffold is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed.

(1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of PEG-Fibrinogen Hydrogels

Tissue engineering scaffolds with controllable mechanical properties and adequate biofunctional signals were generated from PEG and fibrinogen. Briefly, denatured fibrinogen fragments were PEGylated with PEG-diacrylates, mixed with photoinitiator and exposed to UV light to form a hydrogel material in the presence of a cell suspension. The degradability of the PEG-fibrinogen scaffold was further tested by enzyme-mediated proteolysis, as follows.

Materials and Experimental Methods

Synthesis of PEG Diacrylate (PEG-DA)

PEG-diacrylate (PEG-DA) was prepared from linear PEG, MW=4-kDa, 6-kDa, and 20-kDa (Fluka, Buchs, Switzerland), essentially as described elsewhere (Lutolf and Hubbell, 2003; Elbert D L., et al., 2001). Briefly, acrylation of PEG-OH was carried out under Argon by reacting a dichloromethane (DCM) (Aldrich, Sleeze, Germany) solution of the PEG-OH with acryloyl chloride (Merck, Darmstadt, Germany) and triethylamine (Fluka) at a molar ratio of 1-OH to 1.5-acryloyl chloride to 1.5-triethylamine (0.2 g PEG/ml DCM). The final product is precipitated in the presence of ice-cold diethyl ether and dried under vacuum overnight. The degree of end-group conversion was confirmed by $^1$H NMR and was found to be 97-99% (data not shown).

Cyanogen Bromide Cleavage of Fibrinogen

Whole fibrinogen [Sigma-Aldrich, Steinheim, Germany, Cat # F8630, GenBank Accession No. AAC67562.1. (α-chain; SEQ ID NO:1); GenBank Accession No. CAA23444.1 (β-chain; SEQ ID NO:2), and GenBank Accession No. CAA33562.1 (γ-chain; SEQ ID NO:3)] was dissolved in a solution of 70% formic acid containing 17 mg/ml Cyanogen Bromide (CNBr) (Aldrich, Cat. # C9, 149-2) and incubated overnight in the dark at 25° C. The cleaved fibrinogen fragments were dialyzed for 2 days at 4° c. in 50 mM phosphate buffered saline (PBS) at pH 7.4 with a twice-daily change of buffer to remove all the CNBr and formic acid from the solution. The dialyzed fragments were stored in PBS at 4° C. until they were subjected to PEGylation. Since grafting of PEG has a detectable effect on the mobility of the protein in acrylamide gels (Kurfurst M M, 1992; Pomroy N C and Deber C M, 1998), visualization of the PEGylated fibrinogen fragments was performed by loading the samples on an SDS-PAGE followed by a Coomassie®-blue staining.

PEGylation of Fibrinogen

To PEGylate the fibrinogen protein, tris (2-carboxyethyl) phosphine hydrochloride (TCEP.HCl) (Sigma) was added to a 7 mg/ml solution of fibrinogen in 50 mM PBS with 8 M urea (molar ratio 68:1 TCEP to fibrinogen cysteins) and the solution was left shaking for 15 min at 25° C. until fully dissolved. After dissolution of the fibrinogen, a solution of PEG-DA (250-300 mg/ml) in 50 mM PBS and 8 M urea was added to the fibrinogen and reacted overnight in the dark at 25° C. The molar ratio of PEG to fibrinogen was 145:1 (linear PEG-DA, MW 4-kDa, 6-kDa, and 20-kDa). The final PEGylated protein product was precipitated for 20 minutes at room temperature while stirring in 5× excess acetone (Frutarom, Haifa, Israel). The precipitated protein solution was centrifuged for 20 minutes at 5000 RPM (Sorvall GSA rotor) and the pellet was redissolved at 20 mg/ml protein concentration in PBS containing 8 M urea. The PEGylated protein solution was then dialyzed for 2 days at 4° C. against PBS containing 0.1% (v/v) glacial acetic acid (Frutarom) with twice-daily changes of PBS (Spectrum, 12-14-kDa MW cutoff). The dialyzed product was either used immediately or lyophilized in a solution of 10% D-(+)-glucose (Riedel-deHaen, Germany) to improve solubility upon redissolution. The lyophilized PEGylated product was stored under Argon at −80° C. for up to six months.

Photo-Polymerization of PEG Hydrogels

The PEG-fibrinogen hydrogels were made from a precursor solution of PEGylated fibrinogen (whole or cleaved). The precursor solution was made by solubilizing PEGylated fibrinogen in 1 ml of 50 mM PBS, pH 7.4 and 25° C. to achieve a final concentration of 10, 15, or 20% polymer (w/v). The precursor solution also contained a PEG-DA cross-linking constituent at a molar ratio of 1:2 PEG-DA to functional groups on the PEGylated fibrinogen. The additional PEG-DA was used to efficiently cross-link the PEGylated protein macromeres and minimize steric hindrances that result in poor gelation. The precursor solution was mixed with 10 µl of Igracure™2959 photoinitiator solution (Ciba Specialty Chemicals, Tarrytown, N.Y.) in 70% ethanol (100 mg/ml) and centrifuged for 5 min at 14,000 RPM. The solution was then placed into Teflon tubes (5-mm diameter and 20-mm long) and polymerized under UV light (365 nm, 4-5 mW/cm$^2$) for 15 minutes according to published protocols (Lum L Y et al., 2003). Following polymerization, the hydrogels were cut into 5-mm long sections for mechanical testing. Control hydrogels were made by solubilizing 10, 15, or 20% (w/v) PEG-DA in 1-ml of 50 mM PBS with Igracure™ and then polymerizing under UV light as described above.

Mechanical Properties Testing

The compressive mechanical properties of the acellular PEG-fibrinogen hydrogels were evaluated using an Instron™ 5544 single column material testing system with Merlin software. The stress-strain characteristics of 5-mm diameter plugs (5-mm long) were measured by constant straining (0.025 mm/sec) between two rigid, non-porous fixtures (unconfined). The material was strained to 30% strain and the force-displacement was recorded. The Merlin software automatically converted the raw data into a stress-strain relationship describing the material. The elastic modulus was determined directly from the stress-stain data as the average slope of the lower portion of the stress-strain curve (<15% strain).

Biodegradation Assay

To assess the rate of enzymatic hydrogel degradation, Coomassie® brilliant blue G-250 dye (Aldrich) was bound to the PEG-fibrinogen hydrogels and the release of the Coomassie® dye was measured spectrophotometrically. Hydrogels were stained in 0.1% Coomassie® (w/v) overnight with gentle agitation, and destained for 1 hour in destaining buffer. Since the Coomassie® dye binds to proteins with very high affinity, following the initial staining, the hydrogels were destained to release all unbound dye. The gels were then transferred to multiwell plates and incubated with known concentrations of Collagenase (Sigma) or trypsin (BD Biosciences, Sparks, Md.) in PBS. The enzymatic degradation by Collagenase and trypsin was correlated to the release of Coomassie®-bound fibrinogen from the hydrogel network following a 24 hours incubation period. Samples of supernatant (350 µL) were transferred to a quartz cuvette and were measured using the UV/Vis spectrophotometer (Hitachi Instruments Inc., USA). All data was normalized with the spectrophotometric measurements of hydrogels degraded completely by their respective enzyme.

Statistical Analysis

Statistical analysis was performed using the statistical analysis features of Microsoft Excel. Data from at least two independent experiments were quantified and analyzed for each variable. Comparisons between multiple treatments were made with analysis of variance (ANOVA) while comparisons between treatments were made using a two-tail student t-test with $P<0.05$ considered statistically significant.

Experimental Results

PEGylation of Fibrinogen can be Performed Using 4-kDa, 6-kDa and/or 20-kDa PEG-DA The PEG-fibrinogen hydrogels were prepared by covalently binding protein fragments to PEG-DA and cross-linking by UV photoinitiation. FIG. 1a illustrates the potential of the fibrinogen constituent to be linked to fractionalized PEG. A Michael-type addition reaction (Lutolf M et al, 2001, Bioconjugate chem. 12(6):1051-6) was used to form an ester bond between the free thiol groups in the fibrinogen cysteines and the acrylate end-groups on the PEG-DA (i.e., PEGylation reaction) using varying molecular weight fragments of 4-kDa, 6-kDa, and 20-kDa of PEG-DA.

To further confirm the presence of PEGylated fibrinogen fragments and to determine the optimal conditions for the PEGylation reaction, the reaction products were subjected to an SDS-PAGE followed by Coomassie®-blue staining. As is shown in FIG. 2a, following incubation of whole fibrinogen with a 4-kDa PEG-DA fragment, a time-dependent shift to higher molecular weight fragments was observed. Thus, while following one hour of incubation with the 4-kDa PEG-DA, many of the fragments were elevated above 60 kDa, following two hours and/or overnight incubations most of the fragments were larger than 250 kDa. Moreover, as is shown in FIG. 2b, when CNBr-cleaved fibrinogen was incubated with either the 4-kDa or the 6-kDa PEG-DA fragments, a considerable shift to higher molecular weight fragments was observed within one hour of incubation.

These results clearly demonstrate that PEGylation of fibrinogen is more efficient on CNBr-cleaved fibrinogen than on whole fibrinogen. In addition, these results show that PEGylation of fibrinogen is a time-dependent reaction.

The PEG Fibrinogen Product Exhibits High Percentage of PEGylated Fibrinogen

Following an overnight PEGylation reaction the PEGylated fibrinogen product is purified using acetone precipitation which selectively precipitates the protein (i.e., PEGylated fibrinogen) from the excess of unreacted PEG-DA. It is worth mentioning that the addition of acetone at room temperature to the PEG-DA reaction [using an iodide solution as described elsewhere (24)] did not result in the precipitation of free, unreacted PEG-DA (data not shown). It will be appreciated that excess of unreacted PEG can theoretically become entangled with grafted PEG chains on the PEGylated protein and thus remain part of the PEGylated protein during precipitation. To confirm the purity of the PEGylated fibrinogen, the dry weight of the total PEGylated product was compared with the amount of total protein as measured using a Pierce BCA assay in a purified solution of PEGylated fibrinogen. The dry weight of PEGylated protein should be the sum of the weights of the fibrinogen and the grafted PEG, assuming 100% PEGylation. The theoretical protein fractions for PEGylated fibrinogen using 4-kDa, 6-kDa, and 20-kDa PEG (assuming 100% PEGylation and 100% purity) are 59%, 49%, and 22%, respectively. The results indicate a protein fraction of 45±5.0% using the 4-kDa PEG, 39±3.4% using the 6-kDa PEG, and 36±1.5% using the 20-kDa PEG. The difference between the theoretical and the measured protein factions can be attributed to several factors, including excess of unreacted PEG, partial PEGylation, and/or error in the BCA measurements. It is worth mentioning that excess of unreacted PEG was not visible in SDS-PAGE stained with iodine-acetate (data not shown), thus confirming the observation that the fibrinogen is highly PEGylated after an overnight reaction with PEG-DA. Thus, these results suggest that the deviation from the expected protein fractions result from either partial PEGylation or errors in the determination of protein concentrations using the BCA assay.

Cyanogen Bromide Cleavage of Fibrinogen Facilitates the Preparation of PEGylated Fibrinogen Solutions Since the combination of the highly hydrophilic PEG to the partially hydrophobic fibrinogen can result in a highly hydrophobic protein core, the fibrinogen molecule was denatured prior to being subjected to the PEGylation reaction. Such denaturation minimizes the formation of the hydrophobic core after PEGylation and significantly improves the solubility of the product. Denaturation of the fibrinogen molecule was accomplished using CNBr, a proteolytic molecule which chemically cleaves adjacent to methionine peptides in the fibrinogen sequence. CNBr cleavage of bovine fibrinogen (3 parts fibrinogen to 2 parts CNBr) results in 30 fragments (F1-F30) ranging in size from 35-kDa to 0.1-kDa each. Eight of these fragments contain two or more unpaired thiol groups which are capable of contributing to the structure of the hydrogel network (see Tables 1 and 2, hereinbelow). FIG. 2a demonstrates the presence of small fragments of fibrinogen before and after PEGylation using SDS-PAGE. In addition, the PEGylated CNBr-cleaved fibrinogen fragments exhibit the same PEGylation efficiency and protein purity as the whole PEGylated protein after acetone precipitation (data not shown). Thus, using the method of the present invention, PEGylated fibrinogen solutions with concentrations of up to 300 mg/ml were prepared under non-denaturing conditions.

TABLE 1

Fibrinogen fragments and cysteines from whole fibrinogen

| Fragments | Alpha | beta | gamma | Total |
| --- | --- | --- | --- | --- |
| M.W. | 65 | 53.3 | 47.6 | 165.9 |
| Cysteines | 8 | 11 | 10 | 29 |

TABLE 2

Fibrinogen fragments and cysteines from multi thiol fragments of cleaved fibrinogen

| | Fragments | | | | | | | |
| --- | --- | --- | --- | --- | --- | --- | --- | --- |
| | F1 | F2 | F3 | F4 | F7 | F8 | F15 | F16 | Total |
| M.W. | 32.4 | 24.6 | 12.1 | 10 | 7 | 6.3 | 3.8 | 3.8 | 100 |
| Cysteines | 2 | 4 | 3 | 4 | 2 | 2 | 4 | 4 | 25 |

PEG-Fibrinogen Hydrogels are Highly Elastic

To confirm formation of hydrogels from the PEGylated protein precursors, the compressive mechanical properties of the material were measured using the Instron™ single column material testing system. These measurements confirmed the formation of acellular PEG-fibrinogen hydrogels (and PEG-PEG controls) with varying amounts of polymer (10%, 15%, and 20% w/v) and different molecular weights of PEG (4-kDa and 6-kDa, 20-kDa) as well as the formation of hydrogels which are made of either whole fibrinogen (whole) or CNBr-cleaved fibrinogen (cleaved). Further measurements of the stress-strain characteristics of the PEG hydrogels demonstrated that the stress-strain characteristic of both PEG-PEG and PEG-fibrinogen hydrogels is non-linear and highly dependent on the molecular weight of the PEG precursor (FIGS. 3$a$ and $b$). In addition, as is shown by the stress-strain graphs (FIGS. 3$a$-$b$), the modulus of elasticity observed in the PEG-fibrinogen hydrogels (in the range of 0.12-0.14) was significantly lower than that of the PEG-PEG hydrogels (in the range of 2.5-3.21). In addition, the elastic modulus (as determined from the stress-strain curve) was found to be dependent on the percent polymer, the molecular weight of the PEG precursor, and the fibrinogen backbone (FIGS. 4$a$-$c$). In general, the elastic modulus of the PEG-PEG hydrogels (at any given percent polymer concentration) was found to be significantly higher than that of the PEG-fibrinogen hydrogels (n=5, p<0.05). Likewise, the elastic modulus of PEG-fibrinogen hydrogels made with whole fibrinogen was found to be significantly different than that of the hydrogels made with cleaved fibrinogen (n=5, p<0.05).

Biodegradation of PEG-Fibrinogen Hydrogels is Dependent on the MW of the PEG Component and the Protein Backbone Hydrogel biodegradation was quantified by subjecting colorimetrically-labeled pure PEG-fibrinogen hydrogels (15% w/v PEG-DA, MW 6-kDa) to varying concentrations of proteases (e.g., Collagenase or trypsin) and assessing the dissolution of the gels. Thus, as the hydrogel dissolves, fragments released into an overlaying buffer are quantified using a spectrophotometer. As is shown in FIG. 5$a$, degradation of the PEG-fibrinogen hydrogels was affected by both the MW of the grafted PEG and the molecular structure of the protein backbone of the hydrogel. Thus, changing the PEG MW from 6-kDa to 20-kDa resulted in accelerated degradation in the presence of 0.05 mg/ml trypsin (n=6, p<0.05) but not in the presence of 0.5 mg/ml Collagenase. Likewise, the degradation of the cleaved fibrinogen hydrogels in 0.5 mg/ml Collagenase was significantly higher than that of the whole fibrinogen hydrogels (n=6, p<0.05). As is shown in FIG. 5$b$, increasing concentrations of either trypsin or Collagenase resulted in higher percent degradation of the hydrogels. Similar results were obtained by analyzing the degraded PEGylated fibrinogen hydrogels on SDS-PAGE (data not shown).

Altogether, these results demonstrate the generation of unique PEG-fibrinogen hydrogels which provide distinct advantages over other scaffold materials: (i) the mechanical properties of the PEG-hydrogels are highly malleable; (ii) the biological functionality is maintained by the protein backbone of the polymeric network; and (iii) the elastic modulus of the PEG-fibrinogen hydrogel is dependent on the molecular weight of the PEG constituent and proportional to the percent polymeric composition.

Analysis and Discussion

The use of protein-based synthetic materials is a novel approach to designing the "next-generation" of hydrogel scaffolds for tissue engineering (16, 23, 26-30). These materials are capable of promoting cell growth and exhibit proteolytic degradability via their biological domains while still providing exacting mechanical properties based on their synthetic composition. A number of these hybrid hydrogel materials are currently in use as ingrowth matrices or cell culture substrates which take advantage of biologically active oligopeptides in the material backbone that mimic the properties of natural tissue (17, 18). While these materials satisfy the general criteria of biofunctionality, the small oligopeptides provide only a fraction of the bioactive signals present in the natural extracellular matrix (ECM). To overcome this limitation, some approaches use recombinant DNA technologies to create an engineered protein-like backbone with inherent bioactivity (16), while other approaches add bioactive growth factors that are either covalently (23, 27, 31) or non-covalently (32) immobilized into the material.

The hydrogel material of the present invention contains a natural protein backbone onto which di-functional PEGs are covalently bound and cross-linked together using photo-polymerization. The protein backbone is comprised of alpha, beta, and gamma fragments of denatured fibrinogen. These fibrinogen fragments are inherently bioactive with proteolytically sensitive sequences, cell adhesion motifs, and other cell-signaling sequences (14). Free thiol groups present in unpaired cysteine residues in the denatured fibrinogen fragment are covalently conjugated by a Michael-type addition reaction to an unsaturated double bond on functionalized PEG-DA. The hydrogel material of the present invention uses denatured fibrinogen since it consists of a large number of free thiol groups (i.e., unpaired cysteine residues) that can react with PEG-DA. After PEGylation, unreacted acrylates on the di-functional PEGs are used to cross-link the fibrinogen backbone into a hydrogel network using photo-polymerization.

The molecular structure of the hydrogels is highly influenced by the degree of cross-linking. In addition to the percent polymer, the other crucial determining factor of the hydrogel cross-linking is the ratio of reactive acrylate end-groups on the PEG per MW of protein (acrylates per kDa of PEGylated protein). Assuming that each PEG is bound to fibrinogen with one acrylate end-group, fully PEGylated fibrinogen contains 29 acrylate groups for each molecule of protein, or approximately 0.1 acrylate/kDa for 4-kDa PEGylated fibrinogen, 0.086 acrylate/kDa for 6-kDa PEGylated fibrinogen, and 0.039 acrylate/kDa for 20-kDa PEGylated fibrinogen. A pure PEG-DA solution contains 0.5 acrylates/kDa for 4-kDa PEG, 0.33 acrylates/kDa for 6-kDa PEG, and 0.1 acrylates/kDa for 20-kDa PEG. If the ratio of acrylates to MW is too low, the polymer solution will not form a continuous hydrogel. For this reason, the experiments performed in the present study utilized high concentrations of PEGylated fibrinogen (≥10%).

The PEGylated fibrinogen requires substantial effort to solubilize at these high concentrations. Since the solubility of the PEGylated fibrinogen is highly affected by the grafting of the PEG chains; presumably because of the formation of a hydrophobic protein complex in the presence of a highly hydrophilic PEG graft, the fibrinogen protein used by the present invention utilized an irreversibly cleaved by CNBr. Thus, PEGylation of cleaved fibrinogen results in a highly soluble protein precursor for hydrogel formation.

The mechanical properties of the cleaved and whole PEG-fibrinogen hydrogels was characterized using the stress-strain behavior under quasi-static uniaxial unconfined compression. The PEG-fibrinogen material demonstrates the typical non-linear stress-strain characteristics of a polymeric material, similar to the PEG-PEG control gels. The composite behaves like a viscoelastic solid with minimal hysteresis under repetitive cyclic loading (data not shown). The material stiffness, as determined from the modulus of elasticity, is directly proportional to the percent polymer composition. It will be appreciated that the material stiffness of polymeric hydrogels can be directly attributed to the degree of cross-linking. In the PEG-fibrinogen polymer, the amount of functional groups available for cross-linking is proportional to the polymer concentration. Thus, the modulus of the material is directly proportional to the amount polymer in the hydrogel.

The relationship between the elastic modulus of the hydrogel and the molecular chain length of the grafted PEG constituent is ambiguous. While pure PEG hydrogels exhibit a proportional relationship between the material modulus and the MW of the PEG, the addition of the protein into the hydrogel network can have a profound impact on this relationship, depending on the relative size of the two polymers. In the case of whole PEGylated fibrinogen hydrogels, where the PEG is significantly smaller than the protein, the impact of PEG MW on the modulus is more pronounced. In contrast, the relationship between PEG MW and the modulus of the hydrogels is less pronounced when the hydrogels are made of cleaved protein. In either case, it is difficult to resolve the difference between 4-kDa PEG and 6-kDa PEG when comparing the elastic moduli.

The mechanical properties data demonstrate a significant difference in the stiffness of hydrogels made from pure PEGylated fibrinogen versus pure PEG hydrogels. Irrespective of the PEG MW, the PEGylated fibrinogen hydrogels are always less stiff than the pure PEG hydrogels. This can be attributed to the fact that pure PEG hydrogels (made with similar weight percent of polymer) contain nearly 5 times more functional groups available for cross-linking than the PEGylated hydrogels. The discrepancy in cross-linking sites arises from the fact that the fibrinogen constituent accounts for more than half the weight of the polymer but does not contain inherent cross-linking sites, and each grafted PEG on the PEGylated fibrinogen only has a single functional group available for cross-linking, in contrast to two functional groups on free PEG-DA. Additional cross-linking limitations may arise because of steric hindrances caused by the bulky PEGylated fibrinogen molecules.

The addition of free PEG-DA to the PEGylated fibrinogen hydrogels introduces cross-linking sites to the hydrogel network and alters the material stiffness accordingly. Therefore, the balance between PEGylated fibrinogen and the additional free PEG-DA can be used to modulate the stiffness of the hydrogels without compromising the biofunctional domains of the fibrinogen constituent. It is important to note that the addition of free PEG to the PEGylated fibrinogen hydrogel can have a significant impact on the degradability of the hydrogels in the presence of cell-secreted proteases (data not shown).

Based on these findings, it is clear that the molecular chain length and percent composition represent two independent parameters to control the mechanical properties of the material. An additional parameter which can alter the mechanical properties of the material is the number of cross-linking sites on each grafted PEG molecule. As eluded to earlier, the linear grafted PEG contains only one functional group for cross-linking the hydrogel; however, PEG molecules containing several functional groups such as star-PEGs can also be grafted onto the fibrinogen to form hydrogels. While star-PEG was not used as part of the current investigation, future studies aim to increase the stiffness of the PEG-fibrinogen hydrogels using 4-arm and 8-arm star-PEG precursors.

The fibrinogen backbone of the hydrogel material provides proteolytic sensitivity via naturally occurring substrates for fibrinolysis. Fibrinolysis is a physiological process whereby the native fibrin molecule is proteolytically dismantled by serine proteases. In theory, the fibrinogen backbone is cleaved in the presence of activated proteases, resulting in complete dissolution of the PEG-fibrinogen hydrogel. The results shown in the present study demonstrate that pure PEG-fibrinogen hydrogels are proteolytically degradable while the PEG-PEG controls are not susceptible to proteolysis (data not shown).

The degradation data reveals several other interesting patterns regarding the proteolytic degradation of cleaved and whole fibrinogen hydrogels in the presence of trypsin or Collagenase after 30 minutes. Cleaved fibrinogen presents less substrate for degradation thereby increasing the normalized dissolution of the hydrogel in Collagenase (n=5, $p<0.05$). In trypsin, the cleaved and whole fibrinogen hydrogels degrade almost identically. This is likely explained by the observation that 0.05 mg/ml trypsin is saturated with substrate whereas 0.5 mg/ml collagenase is not saturated with substrate. Evidently, the MW of the PEG constituent also affects the degradation results. In trypsin, the 20-kDa PEG hydrogels are significantly more degraded than 6-kDa PEG hydrogels after 30 min, while in Collagenase there is no significant difference in the degradation between the two conditions (n=6, $p<0.05$). The 20-kDa PEG hydrogels are comprised of less fibrinogen which results in faster hydrogel dissolution. This can also be explained by the observation that 0.05 mg/ml trypsin is saturated with enzyme and cannot degrade the 20-kDa PEGylated fibrinogen hydrogels faster. Future studies will examine more aspects of proteolytic degradability of the PEG-fibrinogen material, including degradation kinetics and fibrinolysis in the presence of plasmin.

Example 2

The PEG-Fibrinogen Hydrogels Support Cell Spreading and Extension

To test the capacity of the PEG-fibrinogen hydrogels to promote the expansion and differentiation of cell cultures, cell of bovine aortic endothelial cells and smooth muscle cells were cultured on various PEG-based hydrogels, as follows.

Materials and Experimental Methods

In Vitro Cell-Culture Studies

Bovine aortic smooth muscle cells (BSMCs) from young donors were isolated and cultured according to a modified protocol of Oakes et al., 1982. The BSMCs were cultured up to $6^{th}$ passage in Dulbecco's Modified Eagle Medium (DMEM) (Gibco, U.K.) containing 10% fetal bovine serum (FBS) (Biological Industries, Israel), 1% penicillin-streptomycin (Biological Industries), and 1% L-glutamine (Gibco). PEG hydrogels containing BSMCs were made by mixing a PBS cell suspension and PEGylated fibrinogen precursor solution containing Igracure™ photoinitiator to make a 10% (w/v) solution with $1.5 \times 10^6$ cells/ml. Aliquots of 100 μl of the suspension were added into wells in a flat-bottom 96-well plate and placed under UV-light (4-5 mW/cm$^2$) for 5 min in a laminar flow hood. DMEM culture medium (containing 10% FBS) was added immediately to the polymerized hydrogels and changed daily (100-μl/well).

Viability Studies of Cells Following Exposure to UV Light

To verify that the exposure to UV light did not damage the cells in the hydrogel, bovine aortic endothelial cells (BAECs) were isolated and cultured up to $6^{th}$ passage according to published protocols (Remuzzi A., et al., 1984). The BAECs were seeded and cultured on top of 1-mm thick PEG hydrogels in 24-well plates as described elsewhere (Seliktar D., et al., 2004). The seeding density of BAECs was 30,000 cells/cm$^2$. BAECs and BSMCs were monitored daily using a Nikon TE2000 phase-contrast microscope and digitally imaged with a digital CCD camera (Jenoptik, Germany).

Histological Evaluations

The cellularized PEG-fibrinogen hydrogels were frozen in liquid nitrogen-cooled 2-methylbutane (J. T. Baker, Phillipsburg, N.J.) and cut in 7 μm-thick sections using a cryostat. The sections were fixed onto glass microscope slides with ice-cold acetone and stained with Hematoxylin and Eosin (H&E) to visualize cell morphology. Cell morphology was documented using a Nikon light microscope (TS-100) connected to a digital imaging workstation (Sony Corporation, Japan).

Experimental Results

PEG-Fibrinogen Hydrogels Support Cell Spreading and Attachment

To test the capacity of the PEG-fibrinogen hydrogels to support three-dimensional spreading and attachment, endothelial (BAECs) or smooth muscle (BSMCs) cells were cultured on the surface of or inside the PEG hydrogels. BAECs were seeded on the surface of the hydrogels at a concentration of 30,000 cells/cm$^2$ and 24 hours following cell seeding the degree of cell attachment and spreading was evaluated using phase contrast microscopy. As is shown in FIGS. 6a and d, while BAECs grown on PEG-fibrinogen hydrogels exhibited significant cell attachment and spreading (FIG. 6a), BAECs cells grown on PEG-PEG hydrogels were round and devoid of any visible spreading (FIG. 6d). These results demonstrate the superior capacity of the PEG-fibrinogen to support cell adhesion or spreading over the PEG-PEG hydrogels. The capacity of the PEG-fibrinogen hydrogels to support three-dimensional spreading and attachment of cells was further tested dispersing BSMCs cells into the precursor solution (1.5×10$^6$ cells/ml, 4-kDa PEG, 10% polymer) prior to photopolymerization. After assembly, the hydrogel network contained homogeneously distributed BSMCs with round morphology. However, following 24 hours of culturing, BSMCs cultured inside the PEG-fibrinogen hydrogels formed stable adhesions, processes, and cellular extensions (FIGS. 6b-c). In addition, PEGylated fibrinogen hydrogels made with cleaved fibrinogen also supported the adhesion and extension of BSMCs inside PEGylated hydrogels (data not shown). In contrast, BSMCs cultured inside PEG-PEG hydrogels were round and devoid of any visible cell extensions (FIG. 6e). Further histological evaluation of the cultured BSMCs within the PEG hydrogels confirmed the observation that BSMCs are extended within the PEG-fibrinogen hydrogel network (FIG. 7a), but not within the PEG-PEG control hydrogels (FIG. 7b).

Analysis and Discussion

The PEG hydrogel scaffold without the fibrinogen backbone is completely devoid of biofunctional domains for cell culture. The fibrinogen backbone provides at least two biofunctional characteristics to the hydrogel material: proteolytic sensitivity and cell adhesivity. With regards to the latter, the PEG-fibrinogen hydrogels support the attachment and spreading of endothelial cells in the presence of serum proteins whereas PEG-PEG controls are not able to support cell attachment. Endothelial cell-surface adhesion molecules can therefore attach either directly to adhesion domains on the fibrinogen backbone or to other serum proteins that interact non-specifically with the fibrinogen. Once attached, cells are capable of proteolytically tunneling through the hydrogel network with the help of cell-secreted enzymes such as Collagenase. This is best exemplified with smooth muscle cells that are three-dimensionally entrapped inside the hydrogel material after photopolymerization and begin to form clusters of cells after 24 hours in culture. Phase contrast micrographs and histological cross-sections confirm that BSMCs form flagella-like extensions which enable their migration inside the hydrogel network. In this regards, there are no observed differences between the whole and cleaved fibrinogen hydrogel scaffolds. In contrast, BSMCs remained round and homogeneously dispersed and cell extensions are not observed in the non-degradable PEG-PEG controls.

Thus, the biological domains in the fibrinogen backbone provide attachment motifs for endothelial cell and smooth muscle cell adhesion as well as proteolytic sensitivity for biodegradation. Smooth muscle cells demonstrate the ability to proteolytically penetrate through the hydrogel material and form interconnecting networks of cells. Thus, the scaffolds of the present invention are novel, biodegradable and highly suitable for cultivating cells in a 3-D environment for tissue regeneration therapies.

Example 3

In Vivo Regeneration of Bone Using the PEG-Fibrinogen Gelrin™ Scaffold

To test the potential of the PEG-fibrinogen scaffold material to facilitate tissue regeneration, a critical size tibial defect was introduced in rats and the Gelrin™ scaffold was implanted at the site of surgery (tibia diaphysis).

Materials and Experimental Methods

Animals

Female Sprague-Dawley rats (age 3-4 months) were adapted to animal cage life for 5 days prior to the experiment. The weight of the animal was monitored during this period to ensure stability and proper adaptation. The animals were fed and watered daily without restrictions.

Introduction of a Critical Size Tibia Defect

The animals were anesthetized with a combination of Ketamine (120 mg/kg) and Xylazine (17 mg/kg). During the surgical procedure the animals were placed on a warm plate to maintain body temperature (and prevent hypothermia). The right tibia was shaved and wiped with polydine tincture solution. The mid-portion of the right tibia was exposed from the anterior medial side by longitudinal incision (FIG. 8a). An external fixator was placed proximal and distal to the mid-section of the tibia (FIG. 8b). Two needles were drilled into the proximal tibia (21G) and distal tibia (23G) and connected to two external fixators (screws) to form a stable fixation of the bone. A 10-mm gap was excised using a disk saw in the portion between the proximal and distal needles of the fixators (FIG. 8c). The fibula was not osteotomized.

Implantation of a PEG-Fibrinogen (Gelrin™) Scaffold

A PEG-fibrinogen plug (5-mm diameter and 10-mm long) was inserted into the defect site and the surrounding connective tissue was wrapped around to secure the plug into place (FIG. 8d). The incisional wound was sutured using nylon surgical thread. The animal was given prophylactic antibiotics (ampicilline 0.1 gram/100 gram). Immediately following surgery, the animal was x-rayed and further evaluated weekly by x-ray screening. The animal was free to move about the cage during the entire post-operative follow-up period. At the end of the 2-month evaluation period, the animal was sacrificed with $CO_2$ and the right tibia was harvested for histology and mechanical testing.

Experimental Results

Introduction of a critical size rat tibia defect is known to result in up to 20% mortality. A critical rat tibia defect was introduced into 25 rats (FIGS. 8a-d), of which 17 were further subjected to scaffold implantation using the PEG-fibrinogen or PEG-PEG hydrogels (see Table 3, hereinbelow, for representative rats). Four to seven weeks following subjecting rats to critical size tibia defects the rats were sacrificed and the tibias were evaluated for the presence, extent and location of tissue ingrowth and new bone formation. As is shown in FIGS. 9a-b, five weeks following surgery a new bone can be seen in the Gelrin™-implanted rat tibia (FIG. 9b) but not in control rats (FIG. 9a).

TABLE 3

Scaffold implantation in critical size rat tibia defect

| Rat # | Surgery Date | Leg | Hydrogel Composition | Days post-operation |
|---|---|---|---|---|
| 5 | 24/5/04 | Left | PEG-fibrinogen (cleaved, 4-kDa) 15% W/V total; 10% PEG-Fibrinogen and 5% PEG-DA | 42 |
| 6 | 24/5/04 | Right | PEG-fibrinogen (cleaved, 4-kDa) 15% W/V total; 10% PEG-Fibrinogen and 5% PEG-DA | 35 |
| 7 | 16/8/04 | Right | PEG-fibrinogen (whole, 10-kDa) 1.75% PEG-fibrinogen (Gelrin ™) and 3% PEG-DA | 49 |
| 8 | 16/8/04 | Right | PEG-fibrinogen (whole, 10-kDa) 1.75% PEG-fibrinogen (Gelrin ™) and 3% PEG-DA | |
| 9 | 16/8/04 | Right | PEG-fibrinogen (whole, 10-kDa) 1.75% PEG-fibrinogen (Gelrin ™) and 3% PEG-DA | 35 |
| 11 | 27/7/04 | Right | PEG-only (4-kDa) 10% W/V | 41 |
| 12 | 27/7/04 | Right | PEG-only (4-kDa) 10% W/V | 41 |
| 13 | 27/7/04 | Right | PEG-only (6-kDa) 15% W/V | 41 |
| 14 | 27/7/04 | Right | PEG-only (6-kDa) 15% W/V | 41 |
| 15 | 27/7/04 | Right | Empty - control | 41 |
| 16 | 27/7/04 | Right | Empty - control | 41 |
| 21 | 13/7/04 | Right | PEG-fibrinogen (whole, 10-kDa) 1.75% PEG-fibrinogen (Gelrin ™) and 3% PEG-DA | |
| 22 | 13/7/04 | Right | PEG-fibrinogen (whole, 10-kDa) 1.75% PEG-fibrinogen (Gelrin ™) and 3% PEG-DA | |
| 23 | 27/9/04 | Right | PEG-fibrinogen (whole, 10-kDa) 1.75% PEG-fibrinogen (Gelrin ™) and 3% PEG-DA | |
| 24 | 27/9/04 | Right | PEG-fibrinogen (whole, 10-kDa) 1.75% PEG-fibrinogen (Gelrin ™) and 3% PEG-DA | |

Table 3: Representative in vivo experiments performed following the introduction of critical size rat tibia defect. Rats were implanted with either PEG-PEG (PEG-only) or PEG-fibrinogen hydrogels. The PEG-fibrinogen hydrogels were prepared from PEG-fibrinogen precursors and PEG-DA cross-linkers. The PEG-fibrinogen precursors were prepared from either whole fibrinogen Gelrin ™) or from CNBr-cleaved fibrinogen.

FIGS. 10-17 demonstrate the presence of normal bone and cartilage tissue five weeks following introduction of a critical size tibia defect and Gelrin™-implantation. Thus, tibias of Gelrin™-treated rats exhibited well-vascularized, orientated and densely textured fibrous tissue (FIG. 13), osteonal healing (FIG. 11), and Haversian systems with small central canals containing blood vessels (FIG. 10).

Example 4

Biodegradability of PEG-Fibrinogen Hydrogels is Controllable Via the Synthetic PEG Constituent Biodegradability of PEG-Fibrinogen Hydrogels is Reduced by the Addition of Free PEG-DA to the Hydrogels To further characterize the effect of the concentration of the cross-linking molecule of the present invention [i.e., PEG-DA (free PEG)] on the hydrogel biodegradability, $1\times10^6$ smooth muscle cells per ml were seeded inside Gelrin™ hydrogels (1.75% PEG-fibrinogen, 10-kDa PEG) containing various concentrations of PEG-DA. The seeded hydrogels were cultured for 48 hours, following which the ability of the cells to attach and spread inside the hydrogels was evaluated using an inverted microscope. As is shown in FIGS. 18*a-e*, while cells cultured in the pure Gelrin™ matrix (in the absence of free PEG-DA) exhibited cell extensions and significant spreading, cells cultured in hydrogels fabricated with increasing concentrations of free PEG (i.e., 0.5-2%) were devoid of cell extensions and were more rounded. These results demonstrate that excess of a cross-linking molecule (PEG-DA) in the Gelrin™ matrix reduces the cell-mediated degradability and cell-penetration through the hydrogel.

Biodegradability and Cell Extension is Decreased in Gelrin™ Hydrogels Consisting of More Than 1% of a Cross-Linking Molecule (PEG-DA)

To further test the effect of the cross-linking molecule (i.e., functionalized PEG-DA) on cell spreading through the PEG-fibrinogen scaffold of the present invention, Gelrin™ matrices (1.75% PEG-fibrinogen, 10-kDa PEG) were prepared as pure hydrogels (in the absence of free PEG-DA cross-linker) or in the presence of 1 or 2% of free PEG-DA and cell clusters composed of highly compacted smooth muscle cells inside a collagen gel matrix ($5\times10^6$ cells in one mg collagen cluster). The clusters were seeded in the center of each hydrogel by placing the cell mass into the Gelrin™ matrix prior to polymerization and forming the scaffold around the tissue so that it encapsulates the tissue mass from all sides. The degree of cell extension was monitored following 1, 2, 4, and 7 days in culture using phase microscopy. As is shown in FIGS. 19*a-l*, significant cell extensions were observed in pure Gelrin™ hydrogels beginning following one day in culture. In contrast, cell extensions were relatively decreased in smooth muscle cell clusters cultured inside Gelrin™ hydrogels which were fabricated in the presence of 2% free PEG-DA.

Altogether, these results demonstrate that the biodegradability and cell spreading through the scaffolds depends on the degree of the hydrogel cross-linking; higher concentrations of a cross-linking molecule (PEG-DA) inversely correlates with biodegradability of the scaffold hydrogel of the present invention.

Example 5

In Vivo Osteogenesis Mediated by PEGylated Fibrinogen Degradation Products

The osteoinductive properties of denatured PEGylated fibrinogen degradation products in osseous regeneration were studied in a site-specific bone defect. In order to identify the optimal composition of PEG and fibrinogen required for synchronized hydrogel degradation during the defect healing response in the osseous environment, PEGylated fibrinogen hydrogels were prepared with three compositions of synthetic PEG constituent, each providing the material with slightly different susceptibility to proteolytic degradation.

Materials and Experimental Methods

Introduction of a Critical Size Tibia Defect

Tibia defects were introduced into 24 female Sprague-Dawley rats as described in Example 3, except that a 7 mm gap and not a 10 mm gap was excised from the tibia.

Implant Fabrication

Acellular cylindrical plugs were cast in 3-mm diameter silicon tubes using 88 μl aliquots of PEG-fibrinogen precursor by a radical chain polymerization reaction of acrylate end groups. Additional PEG-DA (3% or 5% w/v) was added to the precursor solution in order to increase the number of cross-links and to reduce the susceptibility of the protein backbone to proteolytic degradation. The final ratio of PEG to fibrinogen monomer was roughly 25:1, 100:1, and 150:1 for the 0% PEG-DA, 3% PEG-DA, and 5% PEG-DA, respectively. The precursor solution was mixed with 0.1% (v/v) photoinitiator stock solution made of 10% w/v Irgacure™2959 (generously donated by Ciba Specialty Chemicals, Tarrytown, N.Y.) in 70% ethanol and deionized water. The solution was placed under a UV light (365 nm, 4-5 mW/cm$^2$) for 5 minutes to polymerize. The pre-cast hydrogels were stored in 50 mM PBS containing 2% penicillin-streptomycin (Biological Industries, Israel) for 5 hrs prior to implantation.

Implantation of PEG-Fibrinogen Plugs

PEG-fibrinogen plugs (3-mm diameter and 7-mm long) were inserted into the defect sites as described in Example 3 hereinabove and radiographed shortly after the surgery and thereafter evaluated at weekly intervals by x-ray screening. Altogether, 6 rats were not treated i.e. boney gaps were left empty, 6 rats were treated with PEG fibrinogen plugs comprising no additional PEG-DA (treatment 1), 6 rats were treated with PEG fibrinogen plugs comprising 3% additional PEG-DA (treatment 2) and 6 rats were treated with PEG fibrinogen plugs comprising 5% additional PEG-DA (treatment 3). A summary of the characteristics of the three treatment types is provided in Table 4 hereinbelow.

TABLE 4

Summary of Treatment Cohorts

| Group | Degradation | Composition PEG:Fibrinogen ratio | Degradation Rate in Trypsin (% Wt Loss/min$^{1/2}$) | Degradation Rate in Collagenase (% Wt Loss/min$^{1/2}$) |
|---|---|---|---|---|
| Control | N/A | Empty gap | N/A | N/A |
| 1 | Fast | 25:1 | 8.043 | 9.730 |
| 2 | Intermediate | 75:1 | 1.186 | 2.045 |
| 3 | Slow | 150:1 | 0.872 | 1.007 |

Histological Analysis:

Following a final radiographic evaluation, the right tibia of each rat was carefully excised in its entirety. The samples were fixed in buffered, neutral 10% formalin solution for 10 days and then decalcified in 10% formic acid for 10 days. The specimens were trimmed so as to include the implant site and the adjacent bone tissue on either side of the defect. Following rinsing in PBS, the specimens were dehydrated in increasing concentrations of ethanol in deionized water (70% to 100%). They were embedded in extra-large paraffin blocks. The latter were sectioned at 6 μm, fixed on poly-1-lysine coated glass slides, and stained with hematoxylin and eosin (H&E).

Experimental Results

Osteogenesis

Newly formed bone in the site-specific defects of the tibiae was radiographically observed as early as three weeks post-operatively. When compared to control rats, large amounts of new bone were apparent in the defects of the treatment-2 animals (3% additional PEG-DA) by 5 weeks (FIG. 20). This contrasted with the lack of radiographically detectable bone in the defects of the treatment-1 (0% additional PEG-DA), treatment-3 (5% additional PEG-DA), and control rats. The histological examination confirmed that the rats treated with the intermediate-degrading hydrogel (treatment-2) exhibited the most extensive and widespread osteoneogenesis in and nearby the defect site. The longitudinally, H&E-stained sections of the tibiae revealed that the extent of regenerated bone in the site-specific defects ranged from partial to total bridging of the gap (FIGS. 21a-c). Osteoneogenesis was observed at both the endosteal and subperiosteal aspects. When observed under polarized light, the birefringent pattern of the preexisting lamellar-fibered cortical bone sharply contrasted to that of the woven-fibered boney trabeculae, characteristic of newly deposited osseous tissue. The newly formed subperiosteal bone at the osteotomy sites was contiguous with the boney trabeculae, which were for the most part rimmed by cuboidal osteoblasts on their inner front. The endosteally formed bone was as well continuous with newly formed trabeculae, which extended into the defect site. Randomly scattered adipocytic islands were present in between the trabeculae of the newly formed woven-fibered bone. In but a few samples, the medullary cavity contained some fibrous tissue proximal to the osteotomy site.

In those cases in which there was total osseous bridging of the site-specific defect, the implant had been entirely resorbed and replaced by lamellar-fibered bone with an atypical pattern of Haversian, i.e., osteonal bone. The newly formed bone was uninterrupted from one end to the opposite end of the osteotomies (FIG. 21c), consisting of birefringent, lamellar-fibered, compacta-type bone with a moderate number of vessels within the Haversian system (data not shown), characteristic of mature bone. In those instances in which there was but a partial bridging of the defect, there was often endochondral ossification of cartilaginous islets. To exemplify, FIG. 22a illustrates a typical endochondral cap at the medial aspect of the regeneration front: Hypertrophic chondrocytes were focally present in the cartilaginous cap, which was enclosed by a thin, perichondrium-like fibrous tissue with parallel-oriented mature fibrocytes at its leading edge (FIG. 22b).

Hydrogel Degradation and Osteogenesis

The extent as well as the distribution of the osteoneogenesis depended on the erosion pattern of the hydrogel material and its relative placement in the defect site after the 5-week follow-up. Most notably, in treatment-2 rats, the regenerated bone extended well into the defect site, which included residual hydrogel surrounded by either a fibrous capsule or a foreign body-type granulation tissue (FIGS. 21a-c). Also, fibro-fatty tissue primarily composed of fat cells with a minor fibrous component or fibrous tissue with a minor mononuclear celled inflammatory infiltrate occurred in between the degraded hydrogel and the front of the newly formed bone (FIG. 22a). In contrast to the treatment-2 rats, the characteristic features of the fast-degrading hydrogels in the implant site (treatment-1) resembled a typical nonunion with loosely organized and edematous fibrous tissue with a minor non-specific chronic inflammatory infiltrate (FIGS. 5a-c). The well vascularized connective tissue within the gap was typical of that described in the literature as being consistent with nonunions, the distinctive picture which we encountered in all the control rats. Animals which did not show any signs of new bone formation in the site of the defect exhibited longitudinally oriented myofibers which, so it seems, passively fell into the defect, particularly at its center. There was subperiosteal new bone formation at the end of the long bone segment in some cases. The defect site was filled with the hydrogel surrounded by a fibrous capsule and a subperiosteally regenerated bone at the osteotomy locales in those rats treated with the slow degrading hydrogels (treatment-3).

Implant Histocompatibility:

The PEG-fibrinogen hydrogels were also evaluated for histo(in)compatibility within the site of the tibial defect. Microscopically, hydrogels which were partially degraded but remained in the defect after 5 weeks (treatment-2) revealed a serpentine foreign body type granulation tissue nearby residues of the PEG-fibrinogen hydrogels (FIG. 24a). This granulation consisted of lymphocytes admixed with macrophages. At the tissue-implant interface the hydrogel was undergoing erosion by the finger-like projections of the granulation tissue that degraded the material and cleared it from the surface via the phagocytic pathway (FIG. 24b). Encircling the serpentine projections of the above mentioned granulation tissue was a chronic, non-specific inflammatory infiltrate consisting mainly of lymphocytes with a minor component of macrophages. The hydrogel itself appeared diffusely homogeneous and was lightly colored in the H&E-stained sections; it was noteworthy that there was no cellular infiltrate apart from that at the eroding front of the granulation tissue (FIG. 24a, solid arrows). The response was restricted to just a chronic, non-specific inflammatory reaction in certain regions of the tissue-material interface whereas elsewhere there had evolved a pallisading foreign body type granulation tissue (FIG. 24a, dashed arrows). The infiltration was focally admixed with a major infiltrate of neutrophiles, while at the same time those implants which had not been degraded after 5 weeks (treatment-3) were generally enclosed within a fibrous capsule composed of several layer of elongated parallel oriented fibrocytes (FIG. 23b). It thus stood to reason that the aforementioned granulomatous response to the implanted hydrogel was indicative of the histoincompatibility of the fibrin-based materials as described in detail [Boss J H. Biocompatibility: Review of the concept and its relevance to clinical practice. In: Wise D L, editor. Biomaterials and Bioengineering Handbook. New York, Basel: Marcel Dekker, Inc.; 2000. p. 1-94] in as much as there was a foreign body type response nearby the implant.

Analysis and Discussion

This study shows that the resilience of the PEG-fibrinogen matrix can be synchronized with the optimal healing characteristics of a site-specific bone defect. Hydrogels having three distinctive compositions designed for slow, intermediate, and fast degradation rates were fabricated and characterized (Table 4). The hydrogels were implanted into site-specific defects of the tibiae of rats; the rationale being that the ingrowth matrix would displace the post traumatic fibrin clot while sustaining a similar healing effect in the site of the defect for a longer duration. There is undisputable evidence of extensive osteoneogenesis within the site of the osseous defect based on recorded radiographic and histological findings at the 5-weeks postoperative interval (FIGS. 21a-c). Moreover, the extent of newly formed bone within the gap is well correlated to the degradation of the hydrogel matrix. Nevertheless, the precise process by which osteoneogenesis occurs with an eroding PEG-fibrinogen hydrogel in the defect remains unclear.

In many histopathology sections of the treatment-2 rats residues of the hydrogel were detected apparently giving way to regenerating bone penetrating the boney defect from both the proximal or distal aspects of the osteotomies. It may be concluded, therefore, that the hydrogel undergoing erosion clears the way for the regenerating bone (FIG. 22a). The hydrogel in some cases has been completely degraded such that the whole osseous defect has been filled with newly deposited bone from one side of the osteotomy to the other side (FIG. 21c). In contrast to the treatment-2 rats, remnants of fast degrading hydrogels (treatment-1) have neither been observed within the site of the defect nor has osteoneogenesis occurred within the site-specific defect of these rats (FIG. 23a). It is, therefore, likely that these hydrogels underwent rapid proteolysis in the site of the osseous defects and were not present at the 5 week postoperative interval. Consequently, all the treatment-1 animals exhibited extensive fibrotic scaring in the gap (FIG. 23a). It may be speculated in this context that treatment-1 rats behave in a similar fashion to the non-treated control rats in that the fibrin-like clot disappears from the gap early on in the healing process and does not provide the necessary protection from the invading fibrocytes as is characteristic in cases of nonunions. Conversely, the slow-degrading hydrogels (treatment-3) remain intact in the defect site following 5 weeks and exhibit only a local osteoneogenesis nearby the implant (FIG. 23b).

In the course of these experiments it has become apparent that only the intermediate degrading PEG-fibrinogen hydrogel treatment (treatment-2) causes extensive new bone formation at the site of the boney defect. Nevertheless, judging from just the histological findings it is unclear whether the PEGylated fibrinogen material is endowed with osteoinductive properties or whether the so-called synchronized degradation and healing response are responsible for the widespread osteoneogenesis. There are at least a couple of plausible hypotheses that could explain the observed outcomes in the above described experimental setup. Firstly, it is possible that the macrophages that erode the fibrin-based biosynthetic matrix slowly release osteoinductive fragments of the fibrinogen to act as an eroding front for osteoneogenesis to occur in as much as the gels slowly give way for the newly generating bone. Secondly, subperiosteal new bone is deposited by the osteoblasts concurrently with the removal of the hydrogel by the foreign body induced granulation tissue. In the case of the second option, the PEG-fibrinogen does not necessarily need to possess osteoinductive properties to facilitate the observed healing response within the site-specific defect. Both explanations are consistent with the observations that faster degrading hydrogels do not provide synchronized erosion with the natural healing rate in a rat site-specific bone defect, which typically requires 4 to 5 weeks to heal completely.

The current inventors propose that the fragments released from the PEG-fibrinogen hydrogel probably facilitate a prolonged osteogenic response within the site-specific defect, thereby explaining the unusual extent of the oestegenic response in the treatment-2 rats. There is ample evidence that fibrinogen and fibrin degradation products are potent agonist of wound healing [Thompson W D, et al., J Pathol 1991; 165 (4): 311-8; Rybarczyk B J, et al., Blood 2003; 102(12):4035-43], especially as concerns endothelial cells [Lorenzet R, et al., Thromb Haemost 1992; 68(3):357-63; Bootle-Wilbraham C A, et al. Angiogenesis 2001; 4(4):269-75] and fibroblasts [Gray A J, et al; Am J Respir Cell Mol Biol 1995; 12(6):684-90; Gray A J, et al., J Cell Sci 1993; 104 (Pt 2):409-13]. In fact, fibrin has been evidenced to induce an osteogenic response in bone defects filed with osteoconductive materials [Abiraman S, et al., Biomaterials 2002; 23(14): 3023-31; Kania R E, et al., J Biomed Mater Res 1998; 43(1):

38-45; Gray A J, et al., J Cell Sci 1993; 104 (Pt 2):409-13]. Moreover, if fibrinogen fragments do not possess osteoinductive qualities, a similar outcome to that demonstrated by other researchers who utilize the inert biomimetic ingrowth matrices without added growth factors would be expected. Pratt et al. have reported that eroding fibrin-mimetic hydrogels are unable to support new bone formation when occupying a size-specific calvarial defect in the absence of the osteoinductive BMP-2 [Pratt A B, Biotechnol Bioeng 2004; 86(1):27-36]. Likewise, Lutolf et al. have demonstrated similar results employing a collagen-mimetic biosynthetic ingrowth matrix without osteoinductive BMP-2 [Lutolf M P, et al. Nat Biotechnol 2003; 21(5):513-8]. In comparison, the extent of osteoneogenesis using PEG-fibrinogen hydrogels without added osteoinductive growth factors can only be explained by an osteoinductive role of the fibrinogen constituent in as much as it is unlikely that the PEG constituent has osteoinductive qualities. In support of the proposal that protein-based hydrogels illicit an osteoinductive response in the model of a site-specific bone defect, Ikada and co-workers have demonstrated osteoneogenesis in a calvarial defect filled with a gelatin ingrowth matrix in the absence of osteoinductive growth factors, though only when the hydrogels are of a high water content [Hong L, et al. J Neurosurg 2000; 92(2): 315-25; Yamamoto M, et al. J Control Release 2000; 64(1-3):133-42].

There is some discrepancy between the mostly mild osteogenic potential of FSs as reported in the relevant literature and the extensive osteoneogenesis discerned in the current study. The observed osteoneogenesis may be attributable to the released fragments of PEGylated fibrinogen and not necessarily to the intact matrix. A sustained presentation of mildly osteogenic fibrinogen fragments could account for the prolonged osteogenic response over the 5 weeks of the healing period. It is noted in support of this explanation that most of the osteoneogenesis in the treatment-2 defects occurs at least several hundred microns from the eroding surface of the hydrogels (FIG. 24a), the latter being consistently surrounded by an inflammatory infiltrate. Even the slow degrading hydrogels (treatment-3) induce some mild osteogenic response around the implant, presumably because of the released fragments of PEGylated fibrinogen. There is no evidence of osteoneogenesis in the fast degrading hydrogel-treated animals (treatment-1), suggesting that rapid dissolution of the fibrinogen fragments does not enable adequate new bone formation.

Others authors have also commented on the importance of sustained release of osteoinductive factors in mediating osteogenesis in bony defects. Most notably, Yamamoto et al. reported on the synchronized release of immobilized basic fibroblast growth factor (bFGF) from biodegradable gelatin hydrogels in a rabbit calvarial defect model [Yamamoto M, et al. J Control Release 2000; 64(1-3):133-42]. Hong et al. utilized a similar concept with transforming growth factor beta-1(TGF-beta1) [Hong L, et al. J Neurosurg 2000; 92(2): 315-25]. In both these studies, the results indicated that the sustained release of either bFGF or TGF-beta1 from the hydrogel with synchronized degradability is necessary to fully capitalize on the osteoinductive properties of one of the other of these factors. The factor retention in the site of the defect is too limited to induce osteoneogenesis when hydrogels that degrade too rapidly are employed. On the other hand, the matrix serves as a physical barrier for factor-induced bone regeneration in the calvarial defect when hydrogels that degrade to slowly are used.

In conclusion, it may be submitted that the efficacy of the osteogenic response described in this study evolves in the wake of the combination of the synchronized degradation of the hydrogel and the sustained release of fragment of osteoinductive fibrinogen. The PEGylated fibrinogen matrix may, therefore, constitute a highly efficacious tool for orthopaedic surgeons who are faced with the problematic task of promoting the healing of site-specific defects in patients with bone fractures complicated by obstinate nonunions.

Example 6

Controlling Three-Dimensional Neurite Outgrowth Using PEG-Fibrinogen Hydrogels

To test the potential of the PEG-fibrinogen scaffold material to facilitate nerve regeneration, a chicken embryo dorsal root ganglion (DRG) outgrowth model was used. In the initial stage of nerve regeneration fibrin provides Schwann cells environmental cues for proliferation, thus ensuring that there are enough cells to associate with the regenerating neurons. In the absence of fibrin, Schwann cells can then differentiate and re-myelinate the newly formed axons. Accordingly, this model implies that the untimely persistence of fibrin in the injury site can interfere with the delicate timing of the nerve regeneration process and disrupt the construction of functional nerve tissue. Therefore the ability to control the degradation and removal of the fibrin matrix is crucial for enabling successful nerve regeneration.

The synthetic PEG component provides the desired physical properties and controllable degradation characteristics. The natural fibrinogen component of the biosynthetic matrix supplies cues that regulate Schwann cell proliferation and migration and therefore will likely influence re-myelination of the regenerated axons. An additional advantage of the PEGylated fibrinogen approach is that it enables the control of the relative bioactivity of the fibrinogen degradation products based on the rationale that covalently bound PEG can decrease the accessibility to active sites on both intact and degraded fibrinogen molecule. Hence, a PEGylation strategy offers control over fibrinogen degradation, bioactivity, and molecular architecture of the nerve guidance conduit (NGC) cell ingrowth matrix.

In addition, the present invenntors have shown that it is possible to control the biodegradation of the fibrinogen matrix by changing relative amounts of fibrinogen and PEG in such a system. To this end, Dikovsky et al. showed that increased PEG-DA concentrations in the PEGylated fibrinogen hydrogel decreased proteolytic susceptibility of the protein backbone and thus delayed the PEGylated fibrinogen biodegradation [Dikovsky D. et al. Biomaterials 2006; 27(8): 1496-506]. The PEGylated fibrinogen system also presents additional advantages for nerve regeneration in that therapeutic growth factors can easily be encapsulated and enmeshed in the dense polymeric network of the hydrogel during the polymerization process. The encapsulation of factors for nerve regeneration could provide neuron-specific signals beyond the inherent biological and structural provisions of the PEGylated fibrinogen hydrogel network. One of the most vital neurotrophins in neuronal development and regeneration is nerve growth factor (NGF). Schwann cells produce NGF, a 26 kDa dimmer, in their immature phase during early development and after post-injury dedifferentiation in mature nerves. Accordingly, it is important that NGF be an integral part of the nerve guidance implant material.

Materials and Experimental Methods

Dorsal Root Ganglia Experiments:

DRGs were dissected from E9-E11 chicken embryos and collected in PBS with 1% penicillin-streptomycin (Biological industries, Kibbutz Beit Haemek, Israel). Fibroblast contamination of the DRGs was minimized by pre-plating the DRGs for one hour in MEM with Glutamax I medium (Gibco, Grand Island, N.Y., USA) containing 1% penicillin-streptomycin and 10% fetal calf serum (FCS) (Biological industries, Kibbutz Beit Haemek, Israel). The pre-plated DRGs were then physically removed from the culture dish and entrapped in hydrogel constructs prepared from a precursor solution of PEGylated fibrinogen (prepared as described in Example 1) and photoinitiator. Briefly, the precursor solution was mixed with 1% (v/v) photoinitiator stock solution made of 10% (w/v) Irgacure™2959 (Ciba Specialty Chemicals, Tarrytown, N.Y.) in 70% ethanol and deionized water. The solution was then centrifuged at 14,000 RPM for 1 minute before being used to entrap the isolated DRGs. The entrapment procedure involved gently placing the intact DRGs into a 48-well plate containing the precursor solution. The 48-well plate was first pre-coated with 100 µl polymerized PEGylated fibrinogen in order to prevent cell growth on the bottom of the well. Each DRG was placed into 200 ml PEGylated fibrinogen solution and polymerized under a UV light (365 nm, 4-5 mW/cm$^2$) for 5 minutes. After hydrogel polymerization, the entrapped DRGs were visually inspected to ensure 3-D encapsulation in the biosynthetic matrix (FIGS. 25a-c). Culture medium was immediately added to the polymerized hydrogels (500 µl in each well) and changed every two days. The culture medium was comprised of MEM with Glutamax I medium containing 1% penicillin-streptomycin and 10% FCS. Unless otherwise indicated, the medium was supplemented with 50 ng/ml 2.5S mouse nerve growth factor (mNGF) (Alomone labs LTD., Jerusalem, Israel).

Quantitative Outgrowth Measurements:

Cellular outgrowth from the DRG into the transparent PEGylated fibrinogen hydrogel was recorded during the four-day duration of the experiment. Each DRG construct was documented with digital images taken daily using a Nikon TE2000 phase contrast microscope with a 4× objective and a digital CCD camera (Jenoptik, Germany). Quantitative neurite outgrowth measurements were obtained directly from the digital phase contrast micrographs using ImageJ software. Neurites, which can be identified by their characteristic sprouting morphology, were measured from the base (outer margin of the DRG) along their length and up to the tip. Up to a total of 80 measurements were made for each DRG construct, according to the ability to trace continuous neurites. The mean DRG neurite outgrowth was then calculated for each individual DRG construct by averaging the 80 measurements of each construct (n=1). The average neurite outgrowth for each treatment was calculated using the mean DRG neurite outgrowth data.

Histology and Immunofluorescence:

Preparation of the DRG specimens for histological and immunofluorescence evaluation involved fixation in 4% paraformaldehyde (Gadot, Haifa, Israel) for 20-30 min, PBS rinses, and overnight cryoprotection in a 30% sucrose solution (in PBS) at 4° C. Each fixed construct was then slow-frozen in Tissue-Tek® O.C.T Compound (Sakura Finetek, Torrance, Calif., USA) using liquid nitrogen cooled isopropanol (Gadot, Haifa, Israel). Frozen constructs were stored in a deep freezer (−80° C.) for up to three months. The specimens were sectioned orthogonally into 30-µm thick slices using a cryostat and mounted on Polysin™ slides (Menzel-Glaser, Braunschweig, Germany). Prior to staining, the slides were air dried at RT for 2 hours and stored at −20° C. Hematoxylin and Eosin (H&E) staining (Sigma, St. Louis, Mo., USA) was performed according to standard manufacturer's protocols.

Immunofluoerscence labeling of the 30-µm thick specimens involved treatment with 0.3% Triton® X-100 (Bio Lab LTD., Jerusalem, Israel) for 5 min at RT and incubation in blocking solution containing PBS and 1% glycine, 10% horse donor serum (HDS) (Biological industries, Kibbutz Beit Haemek, Israel) and 0.1% Triton® X-100 for 30 min at RT. The sections were double stained with primary antibodies against βIII-tubulin, (G712A, Promega, Madison, Wis., USA) and s100 (S2644, Sigma, St. Louis, Mo., USA). The primary antibodies were diluted in blocking solution (1:1000 dilution for βIII-tubulin and 1:200 dilution for s100) and incubated overnight at 4° C. in a humidity chamber. The sections were rinsed and incubated for 30 minutes at RT with fluorescently conjugated secondary antibodies, including 1:250 diluted goat anti-mouse Cy3 (Chemicon International, Temecula, Calif., USA) for βIII-tubulin and 1:300 diluted goat anti-rabbit FITC (Jackson Immunoresearch Laboratories INC., west Grove, Pa., USA) for s100. A nuclear counter-stain was incorporated directly into the secondary antibody staining solution using a 1:500 diluted DAPI stock solution (Sigma Aldrich, St. Louis, Mo., USA). Following incubation, sections were rinsed with PBS and mounted with FluoromountG (Southern Biotechnology Associates, INC., Birmingham, Ala., USA).

Statistical Analysis:

Statistical analysis was preformed on data sets from at least two independent experiments. Depending on the data set, treatments were compared by single-factor ANOVA, two-factor ANOVA, or paired student t-test. Statistical significance was accepted for p<0.01.

Experimental Results

DRG Outgrowth:

Tissue constructs were prepared by entrapping DRGs inside PEGylated fibrinogen hydrogels (FIGS. 25a-c) and cultivating them for up to one month in a $CO_2$ incubator. Cellular outgrowth from the DRG was visible in phase contrast micrographs and histological H&E sections (FIGS. 26a-d). Throughout the experiment, cells from the DRG invaded the PEGylated fibrinogen hydrogel and eventually occupied the entire gel (not shown). Phase contrast micrographs show the distinct spatial organization and orientation of the invading DRG cells into the PEGylated fibrinogen matrix after two days (FIG. 26a). A high magnification of this organization is shown in FIG. 26b, where long thin processes (neurites) extending out of the DRG are accompanied by non-neuronal cells (dark circular spots) that emerge from the DRG core and align along the neurite extensions. The non-neuronal outgrowth from DRGs (FIG. 26b, arrowhead) was shown to lag after neurite extensions (FIG. 26b, arrow). Histological cross-sections (30 µm) of the DRG constructs following four days of culture stained with H&E showed similar cellular invasion characteristics (FIGS. 26c-d).

The arrangement of non-neuronal (glial) cells invading from the DRG and aligning with the neurites resembled the in vivo spatial organization of neurons and their associated Schwann cells. In order to identify the different invading DRG cells in these experiments, neurites and Schwann cells were both labeled with neuronal and glial immunofluorescent markers. Immuno-detection in 30 µm thick cross-sections of the DRG constructs was preformed with the neuronal marker βIII-tubulin antibody and the Schwann cell marker s100 antibody. The labeling clearly shows extending neurites originating from the DRG into the matrix, and associated Schwann cells in close proximity to the invading neuronal cells (FIGS. 27a-c). Higher magnification images show the Schwann cells closely associated with the neurites to the extent that they align along with and adjacent to the βIII-tubulin positive extensions (FIGS. 27d-f). These results were well correlated to observations of the DRG cells inside the hydrogel as observed by phase contrast microscopy (FIGS. 26a-b).

Nerve Growth Factor Treatments:

Experiments to examine the influence of NGF in the culture medium versus encapsulated in the hydrogel during its formation were performed with DRG outgrowth constructs. Three treatment conditions were compared: a treatment using no NGF (NO-NGF), a treatment using free-soluble NGF in the culture medium (FS-NGF), and a treatment with enmeshed NGF in the hydrogel network (EN-NGF). Two independent experiments in each treatment condition were preformed for a total of six repeats using two different batches of PEGylated fibrinogen precursors. The constructs were cultured for four days and imaged daily to measure the progress of 3-D cell outgrowth from the DRGs into the hydrogel network. Based on results from the phase contrast micrographs (data not shown), the free-soluble and enmeshed NGF (FS-NGF and EN-NGF) facilitated outgrowth of both non-neuronal cells and neurites into the hydrogel as compared to NGF-deprived constructs (NO-NGF). In the absence of NGF, there was no observable outgrowth of neurites and only partial outgrowth of non-neuronal cells, which were most likely Schwann cells or fibroblasts. Immunohistochemistry confirms the observations of phase contrast microscopy in that βIII-tubulin and s100 positive cells were present in NGF treatments (FS-NGF and EN-NGF) but only s100 positive cells were seen in the NGF-deprived treatment (NO-NGF) (FIGS. 28a-c). Based on these qualitative data, it is difficult to conclude if there are significant differences in 3-D DRG outgrowth between the free soluble and enmeshed NGF; both free soluble NGF (FS-NGF) and enmeshed NGF (EN-NGF) treatments showed a similar labeling pattern.

In order to further differentiate between the free soluble and enmeshed NGF treatments, quantitative outgrowth experiments were performed. Using digital image processing, the distance of neurite outgrowth was measured in DRG constructs that were cultured with free soluble NGF (FS-NGF) or enmeshed NGF (EN-NGF). FIG. 28d shows that there was little difference between the two treatment conditions at any time during the culture period ($p > 0.35$, $n=6$). In both free soluble and enmeshed NGF, there was a rapid increase in neurite outgrowth over the course of the four-day experiment ($P < 0.01$, $n=6$), with a mean neurite length reaching 719.9 µm and 701.2 µm for FS-NGF and EN-NGF treatments, respectively after four days.

Cellular Outgrowth and Hydrogel Biodegradation:

Alterations to the biodegradation properties of the fibrinogen backbone of the hydrogel matrix can also influence the DRG cellular outgrowth characteristics, particularly as related to the relative invasion of Schwann cells and neurites. Experiments were performed to assess the ability to regulate the outgrowth kinetics using different compositions of the matrix (relative amount of PEG and fibrinogen) based on the rationale that the proteolytic resistance of the fibrinogen matrix will increase with increasing concentrations of PEG. Consequently, the PEGylated fibrinogen hydrogels also become more cross-linked with additional PEG, thereby changing the mesh size, hydration and mechanical properties of the matrix. Four different compositions of PEG to fibrinogen were tested, including: 30:1, 60:1, 120:1, and 180:1 (PEG:fibrinogen). It is important to note that the composition of the constructs in each treatment level was such that the pure PEGylated fibrinogen solution (30:1 treatment) was modified with additional unreacted PEG-DA before the UV polymerization step. Two independent experiments in each treatment level were preformed for a total of nine repeats using two different batches of pure PEGylated fibrinogen precursors.

Overall, the extent of cellular outgrowth from the DRG into the matrix was decreased with addition of higher concentrations of PEG-DA in the hydrogel matrix (FIGS. 29a-p). The lag between neurites and glial cells was visibly reduced with the addition of higher concentrations of PEG-DA (FIGS. 29q-t). A summary of the neurite outgrowth kinetics data with the different concentrations of PEG is summarized in FIG. 29u. Statistical analysis of the kinetics data (2-factor ANOVA) revealed that outgrowth steadily increased with culture time ($p < 0.01$, $n=9$) and that higher concentrations of PEG slowed down the cellular invasion ($p < 0.01$, $n=9$). In particular, constructs made with high concentrations of PEG-DA (120:1 and 180:1) delayed neurite outgrowth significantly from day 2 of culture when compared to constructs made with lower concentrations of PEG (30:1 and 60:1). Neurite outgrowth in the 180:1 hydrogels exhibited slowest outgrowth kinetics of all treatment levels, and reached a mean neurite length of 201.6 µm following four days of culture. Constructs made with 120:1 exhibited moderate neurite outgrowth rate and reached a mean neurite length of 490.8 µm following four days. There was no significant difference in neurite outgrowth between the 30:1 and 60:1 treatment levels ($p > 0.50$, $n=9$); in both cases, outgrowth progressed most rapidly and reached a mean neurite length of 807.8 µm and 850.6 µm, respectively following four days of culture.

Fibrinogen and DRG Cellular Outgrowth:

The importance of the fibrinogen backbone in enabling cellular outgrowth from the DRG into the PEGylated fibrinogen matrix was investigated using PEG-only hydrogels as controls. DRG constructs were made of 10% PEG-DA without fibrinogen and compared to constructs made with PEGylated fibrinogen. The constructs were cultured for three days and cellular outgrowth was documented on the third day of culture. FIG. 30a shows that without fibrinogen, very few neurites extend out of the DRG and outgrowth of non-neuronal cells, including Schwann cells, was not observed. In contrast, fibrinogen containing hydrogels exhibit massive DRG outgrowth, including neurite and Schwann cell invasion, following three days of culture (FIG. 30b). These results demonstrate fibrinogen's role in permitting DRG outgrowth that includes proteolytic susceptibility, inductive and conductive environmental cues which may be crucial for functional peripheral nerve regeneration. Consequently, neuronal outgrowth was practically eliminated even in the PEGylated fibrinogen hydrogels when DRG cultures were deprived of NGF (NO-NGF), whereas other cell types (including Schwann cells) are observed invading the hydrogel (FIG. 30c).

Analysis and Discussion

Peripheral nerve regeneration is a complex, highly regulated process which requires specific environmental cues that are provided by the extracellular matrix (ECM) and the tight bi-directional communication between regenerating axons and their associated Schwann cells. Many peripheral nerve regeneration strategies using NGCs have been designed to provide the optimal milieu for PNS regeneration, using natural or synthetic materials and different growth factor delivery strategies. Because NGCs have yet to achieve the efficacy of the nerve autografts, alternative approaches are sought that can leverage the natural healing mechanisms of peripheral nerve repair following moderate injury. To this end, the PEGylated protein hydrogels of the present invention can serve as a template for nerve regeneration which combines the paracrine effects of fibrin(ogen) and the control over biodegradation and bioactivity afforded by the PEGylation paradigm.

The experiments described hereinabove support a potential NGC biomaterial system based on PEGylated fibrinogen hydrogels that maintain outgrowth of DRG cells. A 3-D hydrogel matrix composed of PEG and fibrinogen was used to encapsulate chicken embryo DRGs to form transparent constructs that enable straightforward monitoring of the DRG outgrowth (FIGS. 25a-c). Outgrowth of neurites and non-neuronal (glial) cells was observed from the DRG into the hydrogel (FIGS. 26a-d). Furthermore, in vivo like spatial organization of these cells was observed. Specifically, the long neurites were observed in close proximity to their associated glial cells. Using antibodies specific for βIII-tubulin and s100, it was shown that the s100-positive Schwann cells are highly associated with the radially extending βIII-tubulin positive neurites (FIG. 27a-f). These neuron-Schwann cell complexes enable the production and organization of myelin along the length of extending axons in order to provide rapid and efficient propagation of action potentials along axons. Consequently, this distinct spatial organization is a prerequisite for axonal myelination during the later phase of neuronal regeneration.

It is likely that DRG neurites and glial cells employ a proteolytic mechanism to invade the PEGylated fibrinogen hydrogel matrix in as much as the hydrogel is highly susceptible to proteases [Almany L, et al. Biomaterials 2005; 26(15):2467-77] and is otherwise too dense to permit cellular invasion in the absence of proteolysis. Because the fibrinogen backbone affords the biosynthetic hydrogel its biodegradability, it also provides a means of releasing cleaved fragments of fibrinogen from the matrix upon degradation. In this manner the kinetics of neurite and glial cell invasion as well as the bioactivity of the released fibrinogen fragments can be controlled by changing the relative amount of PEG and fibrinogen. Higher amounts of PEG reduce the susceptibility to proteolytic degradation of the fibrinogen backbone [Dikovsky D, et al, Biomaterials 2006; 27(8):1496-506] and presumably reduces the overall bioactivity of the degraded fibrinogen fragments that are released to the surrounding tissue [Hooftman G, et al. J Bioact Compat Polym 1996; 11:135-159]. Indeed, the addition of PEG to the biosynthetic hydrogel slows down the invasion of both Schwann cells and neurites from the DRG (FIGS. 29a-p). Furthermore, it appeared that in lower concentrations of PEG, the non-neuronal outgrowth from DRGs lagged behind the neurite extensions, whereas the higher concentrations of PEG minimized this lag (FIGS. 29q-t).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Langer R, Vacanti J P. Tissue engineering. Science 1993; 260(5110):920-6.
2. Nerem R M, Seliktar D. Vascular tissue engineering. Annu Rev Biomed Eng 2001; 3:225-43.
3. Griffith L G. Emerging design principles in biomaterials and scaffolds for tissue engineering. Ann N.Y. Acad Sci 2002; 961:83-95.
4. Drury J L, Mooney D J. Hydrogels for tissue engineering: scaffold design variables and applications. Biomaterials 2003; 24(24):4337-51.
5. Hubbell J A. Materials as morphogenetic guides in tissue engineering. Curr Opin Biotechnol 2003; 14(5):551-8.
6. Leach J B, Bivens K A, Collins C N, Schmidt C E. Development of photocrosslinkable hyaluronic acid-polyethylene glycol-peptide composite hydrogels for soft tissue engineering. J Biomed Mater Res 2004; 70A(1):74-82.
7. Leach J B, Schmidt C E. Characterization of protein release from photocrosslinkable hyaluronic acid-polyethylene glycol hydrogel tissue engineering scaffolds. Biomaterials 2005; 26(2): 125-135.
8. Merrill E A, Salzman E W. Polyethylene oxide as a biomaterial. ASAIO J 1983; 6:60-4.
9. Temenoff J S, Athanasiou K A, LeBaron R G, Mikos A G. Effect of poly(ethylene glycol) molecular weight on tensile and swelling properties of oligo(poly(ethylene glycol) fumarate) hydrogels for cartilage tissue engineering. J Biomed Mater Res 2002; 59(3):429-37.
10. Elbert D L, Hubbell J A. Conjugate addition reactions combined with free-radical cross-linking for the design of materials for tissue engineering. Biomacromolecules 2001; 2(2): 430-41.
11. Elisseeff J, McIntosh W, Anseth K, Riley S, Ragan P, Langer R. Photoencapsulation of chondrocytes in poly (ethylene oxide)-based semi-interpenetrating networks. J Biomed Mater Res 2000; 51(2):164-71.
12. Nguyen K T, West J L. Photopolymerizable hydrogels for tissue engineering applications. Biomaterials 2002; 23(22):4307-14.
13. Lutolf M P, Hubbell J A. Synthesis and Physicochemical Characterization of End-Linked Poly(ethylene glycol)-co-peptide Hydrogels Formed by Michael-Type Addition. Biomacromolecules 2003; 4(3):713-22.
14. Herrick S, Blanc-Brude O, Gray A, Laurent G. Fibrinogen. Int J Biochem Cell Biol 1999; 31(7): 741-6.
15. Werb Z. ECM and cell surface proteolysis: regulating cellular ecology. Cell 1997; 91(4):439-42.
16. Halstenberg S, Panitch A, Rizzi S, Hall H, Hubbell J A. Biologically engineered protein-graft-poly(ethylene glycol) hydrogels: a cell adhesive and plasmin-degradable biosynthetic material for tissue repair. Biomacromolecules 2002; 3(4):710-23.
17. Lutolf M P, Lauer-Fields J L, Schmoekel H G, Metters A T, Weber F E, Fields G B, et al. Synthetic matrix metalloproteinase-sensitive hydrogels for the conduction of tissue regeneration: engineering cell-invasion characteristics. Proc Natl Acad Sci USA 2003; 100(9):5413-8.
18. Gobin A S, West J L. Cell migration through defined, synthetic ECM analogs. Faseb J 2002; 16(7):751-3.

19. Elbert D L, Pratt A B, Lutolf M P, Halstenberg S, Hubbell J A. Protein delivery from materials formed by self-selective conjugate addition reactions. J Control Release 2001; 76(1-2):11-25.
20. Lum L Y, Cher N L, Williams C G, Elisseeff J H. An extracellular matrix extract for tissue-engineered cartilage. IEEE Eng Med Biol Mag 2003; 22(5):71-6.
21. Oakes B W, Batty A C, Handley C J, Sandberg L B. The synthesis of elastin, collagen, and glycosaminoglycans by high density primary cultures of neonatal rat aortic smooth muscle. An ultrastructural and biochemical study. Eur J Cell Biol 1982; 27(1):34-46.
22. Remuzzi A, Dewey C F, Jr., Davies P F, Gimbrone M A, Jr. Orientation of endothelial cells in shear fields in vitro. Biorheology 1984; 21(4):617-30.
23. Seliktar D, Zisch A H, Lutolf M P, Wrana J L, Hubbell J A. MMP-2 sensitive, VEGF-bearing bioactive hydrogels for promotion of vascular healing. J Biomed Mater Res 2004; 68A(4):704-16.
24. Kurfurst M M. Detection and molecular weight determination of polyethylene glycol-modified hirudin by staining after sodium dodecyl sulfate-polyacrylamide gel electrophoresis. Anal Biochem 1992; 200(2):244-8.
25. Pomroy N C, Deber C M. Solubilization of hydrophobic peptides by reversible cysteine PEGylation. Biochem Biophys Res Commun 1998; 245(2):618-21.
26. Midha R, Munro C A, Dalton P D, Tator C H, Shoichet M S. Growth factor enhancement of peripheral nerve regeneration through a novel synthetic hydrogel tube. J Neurosurg 2003; 99(3):555-65.
27. Zisch A H, Lutolf M P, Ehrbar M, Djonov V, Bezuidenhout D, Davies N, et al. Cell-demanded Release of VEGF from Synthetic, Biointeractive Cell-ingrowth Matrices for Vascularized Tissue Growth. FASEB Journal 2003.
28. Lutolf M P, Weber F E, Schmoekel H G, Schense J C, Kohler T, Muller R, et al. Repair of bone defects using synthetic mimetics of collagenous extracellular matrices. Nat Biotechnol 2003; 21(5):513-8.
29. Mann B K, Gobin A S, Tsai A T, Schmedlen R H, West J L. Smooth muscle cell growth in photopolymerized hydrogels with cell adhesive and proteolytically degradable domains: synthetic ECM analogs for tissue engineering. Biomaterials 2001; 22(22):3045-51.
30. Holmes T C. Novel peptide-based biomaterial scaffolds for tissue engineering. Trends Biotechnol 2002; 20(1):16-21.
31. Mann B K, Schmedlen R H, West J L. Tethered-TGF-beta increases extracellular matrix production of vascular smooth muscle cells. Biomaterials 2001; 22(5):439-44.
32. Blom E J, Klein-Nulend J, Klein C P, Kurashina K, van Waas M A, Burger E H. Transforming growth factor-beta1 incorporated during setting in calcium phosphate cement stimulates bone cell differentiation in vitro. J Biomed Mater Res 2000; 50(1):67-74.

---

What is claimed is:

1. A precursor molecule comprising a fibrinogen protein which is denatured and retains an activity of forming a scaffold and at least two polyethylene glycol (PEG) molecules covalently connected to free thiol groups of said denatured fibrinogen protein, each of said at least two PEG molecules comprising a functional group for cross-linking.

2. The precursor molecule of claim 1, wherein said PEG is selected from the group consisting of PEG-acrylate (PEG-Ac) and PEG-vinylsulfone (PEG-VS).

3. The precursor molecule of claim 1, wherein said PEG-Ac is selected from the group consisting of PEG-DA, 4-arm star PEG multi-Acrylate and 8-arm star PEG multi-Acrylate.

4. The precursor molecule of claim 3, wherein said PEG-DA is a 4-kDa PEG-DA, 6-kDa PEG-DA, 10-kDa PEG-DA, 14-kDa PEG-DA and/or 20-kDa PEG-DA.

5. The precursor molecule of claim 3, wherein a molar ratio of PEG-DA:fibrinogen is 2-400:1.

6. The precursor molecule of claim 3, wherein a molar ratio of PEG-DA:fibrinogen is 100-200:1.

7. The precursor molecule of claim 1, wherein said fibrinogen protein retains an activity of mediating tissue regeneration following in vivo administration.

8. A method of generating a scaffold comprising:
   (a) generating the precursor molecules of claim 1; and subsequently
   (b) cross-linking said precursor molecules to thereby generate the scaffold.

9. A precursor molecule comprising a fibrinogen protein which is denatured and retains an activity of mediating tissue regeneration following in vivo administration, and at least two PEG molecules covalently connected to free thiol groups of said fibrinogen protein, each of said at least two PEG molecules comprising a functional group for cross-linking.

* * * * *

SEQUENCE LISTING

```
<160> NUMBER OF SEQ ID NOS: 6

<210> SEQ ID NO 1
<211> LENGTH: 391
<212> TYPE: PRT
<213> ORGANISM: Bos taurus

<400> SEQUENCE: 1

Val Asp Ile Asp Ile Lys Ile Arg Ser Cys Lys Gly Ser Cys Ser Lys
1               5                   10                  15

Ala Leu Glu His Lys Val Asp Leu Glu Asp Tyr Lys Asn Gln Gln Lys
            20                  25                  30

Gln Leu Glu Gln Val Ile Ala Ile Asn Leu Leu Pro Ser Arg Asp Ile
        35                  40                  45

Gln Tyr Leu Pro Leu Ile Lys Met Ser Thr Ile Thr Gly Pro Val Pro
    50                  55                  60

Lys Lys Phe Lys Ser Gln Leu Gln Glu Ala Pro Leu Glu Trp Lys Ala
65                  70                  75                  80

Leu Leu Glu Met Gln Gln Thr Lys Met Val Leu Glu Thr Phe Gly Gly
                85                  90                  95

Asp Gly His Ala Arg Gly Asp Ser Val Ser Gln Gly Thr Gly Leu Ala
            100                 105                 110

Pro Gly Ser Pro Arg Lys Pro Gly Thr Ser Ser Ile Gly Asn Val Asn
        115                 120                 125

Pro Gly Ser Tyr Gly Pro Gly Ser Ser Gly Thr Trp Asn Pro Gly Arg
    130                 135                 140

Pro Glu Pro Gly Ser Ala Gly Thr Trp Asn Pro Gly Arg Pro Glu Pro
145                 150                 155                 160

Gly Ser Ala Gly Thr Trp Asn Pro Gly Arg Pro Glu Pro Gly Ser Ala
                165                 170                 175

Gly Thr Trp Asn Pro Gly Arg Pro Glu Pro Gly Ser Gly Gly Thr Trp
```

```
              180                 185                 190
Asn Thr Gly Ser Ser Gly Ser Ser Phe Arg Pro Asp Ser Ser Gly
            195                 200                 205

His Gly Asn Ile Arg Pro Ser Ser Pro Asp Trp Gly Thr Phe Arg Glu
    210                 215                 220

Glu Gly Ser Val Ser Ser Gly Thr Lys Gln Glu Phe His Thr Gly Lys
225                 230                 235                 240

Leu Val Thr Thr Lys Gly Asp Lys Glu Leu Leu Ile Asp Asn Glu Lys
                245                 250                 255

Val Thr Ser Gly His Thr Thr Thr Arg Arg Ser Cys Ser Lys Val
            260                 265                 270

Ile Thr Lys Thr Val Thr Asn Ala Asp Gly Arg Thr Glu Thr Thr Lys
    275                 280                 285

Glu Val Val Lys Ser Glu Asp Gly Ser Asp Cys Gly Asp Ala Asp Phe
290                 295                 300

Asp Trp His His Thr Phe Pro Ser Arg Gly Asn Leu Asp Asp Phe Phe
305                 310                 315                 320

His Arg Asp Lys Asp Asp Phe Phe Thr Arg Ser Ser His Glu Phe Asp
                325                 330                 335

Gly Arg Thr Gly Leu Ala Pro Glu Phe Ala Ala Leu Gly Glu Ser Gly
            340                 345                 350

Ser Ser Ser Ser Lys Thr Ser Thr His Ser Lys Gln Phe Val Ser Ser
            355                 360                 365

Ser Thr Thr Val Asn Arg Gly Gly Ser Ala Ile Glu Ser Lys His Phe
    370                 375                 380

Lys Met Glu Asp Glu Ala Glu
385                 390

<210> SEQ ID NO 2
<211> LENGTH: 425
<212> TYPE: PRT
<213> ORGANISM: Bos taurus

<400> SEQUENCE: 2

Ser Gly Gly Gly Tyr Arg Ala Arg Pro Ala Thr Ala Thr Val Gly Gln
1               5                   10                  15

Lys Lys Val Glu Arg Lys Pro Pro Asp Ala Asp Gly Cys Leu His Ala
            20                  25                  30

Asp Pro Asp Leu Gly Val Leu Cys Pro Thr Gly Cys Lys Leu Gln Asp
        35                  40                  45

Thr Leu Val Arg Gln Glu Arg Pro Ile Arg Lys Ser Ile Glu Asp Leu
    50                  55                  60

Arg Asn Thr Val Asp Ser Val Ser Arg Thr Ser Ser Ser Thr Phe Gln
65                  70                  75                  80

Tyr Ile Thr Leu Leu Lys Asn Met Trp Lys Gly Arg Gln Asn Gln Val
                85                  90                  95

Gln Asp Asn Glu Asn Val Val Asn Glu Tyr Ser Ser His Leu Glu Lys
            100                 105                 110

His Gln Leu Tyr Ile Asp Glu Thr Val Lys Asn Asn Ile Pro Thr Lys
        115                 120                 125

Leu Arg Val Leu Arg Ser Ile Leu Glu Asn Leu Arg Ser Lys Ile Gln
    130                 135                 140

Lys Leu Glu Ser Asp Val Ser Thr Gln Met Glu Tyr Cys Arg Thr Pro
145                 150                 155                 160
```

```
Cys Thr Val Thr Cys Asn Ile Pro Val Val Ser Gly Lys Glu Cys Glu
                165                 170                 175

Lys Ile Ile Arg Asn Glu Gly Glu Thr Ser Glu Met Tyr Leu Ile Gln
            180                 185                 190

Pro Glu Asp Ser Ser Lys Pro Tyr Arg Val Tyr Cys Asp Met Lys Thr
        195                 200                 205

Glu Lys Gly Gly Trp Thr Val Ile Gln Asn Arg Gln Asp Gly Ser Val
    210                 215                 220

Asp Phe Gly Arg Lys Trp Asp Pro Tyr Lys Gln Gly Phe Gly Asn Ile
225                 230                 235                 240

Ala Thr Asn Ala Glu Gly Lys Lys Tyr Cys Gly Val Pro Gly Glu Tyr
                245                 250                 255

Trp Leu Gly Asn Asp Arg Ile Ser Gln Leu Thr Asn Met Gly Pro Thr
            260                 265                 270

Lys Leu Leu Ile Glu Met Glu Asp Trp Lys Gly Asp Lys Val Thr Ala
        275                 280                 285

Leu Tyr Glu Gly Phe Thr Val Gln Asn Glu Ala Asn Lys Tyr Gln Leu
    290                 295                 300

Ser Val Ser Lys Tyr Lys Gly Thr Ala Gly Asn Ala Leu Ile Glu Gly
305                 310                 315                 320

Ala Ser Gln Leu Val Gly Glu Asn Arg Thr Met Thr Ile His Asn Ser
                325                 330                 335

Met Phe Phe Ser Thr Tyr Asp Arg Asp Asn Asp Gly Trp Lys Thr Thr
            340                 345                 350

Asp Pro Arg Lys Gln Cys Ser Lys Glu Asp Gly Gly Gly Trp Trp Tyr
        355                 360                 365

Asn Arg Cys His Ala Ala Asn Pro Asn Gly Arg Tyr Tyr Trp Gly Gly
    370                 375                 380

Ala Tyr Thr Trp Asp Met Ala Lys His Gly Thr Asp Asp Gly Val Val
385                 390                 395                 400

Trp Met Asn Trp Gln Gly Ser Trp Tyr Ser Met Lys Lys Met Ser Met
                405                 410                 415

Lys Ile Arg Pro Tyr Phe Pro Glu Gln
            420                 425

<210> SEQ ID NO 3
<211> LENGTH: 444
<212> TYPE: PRT
<213> ORGANISM: Bos taurus

<400> SEQUENCE: 3

Met Ser Trp Ser Ser His Pro Pro Ser Val Ile Phe Tyr Ile Leu Ser
1               5                   10                  15

Leu Leu Ser Ser Ala Cys Leu Ala Tyr Val Ala Thr Arg Asp Asn Cys
            20                  25                  30

Cys Ile Leu Asp Glu Arg Phe Gly Ser Tyr Cys Pro Thr Thr Cys Gly
        35                  40                  45

Ile Ala Asp Phe Leu Asn Asn Tyr Gln Thr Ser Val Asp Lys Asp Leu
    50                  55                  60

Arg Thr Leu Glu Gly Ile Leu Tyr Gln Val Glu Asn Lys Thr Ser Glu
65                  70                  75                  80

Ala Arg Glu Leu Val Lys Ala Ile Gln Ile Ser Tyr Asn Pro Asp Gln
                85                  90                  95

Pro Ser Lys Pro Asn Asn Ile Glu Ser Ala Thr Lys Asn Ser Lys Ser
            100                 105                 110
```

Met Met Glu Glu Ile Met Lys Tyr Glu Thr Leu Ile Ser Thr His Glu
            115                 120                 125

Ser Thr Ile Arg Phe Leu Gln Glu Val Tyr Asn Ser Asn Ser Gln Lys
    130                 135                 140

Ile Val Asn Leu Arg Asp Lys Val Val Gln Leu Glu Ala Asn Cys Gln
145                 150                 155                 160

Glu Pro Cys Gln Asp Thr Val Lys Ile His Asp Val Thr Gly Arg Asp
                165                 170                 175

Cys Gln Asp Val Ala Asn Lys Gly Ala Lys Glu Ser Gly Leu Tyr Phe
            180                 185                 190

Ile Arg Pro Leu Lys Ala Lys Gln Phe Leu Val Tyr Cys Glu Ile Asp
            195                 200                 205

Gly Ser Gly Asn Gly Trp Thr Val Phe Gln Lys Arg Leu Asp Gly Ser
        210                 215                 220

Leu Asp Phe Lys Lys Asn Trp Ile Gln Tyr Lys Glu Gly Phe Gly His
225                 230                 235                 240

Leu Ser Pro Thr Gly Thr Gly Asn Thr Glu Phe Trp Leu Gly Asn Glu
                245                 250                 255

Lys Ile His Leu Ile Ser Thr Gln Ser Ser Ile Pro Tyr Val Leu Arg
            260                 265                 270

Ile Gln Leu Glu Asp Trp Asn Gly Arg Thr Ser Thr Ala Asp Tyr Ala
            275                 280                 285

Ser Phe Lys Val Thr Gly Glu Asn Asp Lys Tyr Arg Leu Thr Tyr Ala
        290                 295                 300

Tyr Phe Ile Gly Gly Asp Ala Gly Asp Ala Phe Asp Gly Tyr Asp Phe
305                 310                 315                 320

Gly Asp Asp Ser Ser Asp Lys Phe Phe Thr Ser His Asn Gly Met Gln
                325                 330                 335

Phe Ser Thr Trp Asp Ser Asp Asn Asp Lys Tyr Asp Gly Asn Cys Ala
            340                 345                 350

Glu Gln Val Gly Ile Gly Trp Trp Met Asn Lys Cys His Ala Gly His
        355                 360                 365

Leu Asn Gly Val Tyr Tyr Gln Gly Gly Thr Tyr Ser Lys Thr Ser Thr
    370                 375                 380

Pro Asn Gly Tyr Asp Asn Gly Ile Ile Trp Ala Thr Trp Lys Ser Arg
385                 390                 395                 400

Trp Tyr Ser Met Lys Lys Thr Thr Met Lys Ile Ile Pro Leu Asn Arg
                405                 410                 415

Leu Ala Ile Gly Glu Gly Gln His Gln Leu Gly Gly Ala Lys Gln
            420                 425                 430

Val Gly Val Glu His His Val Glu Ile Glu Tyr Asp
        435                 440

<210> SEQ ID NO 4
<211> LENGTH: 644
<212> TYPE: PRT
<213> ORGANISM: Homo sapiens

<400> SEQUENCE: 4

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys

```
                35                  40                  45
Asp Ser Asp Trp Pro Phe Cys Ser Asp Glu Asp Trp Asn Tyr Lys Cys
 50                  55                  60

Pro Ser Gly Cys Arg Met Lys Gly Leu Ile Asp Glu Val Asn Gln Asp
 65                  70                  75                  80

Phe Thr Asn Arg Ile Asn Lys Leu Lys Asn Ser Leu Phe Glu Tyr Gln
                 85                  90                  95

Lys Asn Asn Lys Asp Ser His Ser Leu Thr Thr Asn Ile Met Glu Ile
                100                 105                 110

Leu Arg Gly Asp Phe Ser Ser Ala Asn Asn Arg Asp Asn Thr Tyr Asn
                115                 120                 125

Arg Val Ser Glu Asp Leu Arg Ser Arg Ile Glu Val Leu Lys Arg Lys
                130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
                180                 185                 190

Asp Leu Lys Asp Tyr Glu Asp Gln Gln Lys Gln Leu Glu Gln Val Ile
                195                 200                 205

Ala Lys Asp Leu Leu Pro Ser Arg Asp Arg Gln His Leu Pro Leu Ile
210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
                260                 265                 270

Gly Ser Thr Ser Tyr Gly Thr Gly Ser Glu Thr Glu Ser Pro Arg Asn
                275                 280                 285

Pro Ser Ser Ala Gly Ser Trp Asn Ser Gly Ser Ser Gly Pro Gly Ser
                290                 295                 300

Thr Gly Asn Arg Asn Pro Gly Ser Ser Gly Thr Gly Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
                340                 345                 350

Arg Pro Gly Ser Thr Gly Thr Trp Asn Pro Gly Ser Ser Glu Arg Gly
                355                 360                 365

Ser Ala Gly His Trp Thr Ser Glu Ser Ser Val Ser Gly Ser Thr Gly
                370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
                420                 425                 430

Leu Val Thr Ser Lys Gly Asp Lys Glu Leu Arg Thr Gly Lys Glu Lys
                435                 440                 445

Val Thr Ser Gly Ser Thr Thr Thr Thr Arg Arg Ser Cys Ser Lys Thr
                450                 455                 460
```

```
Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
            485                 490                 495

Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
            530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Ser Thr Lys Arg Gly His Ala
            610                 615                 620

Lys Ser Arg Pro Val Arg Gly Ile His Thr Ser Pro Leu Gly Lys Pro
625                 630                 635                 640

Ser Leu Ser Pro

<210> SEQ ID NO 5
<211> LENGTH: 491
<212> TYPE: PRT
<213> ORGANISM: Homo sapiens

<400> SEQUENCE: 5

Met Lys Arg Met Val Ser Trp Ser Phe His Lys Leu Lys Thr Met Lys
1               5                   10                  15

His Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
            35                  40                  45

Leu Asp Lys Lys Arg Glu Glu Ala Pro Ser Leu Arg Pro Ala Pro Pro
            50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
            115                 120                 125

Glu Leu Asn Asn Asn Val Glu Ala Val Ser Gln Thr Ser Ser Ser Ser
            130                 135                 140

Phe Gln Tyr Met Tyr Leu Leu Lys Asp Leu Trp Gln Lys Arg Gln Lys
145                 150                 155                 160

Gln Val Lys Asp Asn Glu Asn Val Val Asn Glu Tyr Ser Ser Glu Leu
                165                 170                 175

Glu Lys His Gln Leu Tyr Ile Asp Glu Thr Val Asn Ser Asn Ile Pro
            180                 185                 190
```

```
Thr Asn Leu Arg Val Leu Arg Ser Ile Leu Glu Asn Leu Arg Ser Lys
        195                 200                 205

Ile Gln Lys Leu Glu Ser Asp Val Ser Ala Gln Met Glu Tyr Cys Arg
    210                 215                 220

Thr Pro Cys Thr Val Ser Cys Asn Ile Pro Val Val Ser Gly Lys Glu
225                 230                 235                 240

Cys Glu Glu Ile Ile Arg Lys Gly Gly Glu Thr Ser Glu Met Tyr Leu
                245                 250                 255

Ile Gln Pro Asp Ser Ser Val Lys Pro Tyr Arg Val Tyr Cys Asp Met
            260                 265                 270

Asn Thr Glu Asn Gly Gly Trp Thr Val Ile Gln Asn Arg Gln Asp Gly
        275                 280                 285

Ser Val Asp Phe Gly Arg Lys Trp Asp Pro Tyr Lys Gln Gly Phe Gly
    290                 295                 300

Asn Val Ala Thr Asn Thr Asp Gly Lys Asn Tyr Cys Gly Leu Pro Gly
305                 310                 315                 320

Glu Tyr Trp Leu Gly Asn Asp Lys Ile Ser Gln Leu Thr Arg Met Gly
                325                 330                 335

Pro Thr Glu Leu Leu Ile Glu Met Glu Asp Trp Lys Gly Asp Lys Val
            340                 345                 350

Lys Ala His Tyr Gly Gly Phe Thr Val Gln Asn Glu Ala Asn Lys Tyr
        355                 360                 365

Gln Ile Ser Val Asn Lys Tyr Arg Gly Thr Ala Gly Asn Ala Leu Met
    370                 375                 380

Asp Gly Ala Ser Gln Leu Met Gly Glu Asn Arg Thr Met Thr Ile His
385                 390                 395                 400

Asn Gly Met Phe Phe Ser Thr Tyr Asp Arg Asp Asn Asp Gly Trp Leu
                405                 410                 415

Thr Ser Asp Pro Arg Lys Gln Cys Ser Lys Glu Asp Gly Gly Gly Trp
            420                 425                 430

Trp Tyr Asn Arg Cys His Ala Ala Asn Pro Asn Gly Arg Tyr Tyr Trp
        435                 440                 445

Gly Gly Gln Tyr Thr Trp Asp Met Ala Lys His Gly Thr Asp Asp Gly
    450                 455                 460

Val Val Trp Met Asn Trp Lys Gly Ser Trp Tyr Ser Met Arg Lys Met
465                 470                 475                 480

Ser Met Lys Ile Arg Pro Phe Phe Pro Gln Gln
                485                 490

<210> SEQ ID NO 6
<211> LENGTH: 453
<212> TYPE: PRT
<213> ORGANISM: Homo sapiens

<400> SEQUENCE: 6

Met Ser Trp Ser Leu His Pro Arg Asn Leu Ile Leu Tyr Phe Tyr Ala
1               5                   10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
```

```
                65                  70                  75                  80
            Ser Glu Val Lys Gln Leu Ile Lys Ala Ile Gln Leu Thr Tyr Asn Pro
                                85                  90                  95

Asp Glu Ser Ser Lys Pro Asn Met Ile Asp Ala Ala Thr Leu Lys Ser
                            100                 105                 110

Arg Lys Met Leu Glu Glu Ile Met Lys Tyr Glu Ala Ser Ile Leu Thr
                            115                 120                 125

His Asp Ser Ser Ile Arg Tyr Leu Gln Glu Ile Tyr Asn Ser Asn Asn
                            130                 135                 140

Gln Lys Ile Val Asn Leu Lys Glu Lys Val Ala Gln Leu Glu Ala Gln
            145                 150                 155                 160

Cys Gln Glu Pro Cys Lys Asp Thr Val Gln Ile His Asp Ile Thr Gly
                                165                 170                 175

Lys Asp Cys Gln Asp Ile Ala Asn Lys Gly Ala Lys Gln Ser Gly Leu
                            180                 185                 190

Tyr Phe Ile Lys Pro Leu Lys Ala Asn Gln Gln Phe Leu Val Tyr Cys
                            195                 200                 205

Glu Ile Asp Gly Ser Gly Asn Gly Trp Thr Val Phe Gln Lys Arg Leu
                            210                 215                 220

Asp Gly Ser Val Asp Phe Lys Lys Asn Trp Ile Gln Tyr Lys Glu Gly
            225                 230                 235                 240

Phe Gly His Leu Ser Pro Thr Gly Thr Thr Glu Phe Trp Leu Gly Asn
                                245                 250                 255

Glu Lys Ile His Leu Ile Ser Thr Gln Ser Ala Ile Pro Tyr Ala Leu
                            260                 265                 270

Arg Val Glu Leu Glu Asp Trp Asn Gly Arg Thr Ser Thr Ala Asp Tyr
                            275                 280                 285

Ala Met Phe Lys Val Gly Pro Glu Ala Asp Lys Tyr Arg Leu Thr Tyr
                            290                 295                 300

Ala Tyr Phe Ala Gly Gly Asp Ala Gly Asp Ala Phe Asp Gly Phe Asp
            305                 310                 315                 320

Phe Gly Asp Asp Pro Ser Asp Lys Phe Phe Thr Ser His Asn Gly Met
                                325                 330                 335

Gln Phe Ser Thr Trp Asp Asn Asp Asn Asp Lys Phe Glu Gly Asn Cys
                            340                 345                 350

Ala Glu Gln Asp Gly Ser Gly Trp Trp Met Asn Lys Cys His Ala Gly
                            355                 360                 365

His Leu Asn Gly Val Tyr Tyr Gln Gly Gly Thr Tyr Ser Lys Ala Ser
                            370                 375                 380

Thr Pro Asn Gly Tyr Asp Asn Gly Ile Ile Trp Ala Thr Trp Lys Thr
            385                 390                 395                 400

Arg Trp Tyr Ser Met Lys Lys Thr Thr Met Lys Ile Ile Pro Phe Asn
                                405                 410                 415

Arg Leu Thr Ile Gly Glu Gly Gln His His Leu Gly Gly Ala Lys
                            420                 425                 430

Gln Val Arg Pro Glu His Pro Ala Glu Thr Glu Tyr Asp Ser Leu Tyr
                            435                 440                 445

Pro Glu Asp Asp Leu
                            450
```